(12) United States Patent
Gong et al.

(10) Patent No.: US 8,314,100 B2
(45) Date of Patent: Nov. 20, 2012

(54) 1-[6,7-SUBSTITUTED ALKOXYQUINOXALINYL)AMINOCARBONYL]-4-(HETERO)ARYLPIPERAZINE DERIVATIVES

(75) Inventors: Young-Dae Gong, Daejeon (KR); Moon-Kook Jeon, Daejeon (KR); Dong-Su Kim, Seoul (KR); Jae Yang Kong, Daejeon (KR); Gun-Do Kim, Daejeon (KR); Chang-Ho Ahn, Rockville, MD (US); Young Bok Lee, Rockville, MD (US)

(73) Assignees: Rexahn Pharmaceuticals, Inc., Rockville, MD (US); Korea Research Institute of Chemical Technology, Daejeon (KR)

( * ) Notice: Subject to any disclaimer, the term of this patent is extended or adjusted under 35 U.S.C. 154(b) by 15 days.

(21) Appl. No.: 11/667,923

(22) PCT Filed: Oct. 18, 2005

(86) PCT No.: PCT/KR2005/003463
§ 371 (c)(1),
(2), (4) Date: Jul. 17, 2008

(87) PCT Pub. No.: WO2006/054830
PCT Pub. Date: May 26, 2006

(65) Prior Publication Data
US 2008/0318963 A1    Dec. 25, 2008

(30) Foreign Application Priority Data
Nov. 17, 2004   (KR) .................. 10-2004-0094232
Nov. 17, 2004   (KR) .................. 10-2004-0094233

(51) Int. Cl.
*A61K 31/495*   (2006.01)
(52) U.S. Cl. .................. 514/249; 544/354; 544/390
(58) Field of Classification Search .................. 514/249; 544/354, 390
See application file for complete search history.

(56) References Cited

U.S. PATENT DOCUMENTS

| | | | |
|---|---|---|---|
| 4,291,033 | A | 9/1981 | Barnes et al. |
| 4,474,784 | A | 10/1984 | Barnes et al. |
| 6,028,195 | A | 2/2000 | Cho et al. |
| 6,683,184 | B2 | 1/2004 | Cho et al. |
| 2003/0092910 | A1 | 5/2003 | Cho et al. |

FOREIGN PATENT DOCUMENTS

| | | | |
|---|---|---|---|
| WO | WO 00/52001 | * | 9/2000 |
| WO | WO 01/95856 | * | 12/2001 |
| WO | WO-2004/043950 | | 5/2004 |
| WO | WO-2004/094410 | | 11/2004 |
| WO | WO 2006/054830 A | | 5/2006 |

OTHER PUBLICATIONS

Tomoda, Haruhiko et al.: "Synthesis and Physical Properties of Pyrido[1',2':1,2]imidazo[4,5-b]quinoxalines", *Bull.chem.Soc.Jpn.*, 71, pp. 1125-1135 (1998).
Sarges, Reinhard et al.: "4-Amino[1,2,4]triazolo[4,3-α]quinoxalines. A Novel Class of Potent Adenosine Receptor Antagonists and Potential Rapid-Onset Antidepressants", *J. Med. Chem.* 1990, 33, pp. 2240-2254.
Bigge, Christopher F. et al.: "Synthesis of 1,4,7,8,9,10-Hexahydro-9-methyl-6-nitropyrido[3,4-f]-quinoxaline-2,3-dione and Related Quinoxalindediones: Characterization of α-Amino-3-hydroxy-5-methyl-4-isoxazolepropionic Acid (and N-Methyl-D-Aspartate) Receptor and Anticonvulsant Activity", *J.Med.Chem.*, 1995, 38, pp. 3720-3740.
Skehan, Philip et al.: "New Colorimetric Cytotoxicity Assay for Anticancer-Drug Screening", *Articles*, vol. 82, No. 13, Jul. 4, 1990, pp. 1107-1112.
Wozniak, Marian et al.: "Regioselectivity of the Amination of Some Nitroquinoxalines by Liquid Ammonia/Potassium Permanaganate", *Liebigs Ann. Chem.*, 1992, pp. 899-902.
Hayashi, Eisaku et al.: "Anti-tumor Activity of Eighty Four Synthesized N-Heteroaromatic Compounds", *Yakugaku Zasshi*, 97 (9), pp. 1022-1033, 1977.
Registry No. 57315-33-0; Formula: C10 H11 N3 O; CA Index Name: 2-Quinoxalinamine, 3-ethoxy-.; copyright 2008, 5 pages.
Ager, Ian R. et al.: "Synthesis and Oral Antiallergic Activity of a Carboxylic Acids Derived from Imidazo[2,1-c][1,4]benzoxazines, Imidazo[1,2-a]quinolines, Imidazo[1,2-a]quinoxalinones,Pyrrolo[1,2-a]quinoxalinones,Pyrrolo[2,3-a]quinoxalinones and Imidazo[2,1-b]benzothiazoles", *J.Med.Chem.*, 1988, 31, pp. 1098-1115.
Nasielski-Hinkens et al., "Nucleophilic Substitutions on 2-Chloro-3-Nitroquinoxaline", Bull. Des Soc. Chim. Beiges (1988), 97 (11-12), pp. 919-926 (abstract only), Chem Abstracts Assession No. 1989:574060.

* cited by examiner

*Primary Examiner* — Douglas M Willis
(74) *Attorney, Agent, or Firm* — Venable LLP; Keith G. Haddaway

(57) ABSTRACT

The present invention related to a novel urea derivative for formula (I):

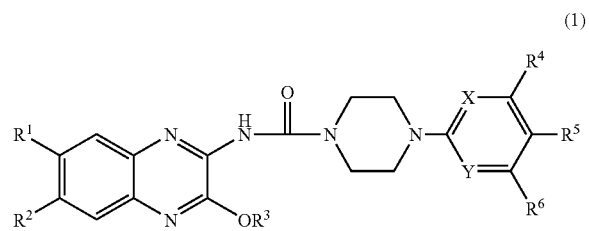

(1)

which is useful as an anti-cancer agent, its pharmaceutically acceptable acid addition salt or stereoisomer, and to a process for preparing the urea derivative and an anti-cancer composition comprising the same as an active ingredient.

12 Claims, No Drawings

1-[6,7-SUBSTITUTED ALKOXYQUINOXALINYL)AMINOCARBONYL]-4-(HETERO)ARYLPIPERAZINE DERIVATIVES

This application is a 371 of PCT/KR2005/003463 filed on Oct. 18, 2005, published on May 26, 2006 under publication number WO 2006/054830 A1 which claims priority benefits from Korean Patent Application No. 10-2004-0094233 filed Nov. 17, 2004 and Korean Patent Application No. 10-2004-0094232 filed Nov. 17, 2004, the disclosures of which are hereby incorporated by reference.

TECHNICAL FIELD

The present invention relates to novel quinoxaline-piperazine compounds, 1-[(6,7-substituted alkoxyquinoxalinyl) aminocarbonyl]-4-(hetero)arylpiperazine derivatives and pharmaceutically acceptable salt thereof, process for the preparation thereof, and therapeutic methods for the treatment of hyperproliferative disorders, including cancers, by administering quinoxaline-piperazine compounds.

BACKGROUND ART

Chemotherapeutics kill tumor cells by interfering with various stages of the cell division process. There are a number of classes of chemotherapeutics including alkylating agents (e.g., cyclophosphamide, carmustine, cisplatin), antimetabolites (e.g., methotrexate, 5-FU, gemcitabine), cytotoxic antibiotics (e.g., doxorubicin, mitomycin) and plant derivatives (e.g., paclitaxel, vincristine, etoposide). Chemotherapy is used as a primary treatment for leukemias, other blood cancers, and inoperable or metastatic solid cancers.

However, current chemotherapeutic agents have a few problems, including limited efficacy, debilitating adverse side effects and development of multidrug resistance.

Novel piperazine compounds may provide potent new therapeutic molecules for the treatment of disorders such as tumors. In association with new development of an anti-tumor agent, U.S. Patent Application Publication No. 2003/0092910 presents the piperazine compounds having formula (A)

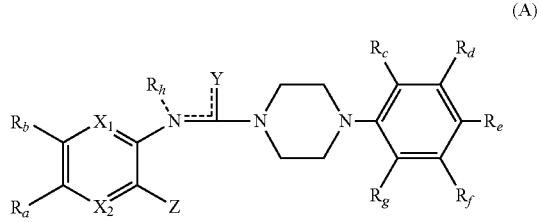

(A)

In U.S. Patent Application Publication No. 2003/0092910, the preparation of 1-[(2-alkoxyquinoxalin-3-yl)aminocarbonyl-4-arylpiperazine is presented wherein $R_a$ and $R_b$ are fused to form C3-C4 unsaturated ring. But the compounds of formula A have only hydrogen atom at C-5, C-6, C-7 and C-8 position of quinoxaline ring.

Namely, the compounds listed in U.S. Patent Application Publication No. 2003/0092910 has no other group except hydrogen at C-6 of quinoxaline ring of 1-[(2-alkoxyquinoxalin-3-yl)aminocarbonyl-4-arylpiperazine and the compounds with other groups except hydrogen at C-6 of quinoxaline have not been prepared and tested as an antitumor agent.

The present invention has studied 1-[(2-alkoxyquinoxalin-3-yl)aminocarbonyl-4-arylpiperazine derivatives because of its prominent antitumor activities with very low toxicities and presents novel 1-[(6,7-substituted alkoxyquinoxalinyl)aminocarbonyl]-4-(hetero)arylpiperazine derivatives with other functional groups except hydrogen at C-6 of quinoxaline ring of 1-[(2-alkoxyquinoxalin-3-yl)aminocarbonyl-4-arylpiperazine derivatives, the process of preparation and strong antitumor activities of these new compounds.

Accordingly, one object of the present invention is to provide the novel compounds, 1-[(6,7-substituted alkoxyquinoxalinyl)aminocarbonyl]-4-(hetero)arylpiperazine derivatives.

Another object of the present invention is to provide a process for the preparation of the novel compounds, 1-[(6,7-substituted alkoxyquinoxalinyl)aminocarbonyl]-4-(hetero) arylpiperazine derivatives.

A further object of the present invention is to use 1-[(6,7-substituted alkoxyquinoxalin-yl)aminocarbonyl]-4-(hetero) arylpiperazine derivatives as antitumor agent.

DISCLOSURE

The present invention comprises a novel quinoxalin-piperazine derivative of the general formula (1) or its pharmaceutically acceptable salt, process for the preparation thereof and their use in the treatment of a hyperproliferative disorder, disease or condition in a subject (e.g., a human patient or other animal subject). Methods according to the invention comprise administering to a subject an effective amount of a quinoxalin-piperazine compound according to the invention. Such a treatment can, e.g., prevent, ameliorate, and/or inhibit symptoms of the hyperproliferative condition, and/or can prevent or inhibit cellular proliferation or growth, for instance in a tumor, such as a malignant neoplasm. A treatment strategy of the invention would decrease the tumor burden, at least to a measurable degree, and improve survival of patients suffering from the hyperproliferative condition. Among the diseases, disorders and conditions susceptible to treatment by agents of the invention are neoplasms, and more specifically tumors of various origins (lung, colon, stomach, smooth muscle, esophagus, non-Hodgkin's lymphoma, non-small cell lung cancer, etc.).

Compounds Useful in Methods According to the Invention

Compounds useful in methods of the invention include quinoxaline-piperazine derivatives having formula (1), 1-[(6,7-substituted alkoxyquinoxalinyl)aminocarbonyl]-4-(hetero)arylpiperazine derivatives:

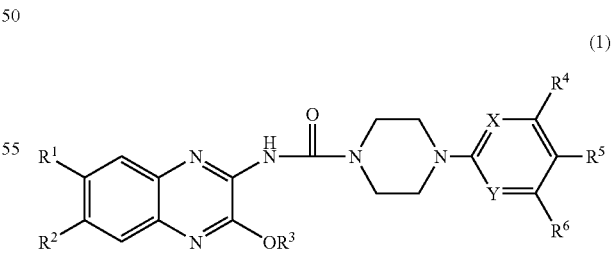

(1)

wherein X and Y are independently N or C—$R^7$; $R^1$ and $R^2$ are independently hydrogen, $C_1$-$C_6$alkoxy, $C_1$-$C_6$ alkyl or halogen; $R^3$ is $C_1$-$C_6$ alkyl; $R^4$, $R^5$, $R^6$ and $R^7$ are independently hydrogen, $C_1$-$C_6$ alkoxy, $C_1$-$C_6$ alkyl, $C_1$-$C_6$haloalkyl, $C_1$-$C_6$ alkylcarbonyl, halogen, cyano or nitro.

In the above definitions, the designation 'halogen' represents F, Cl, Br or I.

The designation 'alkoxy' represents $C_1$-$C_6$ alkoxy containing methoxy, ethoxy, propoxy, isopropoxy, butoxy, isobutoxy and t-butoxy.

The designation 'alkyl' represents $C_1$-$C_6$ alkyl containing methyl, ethyl, propyl, isopropyl, n-butyl, isobutyl, t-butyl, n-pentyl, isopentyl, n-hexyl, isohexyl and cyclohexyl.

The designation 'haloalkyl' represents $C_1$-$C_6$ alkyl, for example trifluoromethyl, in which hydrogen was exchanged with halogen such as F or Cl.

The designation 'alkylcarbonyl' represents carbonyl ketonized with alkyl such as methylcarbonyl or ethylcarbonyl.

It is preferably understood that, in the structure of formula (1), X and Y are independently N, C—H, C—F, C—Cl, C—CN, C—CH$_3$, or C—OCH$_3$, $R^1$ and $R^2$ are hydrogen, F, Cl, methyl or methoxy, $R^3$ is methyl, $R^4$, $R^5$, and $R^6$ are independently hydrogen, Cl, Br, nitro, methyl, trifluoromethyl, methoxy or acetyl and $R^7$ is hydrogen, F, Cl, cyano, methyl or methoxy.

This invention also presents a process for the preparation of the compounds of general formula (1). The preparation method of formula (1) comprises a two-step procedure as shown in the following scheme 1. Scheme 1 comprises reacting a compound of the general formula (2), 6,7-substituted-2-alkoxy-3-aminoquinoxaline, with an L-C(=O)-L' group-providing agent in a conventional organic solvent in the presence of a base to obtain a compound of the general formula (3) and successively reacting the compound of the general formula (3) with a compound of the general formula (4), 1-(hetero)arylpiperazine derivatives, in a conventional organic solvent in the presence of a base to give the compound of the general formula (1)

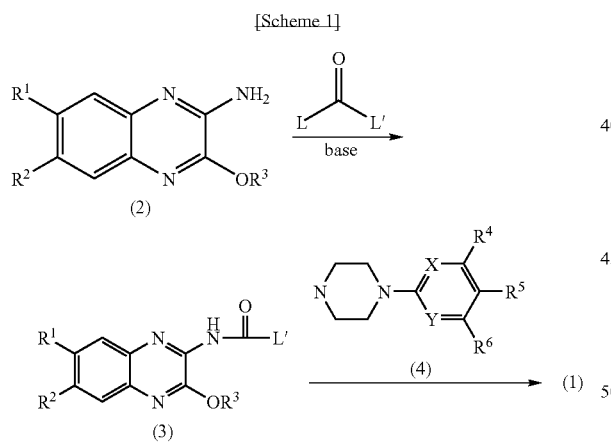

[Scheme 1]

wherein X, Y, $R^1$, $R^2$, $R^3$, $R^4$, $R^5$ and $R^6$ are the same as defined above, and L and L' are independently imidazole, Cl, ethoxy, phenoxy or 4-nitrophenoxy.

The two-step reaction in scheme 1 may be carried out successively without purification of the compound of the general formula (3) which is an intermediate produced in the above process.

The process for the preparation of the compounds of general formula (1) in scheme 1 may be explained in detail as follows:

The L-C(=O)-L' group-providing agent used in the above reaction may include 1,1-carbonyldiimidazole, phosgene, carbonyldiphenoxide, phenylchloroformate, 4-nitro phenylchloroformate and ethylchloroformate, and it may be used in an amount of 1.0-1.5 equivalents, preferably 1.0-1.1 equivalents with reference to the starting compound.

The reaction may be carried out in a conventional organic solvent such as, for example, tetrahydrofuran (THF), dichloromethane, acetonitrile, chloroform and dimethylformamide.

And also the reaction is preferably carried out in the presence of a coupling agent such as a conventional inorganic or organic base. Such conventional inorganic or organic bases used in the reaction may include sodium hydride, potassium hydride, sodium hydroxide, potassium hydroxide, sodium carbonate, potassium carbonate, cesium carbonate, sodium bicarbonate, potassium bicarbonate, triethylamine, pyridine and 1,8-diazabicyclo[5.4.0]undec-7-ene (hereinafter DBU).

The reaction may be carried out at a temperature between 0° C. and boiling point of the solvent used, preferably at room temperature to 100° C. and for 5-48 hours, preferably for 10-24 hours.

The second step in scheme 1, reaction of the compound (3) with the compound (4) to give the compound (1) may be carried out in the presence of a conventional organic solvent at the temperature of 50-100° C. for 5-48 hours. The compound (4) may be used by 1.0-1.5 equivalent.

And also the reaction is preferably carried out in the presence of a conventional inorganic or organic base, such as sodium hydride, potassium hydride, sodium hydroxide, potassium hydroxide, sodium carbonate, potassium carbonate, cesium carbonate, sodium bicarbonate, potassium bicarbonate, triethylamine, pyridine, DBU or the like.

The isolation and purification of the compounds (2), (3) and (1) in Scheme 1 were performed with multi column chromatography (Quad$^{3+}$; Biotage Co., VA, USA) and high-speed liquid column chromatography with auto sampler and structure of the compounds of the general formula (1) was analysed and confirmed with NMR and Mass spectrum.

And also the compounds of the general formula (2) that are used as the starting material, 6,7-substituted-2-alkoxy-3-aminoquinoxaline, are novel compounds and may be prepared by the following scheme 2; reacting a compound of the general formula (5) with sodium alkoxide which is NaOR$^3$ (R$^3$ is $C_1$-$C_6$ alkyl) to give a compound of the general formula (2);

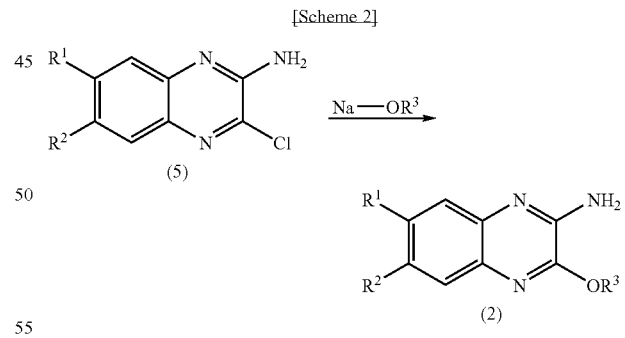

[Scheme 2]

wherein $R^1$, $R^2$ and $R^3$ are the same as defined in scheme 1.

The compound of the general formula (5) may be prepared by a known method described in, for example, *J. Med. Chem.*, 1995, 38, 3720-3740 or *Bull. Chem. Soc. Jpn.*, 1998, 71, 1125-1135.

The alkoxy reaction in scheme 2 may be carried out with sodium alkoxide in a conventional organic solvent such as THF and sodium alkoxide may be used in an amount of 1.0-10.0 equivalents, preferably 1.0-1.1 equivalents with reference to the starting compound, the compound of the general formula (5).

Also a compound of the general formula (2) may be prepared by the following scheme 3; reacting a compound of the general formula (6) with 2,4-dimethoxybenzylamine to give a compound of the general formula (7) and reacting the compound of the formula (7) with trifluoroacetic acid (TFA) to give a compound of the general formula (2);

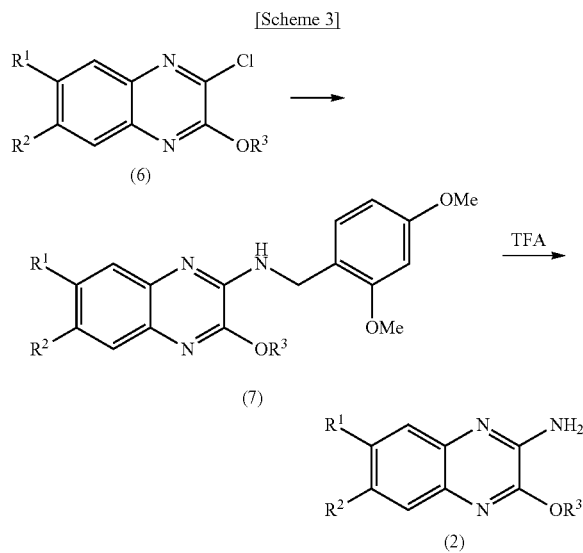

wherein R¹, R² and are the same as defined in scheme 1.

The compound of the general formula (6) may be prepared by a known method described in, for example, *J. Med. Chem.* 1990, 33, 2240-2254.

The reaction of the compound of the general formula (6) with 2,4-dimethoxybenzylamine in scheme 2 may be carried out in a conventional organic solvent such as dimethylsulfoxide to produce a compound of the general formula (7); and 2,4-dimethoxybenzylamine may be used in an amount of 1.0-5.0 equivalents, preferably 1.0-1.1 equivalents with reference to the compound of the general formula (6).

And then the reaction of the compound of the general formula (7) with trifluoroacetic acid may be carried out in a conventional organic solvent such as dichloromethane to give a compound of the general formula (2). Trifluoroacetic acid may be used in an amount of 0.5-1.5 equivalents, preferably 1.0 equivalent with reference to dichloromethane.

Compounds of the present invention can be very active against a wide range of hyperproliferative diseases, including tumors and used as an anti-tumor agent.

The compounds of the present invention can be also mixed with pharmaceutically acceptable vehicles by a known method to give pharmaceutical compositions and thus the pharmaceutical compositions can be used to prevent or treat various kinds of tumors of human beings or mammals.

Therefore, the present invention includes pharmaceutical compositions containing a compound of the general formula (1) or a pharmaceutically acceptable salt thereof as an active ingredient.

Pharmaceutically acceptable salts of compounds of the general formula (1) are pharmaceutically acceptable inorganic, organic acids, alkali metal and ammonium; for example, salts with inorganic acids such as hydrochloric acid, bromic acid, sulfuric acid, sodium hydrogensulfate, phosphoric acid, nitric acid, carbonic acid; salts with organic acids such as formic acid, acetic acid, propionic acid, oxalic acid, succinic acid, benzoic acid, citric acid, maleic acid, malonic acid, tartaric acid, gluconic acid, lactic acid, fumaric acid, lactobionic acid, salicylic acid, acetyl salicylic acid (aspirin); salts with amino acids such as glycine, alanine, valine, leucine, isoleucine, serine, cysteine, cystine, asparaginic acid, glutamic acid, lysine, arginine, tyrosine, proline; salts with sulfonic acids such as methane sulfonic acid, ethane sulfonic acid, benzene sulfonic acid, toluene sulfonic acid; an alkali metal salt, for example, a sodium or potassium salt; an alkali earth metal salt, for example, a calcium or magnesium salt; an ammonium salt; a salt with an organic base which affords a physiologically-acceptable, for example a salt with methylamine, dimethylamine, trimethylamine, piperidine, morpholine or tris-(2-hydroxyethyl)amine, or the like.

Furthermore, the novel compounds of the general formula (1) and pharmaceutically acceptable salts thereof may be combined with a non-toxic pharmaceutically acceptable vehicle such as carrier, adjuvant, and expient and then the mixture may be administered orally or parenterally in the form of tablets, capsules, troches, solutions, suspensions to prevent or treat various kinds of tumors of human beings or mammals.

Vehicles which can be used in the preparation of pharmaceutical compositions containing the compound of the general formula (1) as the active ingredient may include a sweetening agent, a binding agent, a dissolving agent, aids for dissolution, a wetting agent, an emulsifying agent, an isotonic agent, an adsorbent, a degrading agent, an antioxidant, an antiseptics, a lubricating agent, a filler, perfume or the like; such as lactose, dextrose, sucrose, mannitol, sorbitol, cellulose, glycine, silica, talc, stearic acid, stearin, magnesium stearate, calcium stearate, magnesium aluminum silicate, starch, gelatine, tragacanth gum, glycine, silica, alginic acid, sodium alginate, methyl cellulose, sodium carboxy methyl cellulose, agar, water, ethanol, polyethylenglycol, polyvinyl pyrrolidone, sodium chloride, potassium chloride, orange essence, strawberry essence, vanilla aroma or the like.

Daily dosage of the compound of the general formula (1) may be varied depending on age, body weight, sex of a patient, type of administration, health condition, degree of disease, etc. and generally 0.01 mg to 5,000 mg per day for 70 kg adult may be administered one to several times according to a doctor's prescription or a pharmacist's indication.

BEST MODE

The invention may be further clarified by reference to the following Examples, which serve to exemplify some of the preferred embodiments, and not to limit the invention in any way.

Example 1

1-[(6-Fluoro-2-methoxyquinoxalin-3-yl)aminocarbonyl]-4-phenylpiperazine (Compound 1)

a) 3-Amino-6-fluoro-2-methoxyquinoxaline

To 3-amino-2-chloro-6-fluoroquinoxaline (550 mg, 2.78 mmol) dissolved in tetrahydrofuran (40 ml), 25 wt % sodium methoxide (6.01 g, 27.8 mmol) in methanol was added at room temperature and stirred further at room temperature for 1 hour. The resulting mixture was concentrated under the reduced pressure to remove the solvent. The product was extracted with dichloromethane and the organic layer was washed with water and dried over MgSO₄. After concentration under the reduced pressure, the crude product was purified by SiO$_2$ column chromatography. Extraction of the residue with a n-hexane:ethyl acetate (2:1) mixture and concentration gave 491 mg of the titled compound (yield, 91%).

b) Ethyl N-(6-fluoro-2-methoxyquinoxalin-3-yl)carbamate

3-Amino-6-fluoro-2-methoxyquinoxaline (580 mg, 3.00 mmol) and ethyl chloroformate (391 mg, 3.60 mmol) were dissolved in dichloromethane (50 ml) at room temperature and thereto pyridine (285 mg, 3.60 mmol) was added. The mixture was stirred at room temperature for 10 hours and concentrated under the reduced pressure to remove the solvent, and purified by SiO$_2$ column chromatography. Extraction of the residue with a n-hexane:ethyl acetate (3:1) mixture and concentration gave 740 mg of the titled compound (yield, 93%).

c) 1-[(6-Fluoro-2-methoxyquinoxalin-3-yl)aminocarbonyl]-4-phenylpiperazine

Ethyl N-(6-fluoro-2-methoxyquinoxalin-3-yl)carbamate (27 mg, 0.10 mmol) and 1-phenylpiperazine (24 mg, 0.15 mmol) were dissolved in tetrahydrofuran (2 ml) at room temperature and thereto DBU (23 mg, 0.15 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (2:1) mixture and concentration gave 34 mg of the titled compound (yield, 88%). $^1$H NMR (300 MHz, CDCl$_3$): δ 3.29 (s, 4H), 3.77 (s, 3H), 4.14 (s, 4H), 6.89-6.97 (m, 4H), 7.24-7.56 (m, 5H), 7.62-7.71 (m, 1H)

Example 2

1-[(6-Fluoro-2-methoxyquinoxalin-3-yl)aminocarbonyl]-4-(2-methoxyphenyl)piperazine (Compound 2)

Ethyl N-(6-fluoro-2-methoxyquinoxalin-3-yl)carbamate and 1-(2-methoxyphenyl)piperazine were reacted by the same way with the example 1 to obtain the titled compound (yield, 84%). $^1$H NMR (200 MHz, CDCl$_3$): δ 3.15 (s, 4H), 3.79-3.87 (m, 6H), 4.11 (s, 4H), 6.86-7.02 (m, 4H), 7.18-7.22 (m, 1H), 7.39-7.50 (m, 1H), 7.65-7.72 (m, 1H).

Example 3

1-[(6-Fluoro-2-methoxyquinoxalin-3-yl)aminocarbonyl]-4-(3-methoxyphenyl)piperazine (Compound 3)

Ethyl N-(6-fluoro-2-methoxyquinoxalin-3-yl)carbamate and 1-(3-methoxyphenyl)piperazine were reacted by the same way with the example 1 to obtain the titled compound (yield, 87%). $^1$H NMR (300 MHz, CDCl$_3$): δ 3.28 (s, 4H), 3.80 (s, 6H), 4.13 (s, 4H), 6.45-6.58 (m, 3H), 7.01 (s, 1H), 7.17-7.23 (m, 2H), 7.37-7.70 (m, 2H).

Example 4

1-[(6-Fluoro-2-methoxyquinoxalin-3-yl)aminocarbonyl]-4-(4-methoxyphenyl)piperazine (Compound 4)

Ethyl N-(6-fluoro-2-methoxyquinoxalin-3-yl)carbamate and 1-(4-methoxyphenyl)piperazine were reacted by the same way with the example 1 to obtain the titled compound (yield, 80%). $^1$H NMR (200 MHz, CDCl$_3$): δ 3.18 (s, 4H), 3.79 (s, 6H), 4.08-4.15 (m, 4H), 6.85-6.98 (m, 4H), 7.22-7.76 (m, 4H).

Example 5

1-[(6-Fluoro-2-methoxyquinoxalin-3-yl)aminocarbonyl]-4-(3,5-dimethoxyphenyl)piperazine (Compound 5)

Ethyl N-(6-fluoro-2-methoxyquinoxalin-3-yl)carbamate and 1-(3,5-dimethoxyphenyl)piperazine were reacted by the same way with the example 1 to obtain the titled compound (yield, 72%). MS (ESI) m/z 442 (M+1).

Example 6

1-[(6-Fluoro-2-methoxyquinoxalin-3-yl)aminocarbonyl]-4-(3,4,5-trimethoxyphenyl)piperazine (Compound 6)

Ethyl N-(6-fluoro-2-methoxyquinoxalin-3-yl)carbamate and 1-(3,4,5-trimethoxyphenyl)piperazine were reacted by the same way with the example 1 to obtain the titled compound (yield, 76%). $^1$H NMR (200 MHz, CDCl$_3$): δ 3.22 (s, 4H), 3.79-3.85 (m, 12H), 4.13 (s, 4H), 6.19 (s, 2H), 7.20-7.34 (m, 1H), 7.35-7.36 (m, 1H), 7.44 (s, 1H), 7.67-7.70 (m, 1H).

Example 7

1-[(6-Fluoro-2-methoxyquinoxalin-3-yl)aminocarbonyl]-4-(2-methylphenyl)piperazine (Compound 7)

Ethyl N-(6-fluoro-2-methoxyquinoxalin-3-yl)carbamate and 1-(2-methylphenyl)piperazine were reacted by the same way with the example 1 to obtain the titled compound (yield, 73%). $^1$H NMR (200 MHz, CDCl$_3$): δ 2.35 (s, 3H), 2.98-3.03 (m, 4H), 3.73-3.78 (m, 3H), 4.10-4.14 (m, 4H), 7.02-7.17 (m, 2H), 7.19-7.29 (m, 2H), 7.36 (s, 1H), 7.48-7.60 (m, 1H), 7.67-7.74 (m, 1H).

Example 8

1-[(6-Fluoro-2-methoxyquinoxalin-3-yl)aminocarbonyl]-4-(3-methylphenyl)piperazine (Compound 8)

Ethyl N-(6-fluoro-2-methoxyquinoxalin-3-yl)carbamate and 1-(3-methylphenyl)piperazine were reacted by the same way with the example 1 to obtain the titled compound (yield, 90%). $^1$H NMR (200 MHz, CDCl$_3$): δ 2.33 (s, 3H), 3.26-3.30 (m, 4H), 3.74-3.78 (m, 3H), 4.13 (s, 4H), 6.75-6.78 (m, 3H), 7.14-7.28 (m, 2H), 7.36 (s, 1H), 7.44-7.51 (dd, J=9.8 and 2.4 Hz, 1H), 7.67-7.74 (m, 1H).

Example 9

1-[(6-Fluoro-2-methoxyquinoxalin-3-yl)aminocarbonyl]-4-(2,6-dimethylphenyl)piperazine (Compound 9)

Ethyl N-(6-fluoro-2-methoxyquinoxalin-3-yl)carbamate and 1-(2,6-dimethylphenyl)piperazine were reacted by the same way with the example 1 to obtain the titled compound (yield, 65%). $^1$H NMR (300 MHz, CDCl$_3$): δ 2.26 (s, 3H), 3.20 (s, 4H), 3.71 (s, 3H), 4.12-4.18 (m, 4H), 6.99-7.01 (m, 3H), 7.26-7.32 (m, 2H), 7.53-7.81 (m, 2H).

Example 10

1-[(6-Fluoro-2-methoxyquinoxalin-3-yl)aminocarbonyl]-4-(3,5-dimethylphenyl)piperazine (Compound 10)

Ethyl N-(6-fluoro-2-methoxyquinoxalin-3-yl)carbamate and 1-(3,5-dimethylphenyl)piperazine were reacted by the same way with the example 1 to obtain the titled compound (yield, 79%). $^1$H NMR (300 MHz, CDCl$_3$): δ 2.29 (s, 6H), 3.27 (s, 4H), 3.88 (s, 3H), 4.14 (s, 4H), 6.59 (s, 3H), 7.01-7.10 (s, 1H), 7.24-7.36 (m, 2H), 7.47-7.71 (m, 2H).

Example 11

1-[(6-Fluoro-2-methoxyquinoxalin-3-yl)aminocarbonyl]-4-(3-trifluorotolyl)piperazine (Compound 11)

Ethyl N-(6-fluoro-2-methoxyquinoxalin-3-yl)carbamate and 1-(3-trifluorotolyl)piperazine were reacted by the same way with the example 1 to obtain the titled compound (yield, 80%). $^1$H NMR (200 MHz, CDCl$_3$): δ 3.34 (s, 4H), 3.79 (s, 3H), 4.10 (s, 4H), 7.07-7.24 (m, 3H), 7.35-7.43 (m, 3H), 7.71 (m, 1H).

Example 12

1-[(6-Fluoro-2-methoxyquinoxalin-3-yl)aminocarbonyl]-4-(2-fluorophenyl)piperazine (Compound 12)

Ethyl N-(6-fluoro-2-methoxyquinoxalin-3-yl)carbamate and 1-(2-fluorophenyl)piperazine were reacted by the same way with the example 1 to obtain the titled compound (yield, 91%). $^1$H NMR (200 MHz, CDCl$_3$): δ 3.18 (s, 4H), 3.78 (s, 3H), 4.13 (s, 4H), 6.93-7.10 (m, 5H), 7.20-7.34 (m, 1H), 7.46-7.60 (m, 1H), 7.67-7.74 (m, 1H).

Example 13

1-[(6-Fluoro-2-methoxyquinoxalin-3-yl)aminocarbonyl]-4-(4-fluorophenyl)piperazine (Compound 13)

Ethyl N-(6-fluoro-2-methoxyquinoxalin-3-yl)carbamate and 1-(4-fluorophenyl)piperazine were reacted by the same way with the example 1 to obtain the titled compound (yield, 85%). $^1$H NMR (300 MHz, CDCl$_3$): δ 3.19 (s, 4H), 3.77 (s, 3H), 4.13 (s, 4H), 6.88-7.02 (m, 4H), 7.23-7.27 (m, 1H), 7.45-7.71 (m, 3H).

Example 14

1-[(6-Fluoro-2-methoxyquinoxalin-3-yl)aminocarbonyl]-4-(2-chlorophenyl)piperazine (Compound 14)

Ethyl N-(6-fluoro-2-methoxyquinoxalin-3-yl)carbamate and 1-(2-chlorophenyl)piperazine were reacted by the same way with the example 1 to obtain the titled compound (yield, 87%). $^1$H NMR (200 MHz, CDCl$_3$): δ 3.14 (s, 4H), 3.79 (s, 3H), 4.13 (s, 4H), 6.97-7.05 (m, 2H), 7.22-7.28 (m, 2H), 7.33-7.40 (m, 2H), 7.46-7.51 (d, J=10.2 Hz, 1H), 7.66-7.73 (m, 1H).

Example 15

1-[(6-Fluoro-2-methoxyquinoxalin-3-yl)aminocarbonyl]-4-(3-chlorophenyl)piperazine (Compound 15)

Ethyl N-(6-fluoro-2-methoxyquinoxalin-3-yl)carbamate and 1-(3-chlorophenyl)piperazine were reacted by the same way with the example 1 to obtain the titled compound (yield, 70%). $^1$H NMR (200 MHz, CDCl$_3$): δ 3.30 (s, 4H), 3.76 (s, 3H), 4.13 (s, 4H), 6.77-6.91 (m, 3H), 7.15-7.33 (m, 3H), 7.44-7.58 (d, J=10.0 Hz, 1H), 7.58-7.75 (m, 1H).

Example 16

1-[(6-Fluoro-2-methoxyquinoxalin-3-yl)aminocarbonyl]-4-(4-chlorophenyl)piperazine (Compound 16)

Ethyl N-(6-fluoro-2-methoxyquinoxalin-3-yl)carbamate and 1-(4-chlorophenyl)piperazine were reacted by the same way with the example 1 to obtain the titled compound (yield, 95%). $^1$H NMR (300 MHz, CDCl$_3$): δ 3.25 (s, 4H), 3.78 (s, 3H), 4.13 (s, 4H), 6.86 (d, J=8.4 Hz, 2H), 7.22-7.26 (m, 3H), 7.44 (m, 1H), 7.70 (m, 1H).

Example 17

1-[(6-Fluoro-2-methoxyquinoxalin-3-yl)aminocarbonyl]-4-(2-cyanophenyl)piperazine (Compound 17)

Ethyl N-(6-fluoro-2-methoxyquinoxalin-3-yl)carbamate and 1-(2-cyanophenyl)piperazine were reacted by the same way with the example 1 to obtain the titled compound (yield, 85%). $^1$H NMR (200 MHz, CDCl$_3$): δ 3.31 (s, 4H), 3.73-3.85 (m, 3H), 4.06-4.16 (m, 4H), 7.03-7.11 (m, 3H), 7.20-7.34 (m, 1H), 7.50-7.62 (m, 3H), 7.67-7.74 (m, 1H).

Example 18

1-[(6-Fluoro-2-methoxyquinoxalin-3-yl)aminocarbonyl]-4-(4-acetylphenyl)piperazine (Compound 18)

Ethyl N-(6-fluoro-2-methoxyquinoxalin-3-yl)carbamate and 1-(4-acetylphenyl)piperazine were reacted by the same way with the example 1 to obtain the titled compound (yield, 90%). $^1$H NMR (200 MHz, CDCl$_3$): δ 2.54 (s, 3H), 3.42-3.48 (m, 4H), 3.79 (s, 3H), 4.14 (s, 4H), 6.89 (d, J=9.0 Hz, 2H), 7.10-7.50 (m, 3H), 7.69-7.80 (m, 1H), 7.91 (d, J=7.8 Hz, 2H).

Example 19

1-[(6-Fluoro-2-methoxyquinoxalin-3-yl)aminocarbonyl]-4-(4-nitrophenyl)piperazine (Compound 19)

Ethyl N-(6-fluoro-2-methoxyquinoxalin-3-yl)carbamate and 1-(3-fluorophenyl)piperazine were reacted by the same way with the example 1 to obtain the titled compound (yield, 86%). $^1$H NMR (200 MHz, DMSO-d$_6$): δ 3.18 (s, 4H), 3.62 (s, 3H), 3.99-4.01 (m, 4H), 7.01-7.18 (m, 4H), 7.53-7.57 (m, 1H), 7.70-7.78 (m, 1H), 8.06-8.11 (m, 2H).

Example 20

1-[(6-Fluoro-2-methoxyquinoxalin-3-yl)aminocarbonyl]-4-(2-pyridyl)piperazine (Compound 20)

Ethyl N-(6-fluoro-2-methoxyquinoxalin-3-yl)carbamate and 1-(2-pyridyl)piperazine were reacted by the same way with the example 1 to obtain the titled compound (yield, 79%). $^1$H NMR (200 MHz, CDCl$_3$): δ 3.71 (s, 7H), 4.11 (s, 4H), 6.66 (d, J=9.0 Hz, 2H), 7.10 (m, 1H), 7.22-7.25 (m, 1H), 7.38-7.54 (m, 3H), 7.65-7.68 (m, 1H), 8.19 (d, J=3.8 Hz, 1H).

Example 21

1-[(6-Fluoro-2-methoxyquinoxalin-3-yl)aminocarbonyl]-4-(2-pyrimidyl)piperazine (Compound 21)

Ethyl N-(6-fluoro-2-methoxyquinoxalin-3-yl)carbamate and 1-(2-pyrimidyl)piperazine were reacted by the same way with the example 1 to obtain the titled compound (yield, 71%). $^1$H NMR (200 MHz, CDCl$_3$): δ 3.68 (s, 4H), 3.96 (s, 3H), 4.12 (s, 4H), 6.23 (t, J=4.4 Hz, 1H), 7.02 (s, 1H), 6.89-7.00 (m, 1H), 7.36-7.43 (m, 1H), 7.67 (m, 1H), 8.32 (d, J=4.4 Hz, 2H).

Example 22

1-[(6-Chloro-2-methoxyquinoxalin-3-yl)aminocarbonyl]-4-phenylpiperazine (Compound 22)

a) 3-Amino-6-chloro-2-methoxyquinoxaline

To 3-amino-2,6-dichloroquinoxaline (1.30 g, 6.07 mmol) dissolved in tetrahydrofuran (60 ml), 25 wt % sodium methoxide (13.1 g, 60.7 mmol) in methanol was added at room temperature and stirred further at room temperature for 90 minutes. The resulting mixture was concentrated under the reduced pressure to remove the solvent. The product was extracted with dichloromethane and the organic layer was washed with water and dried over MgSO$_4$. After concentration under the reduced pressure, the crude product was purified by SiO$_2$ column chromatography. Extraction of the residue with a n-hexane:ethyl acetate (2:1) mixture and concentration gave 1.22 g of the titled compound (yield, 96%).

b) Ethyl N-(6-chloro-2-methoxyquinoxalin-3-yl)carbamate

3-Amino-6-chloro-2-methoxyquinoxaline (629 mg, 3.00 mmol) and ethyl chloroformate (391 mg, 3.60 mmol) were dissolved in dichloromethane (50 ml) at room temperature and thereto pyridine (285 mg, 3.60 mmol) was added. The resulting mixture was stirred at room temperature for 10 hours and concentrated under the reduced pressure to remove the solvent, and purified by SiO$_2$ column chromatography. Extraction of the residue with a n-hexane:ethyl acetate (3:1) mixture and concentration gave 803 mg of the titled compound (yield, 95%).

c) 1-[(6-Chloro-2-methoxyquinoxalin-3-yl)aminocarbonyl]-4-phenylpiperazine

Ethyl N-(6-chloro-2-methoxyquinoxalin-3-yl)carbamate (27 mg, 0.10 mmol) and 1-phenylpiperazine (24 mg, 0.15 mmol) were dissolved in tetrahydrofuran (2 ml) at room temperature and thereto DBU (23 mg, 0.15 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (2:1) mixture and concentration gave 36 mg of the titled compound (yield, 91%). $^1$H NMR (300 MHz, CDCl$_3$): δ 3.22-3.30 (m, 4H), 3.75-3.78 (m, 3H), 4.08-4.13 (m, 4H), 6.89-6.96 (m, 3H), 7.19-7.44 (m, 5H), 7.64-7.80 (m, 1H).

Example 23

1-[(6-Chloro-2-methoxyquinoxalin-3-yl)aminocarbonyl]-4-(2-methoxyphenyl)piperazine (Compound 23)

Ethyl N-(6-chloro-2-methoxyquinoxalin-3-yl)carbamate and 1-(2-methoxyphenyl)piperazine were reacted by the same way with the example 22 to obtain the titled compound (yield, 77%). $^1$H NMR (300 MHz, CDCl$_3$): δ 3.10-3.17 (m, 4H), 3.80-3.89 (m, 6H), 4.08-4.15 (m, 4H), 6.88-7.07 (m, 4H), 7.20-7.32 (m, 1H), 7.41-7.44 (m, 1H), 7.50-7.68 (m, 1H), 7.82 (s, 1H).

Example 24

1-[(6-Chloro-2-methoxyquinoxalin-3-yl)aminocarbonyl]-4-(3-methoxyphenyl)piperazine (Compound 24)

Ethyl N-(6-chloro-2-methoxyquinoxalin-3-yl)carbamate and 1-(3-methoxyphenyl)piperazine were reacted by the same way with the example 22 to obtain the titled compound (yield, 70%). $^1$H NMR (300 MHz, CDCl$_3$): δ 3.22-3.30 (m, 4H), 3.76-3.80 (m, 6H), 4.08-4.14 (m, 4H), 6.46-6.57 (m, 3H), 7.20 (t, J=8.1 Hz, 1H), 7.34-7.44 (m, 1H), 7.50-7.67 (m, 1H), 7.80 (s, 1H).

Example 25

1-[(6-Chloro-2-methoxyquinoxalin-3-yl)aminocarbonyl]-4-(4-methoxyphenyl)piperazine (Compound 25)

Ethyl N-(6-chloro-2-methoxyquinoxalin-3-yl)carbamate and 1-(4-methoxyphenyl)piperazine were reacted by the same way with the example 22 to obtain the titled compound (yield, 81%). $^1$H NMR (200 MHz, CDCl$_3$): δ 3.16 (s, 4H), 3.78 (s, 3H), 4.16 (s, 4H), 6.88-6.93 (m, 4H), 7.27-7.80 (m, 4H).

Example 26

1-[(6-Chloro-2-methoxyquinoxalin-3-yl)aminocarbonyl]-4-(3,5-dimethoxyphenyl)piperazine (Compound 26)

Ethyl N-(6-chloro-2-methoxyquinoxalin-3-yl)carbamate and 1-(3,5-dimethoxyphenyl)piperazine were reacted by the same way with the example 22 to obtain the titled compound (yield, 81%). MS (ESI) m/z 458 (M+1).

Example 27

1-[(6-Chloro-2-methoxyquinoxalin-3-yl)aminocarbonyl]-4-(3,4,5-trimethoxyphenyl)piperazine (Compound 27)

Ethyl N-(6-chloro-2-methoxyquinoxalin-3-yl)carbamate and 1-(3,4,5-trimethoxyphenyl)piperazine were reacted by the same way with the example 22 to obtain the titled compound (yield, 84%). $^1$H NMR (300 MHz, CDCl$_3$): 3.17-3.25 (m, 4H), 3.81-3.86 (m, 12H), 4.09-4.16 (m, 4H), 6.21 (s, 2H), 7.21-7.30 (m, 1H), 7.33-7.54 (m, 1H), 7.58-7.69 (m, 1H), 7.81 (s, 1H).

Example 28

1-[(6-Chloro-2-methoxyquinoxalin-3-yl)aminocarbonyl]-4-(2-methylphenyl)piperazine (Compound 28)

Ethyl N-(6-chloro-2-methoxyquinoxalin-3-yl)carbamate and 1-(2-methylphenyl)piperazine were reacted by the same way with the example 22 to obtain the titled compound (yield, 80%). $^1$H NMR (300 MHz, CDCl$_3$): δ 2.35 (s, 3H), 2.95-3.02 (m, 4H), 3.74-3.77 (m, 3H), 4.08-4.14 (m, 4H), 7.01-7.57 (m, 7H), 7.64-7.85 (m, 1H).

Example 29

1-[(6-Chloro-2-methoxyquinoxalin-3-yl)aminocarbonyl]-4-(3-methylphenyl)piperazine (Compound 29)

Ethyl N-(6-chloro-2-methoxyquinoxalin-3-yl)carbamate and 1-(3-methylphenyl)piperazine were reacted by the same way with the example 22 to obtain the titled compound (yield, 90%). $^1$H NMR (300 MHz, CDCl$_3$): δ 3.20-3.30 (m, 4H), 3.74-3.77 (m, 3H), 4.11-4.14 (m, 4H), 6.74-6.77 (m, 3H), 7.16-7.25 (m, 4H), 7.64-7.81 (m, 1H).

Example 30

1-[(6-Chloro-2-methoxyquinoxalin-3-yl)aminocarbonyl]-4-(2,6-dimethylphenyl)piperazine (Compound 30)

Ethyl N-(6-chloro-2-methoxyquinoxalin-3-yl)carbamate and 1-(2,6-dimethylphenyl)piperazine were reacted by the same way with the example 22 to obtain the titled compound (yield, 67%). $^1$H NMR (300 MHz, CDCl$_3$): δ 2.33-2.40 (m, 6H), 3.14-3.22 (m, 4H), 3.69-3.76 (m, 3H), 4.06-4.18 (m, 4H), 6.97-7.04 (m, 3H), 7.20-7.85 (m, 4H).

Example 31

1-[(6-Chloro-2-methoxyquinoxalin-3-yl)aminocarbonyl]-4-(3,5-dimethylphenyl)piperazine (Compound 31)

Ethyl N-(6-chloro-2-methoxyquinoxalin-3-yl)carbamate and 1-(3,5-dimethylphenyl)piperazine were reacted by the same way with the example 22 to obtain the titled compound (yield, 79%). $^1$H NMR (300 MHz, CDCl$_3$): δ 2.29 (s, 6H), 3.19-3.29 (m, 4H), 3.73-3.89 (m, 3H), 4.11-4.14 (m, 4H), 6.58 (s, 3H), 7.19-7.25 (m, 1H), 7.36-7.64 (m, 2H), 7.67-7.81 (m, 1H).

Example 32

1-[(6-Chloro-2-methoxyquinoxalin-3-yl)aminocarbonyl]-4-(3-trifluorotolyl)piperazine (Compound 32)

Ethyl N-(6-chloro-2-methoxyquinoxalin-3-yl)carbamate and 1-(3-trifluorotolyl)piperazine were reacted by the same way with the example 22 to obtain the titled compound (yield, 84%). $^1$H NMR (300 MHz, CDCl$_3$): δ 3.27-3.37 (m, 4H), 3.76-3.80 (m, 3H), 4.12-4.14 (m, 4H), 7.08-7.26 (m, 4H), 7.36-7.45 (m, 3H), 7.64-7.80 (m, 1H).

Example 33

1-[(6-Chloro-2-methoxyquinoxalin-3-yl)aminocarbonyl]-4-(2-fluorophenyl)piperazine (Compound 33)

Ethyl N-(6-chloro-2-methoxyquinoxalin-3-yl)carbamate and 1-(2-fluorophenyl)piperazine were reacted by the same way with the example 22 to obtain the titled compound (yield, 80%). $^1$H NMR (300 MHz, CDCl$_3$): δ 3.12-3.21 (m, 4H), 3.77-3.84 (m, 3H), 4.11-4.15 (m, 4H), 6.95-7.10 (m, 4H), 7.20-7.45 (m, 3H), 7.65-7.82 (m, 1H).

Example 34

1-[(6-Chloro-2-methoxyquinoxalin-3-yl)aminocarbonyl]-4-(4-fluorophenyl)piperazine (Compound 34)

Ethyl N-(6-chloro-2-methoxyquinoxalin-3-yl)carbamate and 1-(4-fluorophenyl)piperazine were reacted by the same way with the example 22 to obtain the titled compound (yield, 77%). $^1$H NMR (300 MHz, CDCl$_3$): δ 3.13-3.20 (m, 4H), 3.77 (s, 3H), 4.14 (s, 4H), 6.88-7.02 (m, 4H), 7.20-7.24 (m, 1H), 7.36-7.44 (m, 1H), 7.50-7.67 (m, 1H), 7.80 (s, 1H).

Example 35

1-[(6-Chloro-2-methoxyquinoxalin-3-yl)aminocarbonyl]-4-(2-chlorophenyl)piperazine (Compound 35)

Ethyl N-(6-chloro-2-methoxyquinoxalin-3-yl)carbamate and 1-(2-chlorophenyl)piperazine were reacted by the same way with the example 22 to obtain the titled compound (yield, 76%). $^1$H NMR (300 MHz, CDCl$_3$): δ 3.08-3.17 (m, 4H), 3.78-3.86 (m, 3H), 4.09-4.15 (m, 4H), 7.00-7.07 (m, 2H), 7.20-7.45 (m, 5H), 7.65-7.84 (m, 1H).

Example 36

1-[(6-Chloro-2-methoxyquinoxalin-3-yl)aminocarbonyl]-4-(3-chlorophenyl)piperazine (Compound 36)

Ethyl N-(6-chloro-2-methoxyquinoxalin-3-yl)carbamate and 1-(3-chlorophenyl)piperazine were reacted by the same way with the example 22 to obtain the titled compound (yield, 85%). $^1$H NMR (300 MHz, CDCl$_3$): δ 3.22-3.32 (m, 4H), 3.73-3.77 (m, 3H), 4.11-4.14 (m, 4H), 6.78-6.90 (m, 3H), 7.19-7.44 (m, 4H), 7.64-7.80 (m, 1H).

Example 37

1-[(6-Chloro-2-methoxyquinoxalin-3-yl)aminocarbonyl]-4-(4-chlorophenyl)piperazine (Compound 37)

Ethyl N-(6-chloro-2-methoxyquinoxalin-3-yl)carbamate and 1-(4-chlorophenyl)piperazine were reacted by the same way with the example 22 to obtain the titled compound (yield, 96%). $^1$H NMR (300 MHz, CDCl$_3$): δ 3.18-3.26 (m, 4H), 3.76 (s, 3H), 4.11-4.14 (m, 4H), 6.84-6.87 (d, J=8.7 Hz, 2H), 7.22-7.34 (m, 3H), 7.41-7.53 (m, 1H), 7.65-7.66 (m, 1H), 7.79 (s, 1H).

Example 38

1-[(6-Chloro-2-methoxyquinoxalin-3-yl)aminocarbonyl]-4-(2-cyanophenyl)piperazine (Compound 38)

Ethyl N-(6-chloro-2-methoxyquinoxalin-3-yl)carbamate and 1-(2-cyanophenyl)piperazine were reacted by the same way with the example 22 to obtain the titled compound (yield, 91%). $^1$H NMR (300 MHz, CDCl$_3$): δ 3.25-3.32 (m, 4H), 3.84 (s, 3H), 4.08-4.15 (m, 4H), 7.06-7.08 (m, 2H), 7.21 (m, 1H), 7.41-7.67 (m, 4H), 7.82 (s, 1H).

Example 39

1-[(6-Chloro-2-methoxyquinoxalin-3-yl)aminocarbonyl]-4-(4-acetylphenyl)piperazine (Compound 39)

Ethyl N-(6-chloro-2-methoxyquinoxalin-3-yl)carbamate and 1-(4-acetylphenyl)piperazine were reacted by the same way with the example 22 to obtain the titled compound (yield, 85%). $^1$H NMR (300 MHz, CDCl$_3$): δ 2.54 (s, 3H), 3.50 (s, 4H), 3.80 (s, 3H), 4.14 (s, 4H), 6.89 (d, J=7.7 Hz, 2H), 7.44 (s, 1H), 7.66 (s, 1H), 7.79 (s, 1H), 7.79 (s, 1H), 7.91 (d, J=7.7 Hz, 2H).

Example 40

1-[(6-Chloro-2-methoxyquinoxalin-3-yl)aminocarbonyl]-4-(4-nitrophenyl)piperazine (Compound 40)

Ethyl N-(6-chloro-2-methoxyquinoxalin-3-yl)carbamate and 1-(4-nitrophenyl)piperazine were reacted by the same way with the example 22 to obtain the titled compound (yield, 82%). $^1$H NMR (300 MHz, DMSO-d$_6$): δ 3.62-3.66 (m, 8H), 4.06 (s, 3H), 7.07 (d, J=9.0 Hz, 2H), 7.58 (d, J=8.4 Hz, 1H), 7.76-7.80 (m, 2H), 8.11 (d, J=9.0 Hz, 2H), 9.46 (s, 1H).

Example 41

1-[(6-Chloro-2-methoxyquinoxalin-3-yl)aminocarbonyl]-4-(2-pyridyl)piperazine (Compound 41)

Ethyl N-(6-chloro-2-methoxyquinoxalin-3-yl)carbamate and 1-(2-pyridyl)piperazine were reacted by the same way with the example 22 to obtain the titled compound (yield, 70%), $^1$H NMR (300 MHz, CDCl$_3$): δ 3.63-3.73 (m, 7H), 4.08-4.15 (m, 4H), 6.68 (d, J=8.7 Hz, 2H), 7.20-7.31 (m, 1H), 7.42-7.53 (m, 2H), 7.65-7.80 (m, 2H), 8.21 (d, J=3.6 Hz, 1H).

Example 42

1-[(6-Chloro-2-methoxyquinoxalin-3-yl)aminocarbonyl]-4-(2-pyrimidyl)piperazine (Compound 42)

Ethyl N-(6-chloro-2-methoxyquinoxalin-3-yl)carbamate and 1-(2-pyrimidyl)piperazine were reacted by the same way with the example 22 to obtain the titled compound (yield, 90%). $^1$H NMR (300 MHz, CDCl$_3$): δ 3.71 (s, 4H), 3.99 (s, 3H), 4.15 (s, 4H), 6.55 (s, 1H), 7.27-7.43 (m, 2H), 7.66 (s, 1H), 7.80 (s, 1H), 8.35 (s, 2H).

Example 43

1-[(2-Methoxy-6-methylquinoxalin-3-yl)aminocarbonyl]-4-phenylpiperazine (Compound 43)

a) 3-Amino-2-methoxy-6-methylquinoxaline

To 3-amino-2-chloro-6-methylquinoxaline (550 mg, 2.84 mmol) dissolved in tetrahydrofuran (30 ml), 25 wt % sodium methoxide (6.14 g, 28.4 mmol) in methanol was added at room temperature and stirred further at room temperature for 60 minutes. The resulting mixture was concentrated under the reduced pressure to remove the solvent. The product was extracted with dichloromethane and the organic layer was washed with water and dried over MgSO$_4$. After concentration under the reduced pressure, the crude product was purified by SiO$_2$ column chromatography. Extraction of the residue with n-hexane:ethyl acetate (2:1) mixture and concentration gave 467 mg of the titled compound (yield, 87%).

b) Ethyl N-(2-methoxy-6-methylquinoxalin-3-yl)carbamate

3-Amino-2-methoxy-6-methylquinoxaline (568 mg, 3.00 mmol) and ethyl chloroformate (391 mg, 3.60 mmol) were dissolved in dichloromethane (50 ml) at room temperature and thereto pyridine (285 mg, 3.60 mmol) was added. The resulting mixture was stirred at room temperature for 10 hours and concentrated under the reduced pressure to remove the solvent, and purified by SiO$_2$ column chromatography. Extraction of the residue with n-hexane:ethyl acetate (3:1) mixture and concentration gave 768 mg of the titled compound (yield, 98%).

c) 1-[(2-Methoxy-6-methylquinoxalin-3-yl)aminocarbonyl]-4-phenylpiperazine

Ethyl N-(2-methoxy-6-methylquinoxalin-3-yl)carbamate (26 mg, 0.10 mmol) and 1-phenylpiperazine (24 mg, 0.15 mmol) were dissolved in tetrahydrofuran (2 ml) at room temperature and thereto DBU (23 mg, 0.15 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (2:1) mixture and concentration gave 34 mg of the titled compound (yield, 90%). $^1$H NMR (300 MHz, CDCl$_3$): δ 2.42-2.48 (m, 3H), 3.22-3.30 (m, 4H), 3.77 (s, 3H), 4.12 (s, 4H), 6.90-7.12 (m, 4H), 7.25-7.32 (m, 3H), 7.48-7.65 (m, 2H).

Example 44

1-[(2-Methoxy-6-methylquinoxalin-3-yl)aminocarbonyl]-4-(2-methoxyphenyl)piperazine (Compound 44)

Ethyl N-(2-methoxy-6-methylquinoxalin-3-yl)carbamate and 1-(2-methoxyphenyl)piperazine were reacted by the same way with the example 43 to obtain the titled compound (yield, 66%). $^1$H NMR (300 MHz, CDCl$_3$): δ 2.42-2.49 (m, 3H), 3.10-3.16 (m, 4H), 3.80-3.89 (m, 6H), 4.08-4.17 (m, 4H), 6.88-7.11 (m, 5H), 7.26-7.32 (m, 1H), 7.48-7.64 (m, 2H).

Example 45

1-[(2-Methoxy-6-methylquinoxalin-3-yl)aminocarbonyl]-4-(3-methoxyphenyl)piperazine (Compound 45)

Ethyl N-(2-methoxy-6-methylquinoxalin-3-yl)carbamate and 1-(3-methoxyphenyl)piperazine were reacted by the same way with the example 43 to obtain the titled compound (yield, 73%). $^1$H NMR (300 MHz, CDCl$_3$): δ 2.43-2.48 (m, 3H), 3.23-3.30 (m, 4H), 3.76-3.87 (m, 3H), 4.04-4.13 (m, 4H), 6.45-6.50 (m, 2H), 6.57 (d, J=8.4 Hz, 1H), 7.01-7.12 (m, 1H), 7.17-7.33 (m, 3H), 7.48-7.65 (m, 2H).

Example 46

1-[(2-Methoxy-6-methylquinoxalin-3-yl)aminocarbonyl]-4-(4-methoxyphenyl)piperazine (Compound 46)

Ethyl N-(2-methoxy-6-methylquinoxalin-3-yl)carbamate and 1-(4-methoxyphenyl)piperazine were reacted by the same way with the example 43 to obtain the titled compound (yield, 80%). $^1$H NMR (200 MHz, CDCl$_3$): δ 2.48 (s, 3H), 3.16-3.14 (m, 4H), 3.78-3.82 (m, 6H), 4.13 (s, 4H), 6.84-7.02 (m, 4H), 7.14-7.33 (m, 3H), 7.53-7.64 (m, 1H).

Example 47

1-[(2-Methoxy-6-methylquinoxalin-3-yl)aminocarbonyl]-4-(3,5-dimethoxyphenyl)piperazine (Compound 47)

Ethyl N-(2-methoxy-6-methylquinoxalin-3-yl)carbamate and 1-(3,5-dimethoxyphenyl)piperazine were reacted by the same way with the example 43 to obtain the titled compound (yield, 94%). MS (ESI) m/z 438 (M+1).

Example 48

1-[(2-Methoxy-6-methylquinoxalin-3-yl)aminocarbonyl]-4-(3,4,5-trimethoxyphenyl)piperazine (Compound 48)

Ethyl N-(2-methoxy-6-methylquinoxalin-3-yl)carbamate and 1-(3,4,5-trimethoxyphenyl)piperazine were reacted by the same way with the example 43 to obtain the titled compound (yield, 94%). $^1$H NMR (300 MHz, CDCl$_3$): δ 2.44-2.49 (m, 3H), 3.18-3.25 (m, 4H), 3.80-3.86 (m, 12H), 4.04-4.13 (m, 4H), 6.20 (s, 2H), 7.02-7.20 (m, 1H), 7.31-7.40 (m, 1H), 7.46-7.63 (m, 2H).

Example 49

1-[(2-Methoxy-6-methylquinoxalin-3-yl)aminocarbonyl]-4-(2-methylphenyl)piperazine (Compound 49)

Ethyl N-(2-methoxy-6-methylquinoxalin-3-yl)carbamate and 1-(2-methylphenyl)piperazine were reacted by the same way with the example 43 to obtain the titled compound (yield, 95%). $^1$H NMR (300 MHz, CDCl$_3$): δ 2.32-2.56 (m, 6H), 2.88-3.00 (m, 4H), 3.77 (s, 3H), 4.08-4.13 (m, 4H), 7.02-7.04 (m, 3H), 7.19-7.39 (m, 3H), 7.51-7.65 (m, 2H).

Example 50

1-[(2-Methoxy-6-methylquinoxalin-3-yl)aminocarbonyl]-4-(3-methylphenyl)piperazine (Compound 50)

Ethyl N-(2-methoxy-6-methylquinoxalin-3-yl)carbamate and 1-(3-methylphenyl)piperazine were reacted by the same way with the example 43 to obtain the titled compound (yield, 90%). $^1$H NMR (300 MHz, CDCl$_3$): δ 2.33-2.46 (m, 6H), 3.14-3.37 (m, 4H), 3.73-3.87 (m, 3H), 4.05-4.18 (m, 4H), 6.72-6.78 (m, 3H), 7.00-7.20 (m, 2H), 7.30-7.38 (m, 1H), 7.49-7.62 (m, 2H).

Example 51

1-[(2-Methoxy-6-methylquinoxalin-3-yl)aminocarbonyl]-4-(2,6-dimethylphenyl)piperazine (Compound 51)

Ethyl N-(2-methoxy-6-methylquinoxalin-3-yl)carbamate and 1-(2,6-dimethylphenyl)piperazine were reacted by the same way with the example 43 to obtain the titled compound (yield, 88%). $^1$H NMR (300 MHz, CDCl$_3$): δ 2.04-2.58 (m, 9H), 3.14-3.20 (m, 4H), 3.71-3.76 (m, 3H), 4.07-4.14 (m, 4H), 7.00-7.15 (m, 4H), 7.25-7.76 (m, 3H).

Example 52

1-[(2-Methoxy-6-methylquinoxalin-3-yl)aminocarbonyl]-4-(3,5-dimethylphenyl)piperazine (Compound 52)

Ethyl N-(2-methoxy-6-methylquinoxalin-3-yl)carbamate and 1-(3,5-dimethylphenyl)piperazine were reacted by the same way with the example 43 to obtain the titled compound (yield, 87%). $^1$H NMR (300 MHz, CDCl$_3$): δ 2.29 (s, 6H), 2.42-2.48 (m, 3H), 3.20-3.28 (m, 4H), 3.75-3.80 (m, 3H), 4.10-4.13 (m, 4H), 6.59 (s, 3H), 7.00-7.12 (m, 1H), 7.31 (d, J=8.4 Hz, 1H), 7.48-7.65 (m, 2H).

Example 53

1-[(2-Methoxy-6-methylquinoxalin-3-yl)aminocarbonyl]-4-(3-trifluorotolyl)piperazine (Compound 53)

Ethyl N-(2-methoxy-6-methylquinoxalin-3-yl)carbamate and 1-(3-trifluorotolyl)piperazine were reacted by the same way with the example 43 to obtain the titled compound (yield, 82%). $^1$H NMR (300 MHz, CDCl$_3$): δ 2.46-2.49 (m, 3H), 3.18-3.31 (m, 4H), 3.73-3.80 (m, 3H), 4.10-4.19 (m, 4H), 7.10-7.20 (m, 4H), 7.34-7.39 (m, 2H), 7.56-7.65 (m, 2H).

Example 54

1-[(2-Methoxy-6-methylquinoxalin-3-yl)aminocarbonyl]-4-(2-fluorophenyl)piperazine (Compound 54)

Ethyl N-(2-methoxy-6-methylquinoxalin-3-yl)carbamate and 1-(2-fluorophenyl)piperazine were reacted by the same way with the example 43 to obtain the titled compound (yield, 79%). $^1$H NMR (300 MHz, CDCl$_3$): δ 2.42-2.49 (m, 3H), 3.12-3.19 (m, 4H), 3.79 (s, 3H), 4.11-4.13 (m, 4H), 6.97-7.12 (m, 5H), 7.26-7.33 (m, 1H), 7.48-7.63 (m, 2H).

Example 55

1-[(2-Methoxy-6-methylquinoxalin-3-yl)aminocarbonyl]-4-(4-fluorophenyl)piperazine (Compound 55)

Ethyl N-(2-methoxy-6-methylquinoxalin-3-yl)carbamate and 1-(4-fluorophenyl)piperazine were reacted by the same way with the example 43 to obtain the titled compound (yield, 70%). $^1$H NMR (300 MHz, CDCl$_3$): δ 2.43-2.49 (m, 3H), 3.13-3.21 (m, 4H), 3.77 (s, 3H), 4.11-4.13 (m, 4H), 6.88-6.99 (m, 4H), 7.13 (m, 1H), 7.25 (m, 1H), 7.48-7.65 (m, 2H).

Example 56

1-[(2-Methoxy-6-methylquinoxalin-3-yl)aminocarbonyl]-4-(2-chlorophenyl)piperazine (Compound 56)

Ethyl N-(2-methoxy-6-methylquinoxalin-3-yl)carbamate and 1-(2-chlorophenyl)piperazine were reacted by the same way with the example 43 to obtain the titled compound (yield, 66%). $^1$H NMR (300 MHz, CDCl$_3$): δ 2.43-2.49 (m, 3H), 3.10-3.15 (m, 4H), 3.81 (s, 3H), 3.08-4.12 (m, 4H), 7.00-7.12 (m, 3H), 7.24-7.40 (m, 3H), 7.49-7.65 (m, 2H).

Example 57

1-[(2-Methoxy-6-methylquinoxalin-3-yl)aminocarbonyl]-4-(3-chlorophenyl)piperazine (Compound 57)

Ethyl N-(2-methoxy-6-methylquinoxalin-3-yl)carbamate and 1-(3-chlorophenyl)piperazine were reacted by the same way with the example 43 to obtain the titled compound (yield, 72%). $^1$H NMR (300 MHz, CDCl$_3$): δ 2.45 (s, 3H), 3.26 (s, 4H), 3.77 (s, 3H), 4.08-4.18 (m, 4H), 6.78-6.90 (m, 3H), 7.15-7.38 (m, 3H), 7.56-7.64 (m, 2H).

Example 58

1-[(2-Methoxy-6-methylquinoxalin-3-yl)aminocarbonyl]-4-(4-chlorophenyl)piperazine (Compound 58)

Ethyl N-(2-methoxy-6-methylquinoxalin-3-yl)carbamate and 1-(4-chlorophenyl)piperazine were reacted by the same way with the example 43 to obtain the titled compound (yield, 78%). $^1$H NMR (300 MHz, CDCl$_3$): δ 2.44-2.47 (m, 3H), 3.19-3.26 (m, 4H), 3.78 (s, 3H), 4.12 (s, 4H), 6.87 (d, J=8.9 Hz, 2H), 7.01-7.11 (m, 1H), 7.22-7.26 (m, 3H), 7.52-7.61 (m, 2H).

Example 59

1-[(2-Methoxy-6-methylquinoxalin-3-yl)aminocarbonyl]-4-(2-cyanophenyl)piperazine (Compound 59)

Ethyl N-(2-methoxy-6-methylquinoxalin-3-yl)carbamate and 1-(2-cyanophenyl)piperazine were reacted by the same way with the example 43 to obtain the titled compound (yield, 91%). $^1$H NMR (300 MHz, CDCl$_3$): δ 2.46 (s, 3H), 3.28 (s, 4H), 3.86 (s, 3H), 4.08-4.19 (m, 4H), 7.01-7.08 (m, 3H), 7.17-7.37 (m, 1H), 7.49-7.61 (m, 4H).

Example 60

1-[(2-Methoxy-6-methylquinoxalin-3-yl)aminocarbonyl]-4-(4-acetylphenyl)piperazine (Compound 60)

Ethyl N-(2-methoxy-6-methylquinoxalin-3-yl)carbamate and 1-(4-acetylphenyl)piperazine were reacted by the same way with the example 43 to obtain the titled compound (yield, 87%). $^1$H NMR (300 MHz, CDCl$_3$): δ 2.45-2.53 (m, 6H), 3.47 (s, 4H), 3.81 (s, 3H), 3.87-4.13 (m, 4H), 6.88 (d, J=8.7 Hz, 2H), 7.22-7.36 (m, 2H), 7.56-7.76 (m, 2H), 7.90 (d, J=8.7 Hz, 2H).

Example 61

1-[(2-Methoxy-6-methylquinoxalin-3-yl)aminocarbonyl]-4-(4-nitrophenyl)piperazine (Compound 61)

Ethyl N-(2-methoxy-6-methylquinoxalin-3-yl)carbamate and 1-(4-nitrophenyl)piperazine were reacted by the same way with the example 43 to obtain the titled compound (yield, 86%). $^1$H NMR (300 MHz, CDCl$_3$): δ 2.46 (s, 3H), 3.52-3.58 (m, 4H), 3.82 (s, 3H), 4.09-4.13 (m, 4H), 6.85 (d, J=9.2 Hz, 2H), 7.03-7.15 (m, 1H), 7.41 (m, 1H), 7.52-7.58 (m, 2H), 8.16 (d, J=9.2 Hz, 2H).

Example 62

1-[(2-Methoxy-6-methylquinoxalin-3-yl)aminocarbonyl]-4-(2-pyridyl)piperazine (Compound 62)

Ethyl N-(2-methoxy-6-methylquinoxalin-3-yl)carbamate and 1-(2-pyridyl)piperazine were reacted by the same way with the example 43 to obtain the titled compound (yield, 83%). $^1$H NMR (300 MHz, CDCl$_3$): δ 2.43-2.47 (m, 3H), 3.63-3.73 (m, 7H), 4.13 (s, 4H), 6.67 (d, J=8.4 Hz, 2H), 7.01-7.12 (m, 1H), 7.30-7.33 (m, 1H), 7.48-7.62 (m, 3H), 8.21 (dd, J=4.8 and 1.5 Hz, 1H).

Example 63

1-[(2-Methoxy-6-methylquinoxalin-3-yl)aminocarbonyl]-4-(2-pyrimidyll)piperazine (Compound 63)

Ethyl N-(2-methoxy-6-methylquinoxalin-3-yl)carbamate and 1-(2-pyrimidyl)piperazine were reacted by the same way with the example 43 to obtain the titled compound (yield, 93%). $^1$H NMR (300 MHz, CDCl$_3$): δ 2.47 (s, 4H), 3.71 (s, 3H), 3.91-3.99 (m, 4H), 4.13 (s, 3H), 6.53 (s, 1H), 7.01-7.13 (m, 1H), 7.27-7.30 (m, 1H), 7.52-7.61 (m, 2H), 8.33 (d, J=4.8 Hz, 2H).

Example 64

1-[(2,6-Dimethoxyquinoxalin-3-yl)aminocarbonyl]-4-phenylpiperazine (Compound 64)

a) 3-Amino-2,6-dimethoxyquinoxaline

To 3-amino-2-chloro-6-methoxyquinoxaline (1.50 g, 7.16 mmol) dissolved in tetrahydrofuran (60 ml), 25 wt % sodium methoxide (15.5 g, 71.6 mmol) in methanol was added at room temperature and stirred further at room temperature for 21 hours. The resulting mixture was concentrated under the reduced pressure to remove the solvent. The product was extracted with dichloromethane and the organic layer was washed with water and dried over MgSO$_4$. After concentration under the reduced pressure, the crude product was purified by SiO$_2$ column chromatography. Extraction of the residue with a n-hexane:ethyl acetate (2:1) mixture and concentration gave 1.18 g of the titled compound (yield, 80%).

b) Ethyl N-(2,6-dimethoxyquinoxalin-3-yl)carbamate

3-Amino-2,6-dimethoxyquinoxaline (616 mg, 3.00 mmol) and ethyl chloroformate (391 mg, 3.60 mmol) were dissolved in dichloromethane (50 ml) at room temperature and thereto pyridine (285 mg, 3.60 mmol) was added. The resulting mixture was stirred at room temperature for 10 hours and concentrated under the reduced pressure to remove the solvent, and purified by SiO$_2$ column chromatography. Extraction of the residue with a n-hexane:ethyl acetate (3:1) mixture and concentration gave 799 mg of the titled compound (yield, 96%).

c) 1-[(2,6-Dimethoxyquinoxalin-3-yl)aminocarbonyl]-4-phenylpiperazine

Ethyl N-(2,6-dimethoxyquinoxalin-3-yl)carbamate (28 mg, 0.10 mmol) and 1-phenylpiperazine (24 mg, 0.15 mmol) were dissolved in tetrahydrofuran (2 ml) at room temperature and thereto DBU (23 mg, 0.15 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (2:1) mixture and concentration gave 36 mg of the titled compound (yield, 92%). $^1$H NMR (300 MHz, CDCl$_3$): δ 3.27 (s, 4H), 3.73-3.86 (m, 6H), 4.08-4.11 (m, 4H), 6.88-7.03 (m, 4H), 7.15 (s, 1H), 7.26-7.33 (m, 3H), 7.57-7.62 (m, 1H).

Example 65

1-[(2,6-Dimethoxyquinoxalin-3-yl)aminocarbonyl]-4-(2-methoxyphenyl)piperazine (Compound 65)

Ethyl N-(2,6-dimethoxyquinoxalin-3-yl)carbamate and 1-(2-methoxyphenyl)piperazine were reacted by the same way with the example 64 to obtain the titled compound (yield, 84%). $^1$H NMR (300 MHz, CDCl$_3$): δ 3.15 (s, 4H), 3.83-3.89 (m, 9H), 4.12-4.17 (m, 4H), 6.88-6.95 (m, 3H), 7.02-7.05 (m, 1H), 7.14 (d, J=8.7 Hz, 1H), 7.31 (s, 1H), 7.51 (d, J=8.7 Hz, 1H), 7.63 (d, J=9.0 Hz, 1H).

Example 66

1-[(2,6-Dimethoxyquinoxalin-3-yl)aminocarbonyl]-4-(3-methoxyphenyl)piperazine (Compound 66)

Ethyl N-(2,6-dimethoxyquinoxalin-3-yl)carbamate and 1-(3-methoxyphenyl)piperazine were reacted by the same way with the example 64 to obtain the titled compound (yield, 80%). $^1$H NMR (300 MHz, CDCl$_3$): δ 3.28 (s, 4H), 3.80-3.87 (m, 9H), 4.11 (s, 4H), 6.45-6.49 (m, 2H), 6.56 (d, J=8.4 Hz, 1H), 6.91 (s, 1H), 7.04-7.36 (m, 3H), 7.53-7.62 (m, 1H).

Example 67

1-[(2,6-Dimethoxyquinoxalin-3-yl)aminocarbonyl]-4-(4-methoxyphenyl)piperazine (Compound 67)

Ethyl N-(2,6-dimethoxyquinoxalin-3-yl)carbamate and 1-(4-methoxyphenyl)piperazine were reacted by the same way with the example 64 to obtain the titled compound (yield, 81%). $^1$H NMR (200 MHz, CDCl$_3$): δ 3.16 (s, 4H), 3.78-3.88 (m, 9H), 4.12-4.17 (m, 4H), 6.84-6.97 (m, 4H), 7.16-7.32 (m, 3H), 7.62-7.66 (m, 1H).

Example 68

1-[(2,6-Dimethoxyquinoxalin-3-yl)aminocarbonyl]-4-(3,5-dimethoxyphenyl)piperazine (Compound 68)

Ethyl N-(2,6-dimethoxyquinoxalin-3-yl)carbamate and 1-(3,5-dimethoxyphenyl)piperazine were reacted by the same way with the example 64 to obtain the titled compound (yield, 81%). MS (ESI) m/z 454 (M+1).

Example 69

1-[(2,6-Dimethoxyquinoxalin-3-yl)aminocarbonyl]-4-(3,4,5-trimethoxyphenyl)piperazine (Compound 69)

Ethyl N-(2,6-dimethoxyquinoxalin-3-yl)carbamate and 1-(3,4,5-trimethoxyphenyl)piperazine were reacted by the same way with the example 64 to obtain the titled compound (yield, 97%). $^1$H NMR (300 MHz, CDCl$_3$): δ 3.55-3.87 (m, 10H), 4.12 (s, 4H), 6.67 (d, J=8.4 Hz, 1H), 7.14 (d, J=9.0 Hz, 1H), 7.25 (s, 1H), 7.34 (s, 1H), 7.51 (t, J=7.2 Hz, 1H), 7.64 (d, J=9.0 Hz, 1H), 8.21 (d, J=3.6 Hz, 1H).

Example 70

1-[(2,6-Dimethoxyquinoxalin-3-yl)aminocarbonyl]-4-(2-methylphenyl)piperazine (Compound 70)

Ethyl N-(2,6-dimethoxyquinoxalin-3-yl)carbamate and 1-(2-methylphenyl)piperazine were reacted by the same way with the example 64 to obtain the titled compound (yield, 90%). $^1$H NMR (300 MHz, CDCl$_3$): δ 2.35 (s, 3H), 2.95-3.02 (m, 4H), 3.75-3.90 (m, 6H), 4.09-4.13 (m, 4H), 6.99-7.31 (m, 7H), 7.50-7.66 (m, 1H).

Example 71

1-[(2,6-Dimethoxyquinoxalin-3-yl)aminocarbonyl]-4-(3-methylphenyl)piperazine (Compound 71)

Ethyl N-(2,6-dimethoxyquinoxalin-3-yl)carbamate and 1-(3-methylphenyl)piperazine were reacted by the same way with the example 64 to obtain the titled compound (yield, 95%). $^1$H NMR (300 MHz, CDCl$_3$): δ 2.33 (s, 3H), 3.26 (s, 4H), 3.72-3.89 (m, 6H), 4.09-4.18 (m, 4H), 6.72-6.78 (m, 4H), 7.03-7.37 (m, 3H), 7.57-7.65 (m, 1H).

Example 72

1-[(2,6-Dimethoxyquinoxalin-3-yl)aminocarbonyl]-4-(2,6-dimethylphenyl)piperazine (Compound 72)

Ethyl N-(2,6-dimethoxyquinoxalin-3-yl)carbamate and 1-(2,6-dimethylphenyl)piperazine were reacted by the same way with the example 64 to obtain the titled compound (yield, 87%). $^1$H NMR (300 MHz, CDCl$_3$): δ 2.33-2.36 (m, 6H), 3.14-3.22 (m, 4H), 3.70-3.90 (m, 6H), 4.09-4.15 (m, 4H), 6.67-7.32 (m, 6H), 7.50-7.65 (m, 1H).

Example 73

1-[(2,6-Dimethoxyquinoxalin-3-yl)aminocarbonyl]-4-(3,5-dimethylphenyl)piperazine (Compound 73)

Ethyl N-(2,6-dimethoxyquinoxalin-3-yl)carbamate and 1-(3,5-dimethylphenyl)piperazine were reacted by the same way with the example 64 to obtain the titled compound (yield, 65%). $^1$H NMR (300 MHz, CDCl$_3$): δ 2.28 (s, 6H), 3.26 (s, 4H), 3.76-3.87 (m, 6H), 4.11 (s, 4H), 6.59 (s, 2H), 6.90 (m, 1H), 7.14 (d, J=8.7 Hz, 1H), 7.32 (s, 1H), 7.51 (d, J=7.5 Hz, 1H), 7.64 (d, J=8.7 Hz, 1H).

Example 74

1-[(2,6-Dimethoxyquinoxalin-3-yl)aminocarbonyl]-4-(3-trifluorotolyl)piperazine (Compound 74)

Ethyl N-(2,6-dimethoxyquinoxalin-3-yl)carbamate and 1-(3-trifluorotolyl)piperazine were reacted by the same way with the example 64 to obtain the titled compound (yield, 77%). $^1$H NMR (300 MHz, CDCl$_3$): δ 3.33 (s, 4H), 3.74-3.90 (m, 6H), 4.09-4.19 (m, 4H), 6.92 (s, 1H), 7.02-7.19 (m, 5H), 7.38 (t, J=7.5 Hz, 1H), 7.59-7.66 (m, 1H).

Example 75

1-[(2,6-Dimethoxyquinoxalin-3-yl)aminocarbonyl]-4-(2-fluorophenyl)piperazine (Compound 75)

Ethyl N-(2,6-dimethoxyquinoxalin-3-yl)carbamate and 1-(2-fluorophenyl)piperazine were reacted by the same way with the example 64 to obtain the titled compound (yield, 72%). $^1$H NMR (300 MHz, CDCl$_3$): δ 3.18 (s, 4H), 3.73-3.88 (m, 6H), 4.11-4.15 (m, 4H), 6.88-7.15 (m, 5H), 7.33 (s, 1H), 7.51 (d, J=8.7 Hz, 1H), 7.64 (d, J=9.0 Hz, 1H).

Example 76

1-[(2,6-Dimethoxyquinoxalin-3-yl)aminocarbonyl]-4-(4-fluorophenyl)piperazine (Compound 76)

Ethyl N-(2,6-dimethoxyquinoxalin-3-yl)carbamate and 1-(4-fluorophenyl)piperazine were reacted by the same way with the example 64 to obtain the titled compound (yield, 90%). $^1$H NMR (300 MHz, CDCl$_3$): δ 3.17 (s, 4H), 3.78-3.89 (m, 6H), 4.11-4.15 (m, 4H), 6.88-7.02 (m, 4H), 7.14-7.36 (m, 3H), 7.58-7.62 (m, 1H).

Example 77

1-[(2,6-Dimethoxyquinoxalin-3-yl)aminocarbonyl]-4-(2-chlorophenyl)piperazine (Compound 77)

Ethyl N-(2,6-dimethoxyquinoxalin-3-yl)carbamate and 1-(2-chlorophenyl)piperazine were reacted by the same way with the example 64 to obtain the titled compound (yield, 89%). $^1$H NMR (300 MHz, CDCl$_3$): δ 3.09-3.16 (m, 4H), 3.79-3.90 (m, 6H), 4.10-4.16 (m, 4H), 7.00-7.30 (m, 7H), 7.38-7.66 (m, 1H).

Example 78

1-[(2,6-Dimethoxyquinoxalin-3-yl)aminocarbonyl]-4-(3-chlorophenyl)piperazine (Compound 78)

Ethyl N-(2,6-dimethoxyquinoxalin-3-yl)carbamate and 1-(3-chlorophenyl)piperazine were reacted by the same way with the example 64 to obtain the titled compound (yield, 85%). $^1$H NMR (300 MHz, CDCl$_3$): δ 3.21-3.32 (m, 4H), 3.75-3.88 (m, 6H), 4.10-4.13 (m, 4H), 6.80-6.90 (m, 4H), 7.14-7.29 (m, 3H), 7.63-7.66 (m, 1H).

Example 79

1-[(2,6-Dimethoxyquinoxalin-3-yl)aminocarbonyl]-4-(4-chlorophenyl)piperazine (Compound 79)

Ethyl N-(2,6-dimethoxyquinoxalin-3-yl)carbamate and 1-(4-chlorophenyl)piperazine were reacted by the same way with the example 64 to obtain the titled compound (yield, 86%). $^1$H NMR (300 MHz, CDCl$_3$): δ 3.25 (s, 4H), 3.77 (s, 3H), 3.87 (s, 3H), 4.09-4.12 (m, 4H), 6.86-7.00 (m, 3H), 7.12-7.24 (m, 3H), 7.55-7.65 (m, 2H).

Example 80

1-[(2,6-Dimethoxyquinoxalin-3-yl)aminocarbonyl]-4-(2-cyanophenyl)piperazine (Compound 80)

Ethyl N-(2,6-dimethoxyquinoxalin-3-yl)carbamate and 1-(2-cyanophenyl)piperazine were reacted by the same way with the example 64 to obtain the titled compound (yield, 94%). $^1$H NMR (200 MHz, CDCl$_3$): δ 3.30 (s, 4H), 3.88-3.90 (m, 6H), 4.07-4.20 (m, 4H), 6.94-7.07 (m, 3H), 7.27-7.34 (m, 2H), 7.53-7.63 (m, 3H).

Example 81

1-[(2,6-Dimethoxyquinoxalin-3-yl)aminocarbonyl]-4-(4-acetylphenyl)piperazine (Compound 81)

Ethyl N-(2,6-dimethoxyquinoxalin-3-yl)carbamate and 1-(4-acetylphenyl)piperazine were reacted by the same way with the example 64 to obtain the titled compound (yield, 87%). $^1$H NMR (200 MHz, CDCl$_3$): δ 2.54-2.58 (m, 3H), 3.49-3.67 (m, 4H), 3.87-3.96 (m, 6H), 4.12-4.16 (m, 4H), 6.87-7.03 (m, 2H), 7.19-7.31 (m, 3H), 7.62-7.66 (m, 1H), 7.89-7.97 (m, 2H).

Example 82

1-[(2,6-Dimethoxyquinoxalin-3-yl)aminocarbonyl]-4-(4-nitrophenyl)piperazine (Compound 82)

Ethyl N-(2,6-dimethoxyquinoxalin-3-yl)carbamate and 1-(4-nitrophenyl)piperazine were reacted by the same way with the example 64 to obtain the titled compound (yield, 81%). $^1$H NMR (300 MHz, CDCl$_3$): δ 3.57 (s, 4H), 3.75-3.87 (m, 6H), 4.09-4.16 (m, 4H), 6.84 (d, J=9.3 Hz, 2H), 6.91-7.27 (m, 3H), 7.56-7.63 (m, 1H), 8.16 (d, J=9.3 Hz, 2H).

Example 83

1-[(2,6-Dimethoxyquinoxalin-3-yl)aminocarbonyl]-4-(2-pyridyl)piperazine (Compound 83)

Ethyl N-(2,6-dimethoxyquinoxalin-3-yl)carbamate and 1-(2-pyridyl)piperazine were reacted by the same way with the example 64 to obtain the titled compound (yield, 84%).

$^1$H NMR (300 MHz, CDCl$_1$): δ 3.87 (s, 3H), 3.73-3.88 (m, 6H), 4.11-4.15 (m, 4H), 6.88-7.15 (m, 5H), 7.33 (s, 1H), 7.51 (d, J=8.7 Hz, 1H), 7.64 (d, J=9.0 Hz, 1H).

Example 84

1-[(2,6-Dimethoxyquinoxalin-3-yl)aminocarbonyl]-4-(2-pyrimidyl)piperazine (Compound 84)

Ethyl N-(2,6-dimethoxyquinoxalin-3-yl)carbamate and 1-(2-pyrimidyl)piperazine were reacted by the same way with the example 64 to obtain the titled compound (yield, 80%). $^1$H NMR (300 MHz, CDCl$_3$): δ 3.72 (s, 3H), 3.87-3.96 (m, 7H), 4.12-4.15 (m, 4H), 6.54 (t, J=4.8 Hz, 1H), 6.92 (s, 1H), 7.04-7.36 (m, 3H), 7.62 (m, 1H), 8.34 (d, J=4.8 Hz, 2H).

Example 85

1-[(6-Fluoro-3-methoxyquinoxalin-2-yl)aminocarbonyl]-4-phenylpiperazine (Compound 85)

a) 2-(2,4-Dimethoxybenzylamino)-6-fluoro-3-methoxyquinoxaline

To 2-chloro-6-fluoro-3-methoxyquinoxaline (4.00 g, 18.8 mmol) dissolved in dimethylsulfoxide (40 ml), 2,4-dimethoxybenzylamine (7.86 g, 47.0 mmol) was added at room temperature. The mixture was stirred at room temperature for 24 hours and then water was added thereto. The product was extracted with ethyl acetate and the organic layer was washed with water and dried over MgSO$_4$. After concentration under the reduced pressure, the crude product was purified by SiO$_2$ column chromatography. Extraction of the residue with a n-hexane:ethyl acetate (6:1) mixture and concentration gave 4.45 g of the titled compound (yield, 92%).

b) 2-Amino-6-fluoro-3-methoxyquinoxaline

To 2-(2,4-dimethoxybenzylamino)-6-fluoro-3-methoxyquinoxaline (2.70 g, 7.86 mmol), 60 ml of 50% trifluoroacetic acid in dichloromethane was added at room temperature. The resulting mixture was stirred at room temperature for 24 hours and concentrated under the reduced pressure to remove the solvent. The residue was neutralized with saturated sodium bicarbonate solution and then NaCl solution was added thereto. The product was extracted with dichloromethanee and the organic layer was dried over MgSO$_4$. After concentration under the reduced pressure, the crude product was purified by SiO$_2$ column chromatography. Extraction of the residue with a n-hexane:ethyl acetate (4:1) mixture and concentration gave 1.27 g of the titled compound (yield, 84%).

c) Ethyl N-(6-fluoro-3-methoxyquinoxalin-2-yl)carbamate

2-Amino-6-fluoro-3-methoxyquinoxaline (580 mg, 3.00 mmol) and ethyl chloroformate (391 mg, 3.60 mmol) were dissolved in dichloromethane (50 ml) at room temperature and thereto pyridine (285 mg, 3.60 mmol) was added. The resulting mixture was stirred at room temperature for 10 hours and concentrated under the reduced pressure to remove the solvent, and purified by SiO$_2$ column chromatography. Extraction of the residue with a n-hexane:ethyl acetate (3:1) mixture and concentration gave 756 mg of the titled compound (yield, 95%).

d) 1-[(6-Fluoro-3-methoxyquinoxalin-2-yl)aminocarbonyl]-4-phenylpiperazine

Ethyl N-(6-fluoro-3-methoxyquinoxalin-2-yl)carbamate (27 mg, 0.10 mmol) and 1-phenylpiperazine (24 mg, 0.15 mmol) were dissolved in tetrahydrofuran (2 ml) at room temperature and thereto DBU (23 mg, 0.15 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (2:1) mixture and concentration gave 34 mg of the titled compound (yield, 83%). $^1$H NMR (300 MHz, CDCl$_3$): δ 3.28-3.31 (m, 4H), 3.75-3.78 (m, 4H), 4.15 (s, 4H), 6.90-6.97 (m, 3H), 7.24-7.42 (m, 5H), 7.80 (dd, J=9.0 and 6.0 Hz, 1H).

Example 86

1-[(6-Fluoro-3-methoxyquinoxalin-2-yl)aminocarbonyl]-4-(2-methoxyphenyl)piperazine (Compound 86)

Ethyl N-(6-fluoro-3-methoxyquinoxalin-2-yl)carbamate and 1-(2-methoxyphenyl)piperazine were reacted by the same way with the example 85 to obtain the titled compound (yield, 82%). $^1$H NMR (200 MHz, CDCl$_3$): δ 3.14-3.17 (m, 4H), 3.78-3.81 (m, 4H), 3.88 (s, 3H), 4.14 (s, 3H), 6.88-7.41 (m, 7H), 7.81 (dd, J=9.0 and 5.7 Hz, 1H).

Example 87

1-[(6-Fluoro-3-methoxyquinoxalin-2-yl)aminocarbonyl]-4-(3-methoxyphenyl)piperazine (Compound 87)

Ethyl N-(6-fluoro-3-methoxyquinoxalin-2-yl)carbamate and 1-(3-methoxyphenyl)piperazine were reacted by the same way with the example 85 to obtain the titled compound (yield, 77%). $^1$H NMR (300 MHz, CDCl$_3$): δ 3.28-3.31 (m, 4H), 3.74-3.77 (m, 4H), 3.80 (s, 3H), 4.15 (s, 3H), 6.46-6.58 (m, 2H), 7.18-7.28 (m, 4H), 7.40 (dd, J=9.3 and 2.7 Hz, 1H), 7.78-7.81 (m, 1H).

Example 88

1-[(6-Fluoro-3-methoxyquinoxalin-2-yl)aminocarbonyl]-4-(4-methoxyphenyl)piperazine (Compound 88)

Ethyl N-(6-fluoro-3-methoxyquinoxalin-2-yl)carbamate and 1-(4-methoxyphenyl)piperazine were reacted by the same way with the example 85 to obtain the titled compound (yield, 84%). $^1$H NMR (200 MHz, CDCl$_3$): δ 3.15-3.18 (m, 4H), 3.78 (s, 4H), 4.15 (s, 3H), 6.85-6.96 (m, 4H), 7.22-7.42 (m, 3H), 7.81 (dd, J=9.0 and 6.0 Hz, 1H).

Example 89

1-[(6-Fluoro-3-methoxyquinoxalin-2-yl)aminocarbonyl]-4-(3,5-dimethoxyphenyl)piperazine (Compound 89)

Ethyl N-(6-fluoro-3-methoxyquinoxalin-2-yl)carbamate and 1-(3,5-dimethoxyphenyl)piperazine were reacted by the same way with the example 85 to obtain the titled compound (yield, 76%). MS (ESI) m/z 442 (M+1).

Example 90

1-[(6-Fluoro-3-methoxyquinoxalin-2-yl)aminocarbonyl]-4-(3,4,5-trimethoxyphenyl)piperazine (Compound 90)

Ethyl N-(6-fluoro-3-methoxyquinoxalin-2-yl)carbamate and 1-(3,4,5-trimethoxyphenyl)piperazine were reacted by the same way with the example 85 to obtain the titled compound (yield, 83%).

Example 91

1-[(6-Fluoro-3-methoxyquinoxalin-2-yl)aminocarbonyl]-4-(2-methylphenyl)piperazine (Compound 91)

Ethyl N-(6-fluoro-3-methoxyquinoxalin-2-yl)carbamate and 1-(2-methylphenyl)piperazine were reacted by the same way with the example 85 to obtain the titled compound (yield, 77%). $^1$H NMR (200 MHz, CDCl$_3$): δ 2.95 (s, 3H), 2.99-3.02 (m, 4H), 3.74-3.77 (m, 4H), 4.15 (s, 3H), 7.01-7.05 (m, 2H), 7.17-7.42 (m, 5H), 7.81-7.84 (m, 1H).

Example 92

1-[(6-Fluoro-3-methoxyquinoxalin-2-yl)aminocarbonyl]-4-(3-methylphenyl)piperazine (Compound 92)

Ethyl N-(6-fluoro-3-methoxyquinoxalin-2-yl)carbamate and 1-(3-methylphenyl)piperazine were reacted by the same way with the example 85 to obtain the titled compound (yield, 87%). $^1$H NMR (200 MHz, CDCl$_3$): δ 2.33 (s, 3H), 3.26-3.30 (m, 4H), 3.74-3.77 (m, 4H), 4.15 (s, 3H), 6.74-6.77 (m, 3H), 7.16-7.29 (m, 3H), 7.40 (dd, J=9.6 and 2.7 Hz, 1H), 7.78-7.81 (m, 1H).

Example 93

1-[(6-Fluoro-3-methoxyquinoxalin-2-yl)aminocarbonyl]-4-(2,6-dimethylphenyl)piperazine (Compound 93)

Ethyl N-(6-fluoro-3-methoxyquinoxalin-2-yl)carbamate and 1-(2,6-dimethylphenyl)piperazine were reacted by the same way with the example 85 to obtain the titled compound (yield, 76%). $^1$H NMR (300 MHz, CDCl$_3$): δ 2.36 (s, 6H), 3.18-3.21 (m, 4H), 3.69-3.72 (m, 4H), 4.15 (s, 3H), 6.97-7.04 (m, 3H), 7.22-7.42 (m, 4H), 7.82-7.87 (m, 1H).

Example 94

1-[(6-Fluoro-3-methoxyquinoxalin-2-yl)aminocarbonyl]-4-(3,5-dimethylphenyl)piperazine (Compound 94)

Ethyl N-(6-fluoro-3-methoxyquinoxalin-2-yl)carbamate and 1-(3,5-dimethylphenyl)piperazine were reacted by the same way with the example 85 to obtain the titled compound (yield, 86%). $^1$H NMR (300 MHz, CDCl$_3$): δ 2.29 (s, 6H), 3.25-3.29 (m, 4H), 3.73-3.77 (m, 4H), 4.16 (s, 3H), 6.55-6.59 (m, 3H), 7.21-7.43 (m, 3H), 7.78-7.83 (m, 1H).

Example 95

1-[(6-Fluoro-3-methoxyquinoxalin-2-yl)aminocarbonyl]-4-(3-trifluorotolyl)piperazine (Compound 95)

Ethyl N-(6-fluoro-3-methoxyquinoxalin-2-yl)carbamate and 1-(3-trifluorotolyl)piperazine were reacted by the same way with the example 85 to obtain the titled compound (yield, 85%). $^1$H NMR (200 MHz, CDCl$_3$): δ 3.36 (s, 4H), 3.78 (s, 4H), 4.16 (s, 3H), 7.08-7.41 (m, 7H), 7.79 (t, J=8.4 Hz, 1H).

Example 96

1-[(6-Fluoro-3-methoxyquinoxalin-2-yl)aminocarbonyl]-4-(2-fluorophenyl)piperazine (Compound 96)

Ethyl N-(6-fluoro-3-methoxyquinoxalin-2-yl)carbamate and 1-(2-fluorophenyl)piperazine were reacted by the same way with the example 85 to obtain the titled compound (yield, 85%). $^1$H NMR (200 MHz, CDCl$_3$): δ 3.17-3.20 (m, 4H), 3.77-3.80 (m, 4H), 4.13 (s, 3H), 6.97-7.09 (m, 4H), 7.24-7.41 (m, 3H), 7.81-7.82 (m, 1H).

Example 97

1-[(6-Fluoro-3-methoxyquinoxalin-2-yl)aminocarbonyl]-4-(4-fluorophenyl)piperazine (Compound 97)

Ethyl N-(6-fluoro-3-methoxyquinoxalin-2-yl)carbamate and 1-(4-fluorophenyl)piperazine were reacted by the same way with the example 85 to obtain the titled compound (yield, 82%). $^1$H NMR (300 MHz, CDCl$_3$): δ 3.18-3.21 (m, 4H), 3.74-3.78 (m, 4H), 4.14 (s, 3H), 6.88-6.92 (m, 4H), 7.25-7.42 (m, 3H), 7.76-7.81 (m, 1H).

Example 98

1-[(6-Fluoro-3-methoxyquinoxalin-2-yl)aminocarbonyl]-4-(2-chlorophenyl)piperazine (Compound 98)

Ethyl N-(6-fluoro-3-methoxyquinoxalin-2-yl)carbamate and 1-(2-chlorophenyl)piperazine were reacted by the same way with the example 85 to obtain the titled compound (yield, 87%). $^1$H NMR (200 MHz, CDCl$_3$): δ 3.13-3.16 (m, 4H), 3.78-3.81 (m, 4H), 4.15 (s, 3H), 7.02-7.06 (m, 3H), 7.23-7.42 (m, 4H), 7.82-7.83 (m, 1H).

Example 99

1-[(6-Fluoro-3-methoxyquinoxalin-2-yl)aminocarbonyl]-4-(3-chlorophenyl)piperazine (Compound 99)

Ethyl N-(6-fluoro-3-methoxyquinoxalin-2-yl)carbamate and 1-(3-chlorophenyl)piperazine were reacted by the same way with the example 85 to obtain the titled compound (yield, 82%). $^1$H NMR (200 MHz, CDCl$_3$): δ 3.30 (s, 4H), 3.91 (s, 4H), 4.15 (s, 3H), 6.79-6.91 (m, 3H), 7.17-7.42 (m, 4H), 7.79 (m, 1H).

Example 100

1-[(6-Fluoro-3-methoxyquinoxalin-2-yl)aminocarbonyl]-4-(4-chlorophenyl)piperazine (Compound 100)

Ethyl N-(6-fluoro-3-methoxyquinoxalin-2-yl)carbamate and 1-(4-chlorophenyl)piperazine were reacted by the same way with the example 85 to obtain the titled compound (yield, 86%). $^1$H NMR (300 MHz, CDCl$_3$): δ 3.24-3.27 (m, 4H), 3.74-3.77 (m, 4H), 4.15 (s, 3H), 6.84-6.89 (m, 2H), 7.14-7.43 (m, 5H), 7.77-7.82 (m, 1H).

Example 101

1-[(6-Fluoro-3-methoxyquinoxalin-2-yl)aminocarbonyl]-4-(2-cyanophenyl)piperazine (Compound 101)

Ethyl N-(6-fluoro-3-methoxyquinoxalin-2-yl)carbamate and 1-(2-cyanophenyl)piperazine were reacted by the same way with the example 85 to obtain the titled compound (yield, 88%). $^1$H NMR (200 MHz, CDCl$_3$): δ 3.31 (s, 4H), 3.84 (s, 4H), 4.15 (s, 3H), 7.03-7.10 (m, 2H), 7.25-7.61 (m, 5H), 7.82 (dd, J=8.7 and 5.7 Hz, 1H).

Example 102

1-[(6-Fluoro-3-methoxyquinoxalin-2-yl)aminocarbonyl]-4-(4-acetylphenyl)piperazine (Compound 102)

Ethyl N-(6-fluoro-3-methoxyquinoxalin-2-yl)carbamate and 1-(4-acetylphenyl)piperazine were reacted by the same way with the example 85 to obtain the titled compound (yield, 91%). $^1$H NMR (200 MHz, CDCl$_3$): δ 2.54 (s, 3H), 3.50 (s, 4H), 3.90 (s, 4H), 4.15 (s, 3H), 6.89 (d, J=8.7 Hz, 2H), 7.25-7.62 (m, 3H), 7.79 (s, 1H), 7.91 (d, J=9.0 Hz, 1H).

Example 103

1-[(6-Fluoro-3-methoxyquinoxalin-2-yl)aminocarbonyl]-4-(4-nitrophenyl)piperazine (Compound 103)

Ethyl N-(6-fluoro-3-methoxyquinoxalin-2-yl)carbamate and 1-(4-nitrophenyl)piperazine were reacted by the same way with the example 85 to obtain the titled compound (yield, 89%). $^1$H NMR (200 MHz, DMSO-d$_6$): δ 3.57-3.59 (m, 4H), 3.64-3.66 (m, 4H), 4.04 (s, 3H), 7.05 (d, J=9.5 Hz, 2H), 7.44 (dt, J=8.9 and 2.9 Hz, 1H), 7.54 (dd, J=9.8 and 2.8 Hz, 1H), 7.81 (dd, J=9.1 and 5.9 Hz, 1H), 8.08 (d, J=9.4 Hz, 2H), 9.35 (s, 1H).

Example 104

1-[(6-Fluoro-3-methoxyquinoxalin-2-yl)aminocarbonyl]-4-(2-pyridyl)piperazine (Compound 104)

Ethyl N-(6-fluoro-3-methoxyquinoxalin-2-yl)carbamate and 1-(2-pyridyl)piperazine were reacted by the same way with the example 85 to obtain the titled compound (yield, 80%). $^1$H NMR (200 MHz, CDCl$_3$): δ 3.72-3.76 (m, 8H), 4.16 (s, 3H), 6.66-6.70 (m, 2H), 7.24-7.52 (m, 4H), 7.80-7.81 (m, 1H), 8.21 (dd, J=5.4 and 1.8 Hz, 1H).

Example 105

1-[(6-Fluoro-3-methoxyquinoxalin-2-yl)aminocarbonyl]-4-(2-pyrimidyl)piperazine (Compound 105)

Ethyl N-(6-fluoro-3-methoxyquinoxalin-2-yl)carbamate and 1-(2-pyrimidyl)piperazine were reacted by the same way with the example 85 to obtain the titled compound (yield, 79%). $^1$H NMR (200 MHz, CDCl$_3$): δ 3.69 (s, 4H), 3.98 (s, 4H), 4.14 (s, 3H), 6.54 (t, J=4.8 Hz, 1H), 7.21-7.41 (m, 3H), 7.79 (t, J=8.4 Hz, 1H), 8.34 (d, J=4.8 Hz, 2H).

Example 106

1-[(6-Chloro-3-methoxyquinoxalin-2-yl)aminocarbonyl]-4-phenylpiperazine (Compound 106)

a) 6-Chloro-2-(2,4-dimethoxybenzylamino)-3-methoxyquinoxaline

To 2,6-dichloro-3-methoxyquinoxaline (4.00 g, 17.5 mmol) dissolved in dimethyl-sulfoxide (40 ml), 2,4-dimethoxybenzylamine (14.6 g, 87.3 mmol) was added at room temperature. The mixture was stirred at room temperature for 36 hours and then water was added thereto. The product was extracted with ethyl acetate and the organic layer was washed with water and dried over MgSO$_4$. After concentration under the reduced pressure, the crude product was purified by SiO$_2$ column chromatography. Extraction of the residue with a n-hexane:ethyl acetate (30:1) mixture and concentration gave 4.93 g of the titled compound (yield, 78%).

b) 2-Amino-6-chloro-3-methoxyquinoxaline

To 6-chloro-2-(2,4-dimethoxybenzylamino)-3-methoxyquinoxaline (4.42 g, 12.3 mmol), 50 ml of 50% trifluoroacetic acid in dichloromethane was added at room temperature. The resulting mixture was stirred at room temperature for 18 hours and concentrated under the reduced pressure to remove the solvent. The residue was neutralized with saturated sodium bicarbonate solution and then NaCl solution was added thereto. The product was extracted with dichloromethane and the organic layer was dried over MgSO$_4$. After concentration under the reduced pressure, the crude product was purified by SiO$_2$ column chromatography. Extraction of the residue with a n-hexane:ethyl acetate (4:1) mixture and concentration gave 1.52 g of the titled compound (yield, 59%).

c) Ethyl N-(6-chloro-3-methoxyquinoxalin-2-yl)carbamate

2-Amino-6-chloro-3-methoxyquinoxaline (629 mg, 3.00 mmol) and ethyl chloroformate (391 mg, 3.60 mmol) were dissolved in dichloromethane (50 ml) at room temperature and thereto pyridine (285 mg, 3.60 mmol) was added. The resulting mixture was stirred at room temperature for 10 hours and concentrated under the reduced pressure to remove the solvent, and purified by SiO$_2$ column chromatography. Extraction of the residue with a n-hexane:ethyl acetate (3:1) mixture and concentration gave 811 mg of the titled compound (yield, 96%).

d) 1-[(6-Chloro-3-methoxyquinoxalin-2-yl)aminocarbonyl]-4-phenylpiperazine

Ethyl N-(6-chloro-3-methoxyquinoxalin-2-yl)carbamate (28 mg, 0.10 mmol) and 1-phenylpiperazine (24 mg, 0.15 mmol) were dissolved in tetrahydrofuran (2 ml) at room temperature and thereto DBU (23 mg, 0.15 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (2:1) mixture and concentration gave 36 mg of the titled compound (yield, 94%). $^1$H NMR (300 MHz, CDCl$_3$): δ 3.30 (s, 4H), 3.77 (s, 4H), 4.15 (s, 3H), 6.90-6.97 (m, 3H), 7.28-7.45 (m, 4H), 7.75-7.76 (m, 1H).

Example 107

1-[(6-Chloro-3-methoxyquinoxalin-2-yl)aminocarbonyl]-4-(2-methoxyphenyl)piperazine (Compound 107)

Ethyl N-(6-chloro-3-methoxyquinoxalin-2-yl)carbamate and 1-(2-methoxyphenyl)piperazine were reacted by the same way with the example 106 to obtain the titled compound (yield, 92%). $^1$H NMR (300 MHz, CDCl$_3$): δ 3.17 (s, 4H), 3.82 (s, 4H), 3.89 (s, 3H), 4.15 (s, 3H), 6.89-6.97 (m, 3H), 7.06 (m, 1H), 7.45 (m, 1H), 7.75 (s, 2H).

Example 108

1-[(6-Chloro-3-methoxyquinoxalin-2-yl)aminocarbonyl]-4-(3-methoxyphenyl)piperazine (Compound 108)

Ethyl N-(6-chloro-3-methoxyquinoxalin-2-yl)carbamate and 1-(3-methoxyphenyl)piperazine were reacted by the same way with the example 106 to obtain the titled compound (yield, 85%). $^1$H NMR (300 MHz, CDCl$_3$): δ 3.14-3.16 (m, 4H), 3.76-3.80 (m, 7H), 4.14 (s, 3H), 6.46-6.58 (m, 3H), 7.14-7.44 (m, 3H), 7.62-7.74 (m, 2H).

Example 109

1-[(6-Chloro-3-methoxyquinoxalin-2-yl)aminocarbonyl]-4-(4-methoxyphenyl)piperazine (Compound 109)

Ethyl N-(6-chloro-3-methoxyquinoxalin-2-yl)carbamate and 1-(4-methoxyphenyl)piperazine were reacted by the same way with the example 106 to obtain the titled compound (yield, 90%). $^1$H NMR (200 MHz, CDCl$_3$): δ 3.17 (s, 4H), 3.78 (s, 7H), 4.15 (m, 3H), 6.85-6.96 (m, 4H), 7.29-7.49 (m, 2H), 7.74-7.77 (m, 2H).

Example 110

1-[(6-Chloro-3-methoxyquinoxalin-2-yl)aminocarbonyl]-4-(3,5-dimethoxyphenyl)piperazine (Compound 110)

Ethyl N-(6-chloro-3-methoxyquinoxalin-2-yl)carbamate and 1-(3,5-dimethoxyphenyl)piperazine were reacted by the same way with the example 106 to obtain the titled compound (yield, 91%). MS (ESI) m/z 458 (M+1).

Example 111

1-[(6-Chloro-3-methoxyquinoxalin-2-yl)aminocarbonyl]-4-(3,4,5-trimethoxyphenyl)piperazine (Compound 111)

Ethyl N-(6-chloro-3-methoxyquinoxalin-2-yl)carbamate and 1-(3,4,5-trimethoxyphenyl)piperazine were reacted by the same way with the example 106 to obtain the titled compound (yield, 83%). $^1$H NMR (300 MHz, CDCl$_3$): δ 3.24 (s, 4H), 3.81-3.86 (m, 12H), 4.15 (s, 3H), 6.21 (s, 2H), 7.36-7.45 (m, 1H), 7.27 (s, 1H), 7.36-7.45 (m, 1H), 7.64-7.75 (m, 2H).

Example 112

1-[(6-Chloro-3-methoxyquinoxalin-2-yl)aminocarbonyl]-4-(2-methylphenyl)piperazine (Compound 112)

Ethyl N-(6-chloro-3-methoxyquinoxalin-2-yl)carbamate and 1-(2-methylphenyl)piperazine were reacted by the same way with the example 106 to obtain the titled compound (yield, 89%). $^1$H NMR (300 MHz, CDCl$_3$): δ 2.35 (s, 3H), 3.01 (s, 4H), 3.76 (s, 4H), 4.14 (s, 3H), 7.03-7.52 (m, 6H), 7.68-7.77 (m, 2H).

Example 113

1-[(6-Chloro-3-methoxyquinoxalin-2-yl)aminocarbonyl]-4-(3-methylphenyl)piperazine (Compound 113)

Ethyl N-(6-chloro-3-methoxyquinoxalin-2-yl)carbamate and 1-(3-methylphenyl)piperazine were reacted by the same way with the example 106 to obtain the titled compound (yield, 97%). $^1$H NMR (300 MHz, CDCl$_3$): δ 3.27-3.30 (m, 4H), 3.74-3.77 (m, 4H), 4.15 (s, 3H), 6.75-6.78 (m, 3H), 7.11-7.45 (m, 3H), 7.74-7.76 (m, 2H).

Example 114

1-[(6-Chloro-3-methoxyquinoxalin-2-yl)aminocarbonyl]-4-(2,6-dimethylphenyl)piperazine (Compound 114)

Ethyl N-(6-chloro-3-methoxyquinoxalin-2-yl)carbamate and 1-(2,6-dimethylphenyl)piperazine were reacted by the same way with the example 106 to obtain the titled compound (yield, 90%). $^1$H NMR (300 MHz, CDCl$_3$): δ 2.36 (s, 3H), 3.14 (s, 4H), 3.70 (s, 4H), 4.15 (s, 3H), 6.95-7.01 (m, 3H), 7.26-7.46 (m, 3H), 7.61-7.81 (m, 2H).

Example 115

1-[(6-Chloro-3-methoxyquinoxalin-2-yl)aminocarbonyl]-4-(3,5-dimethylphenyl)piperazine (Compound 115)

Ethyl N-(6-chloro-3-methoxyquinoxalin-2-yl)carbamate and 1-(3,5-dimethylphenyl)piperazine were reacted by the same way with the example 106 to obtain the titled compound (yield, 85%). $^1$H NMR (300 MHz, CDCl$_3$): δ 2.29 (s, 6H), 3.25-3.29 (m, 4H), 3.73-3.76 (m, 4H), 4.15 (s, 3H), 6.59 (s, 3H), 7.30-7.49 (m, 3H), 7.74-7.77 (m, 1H).

Example 116

1-[(6-Chloro-3-methoxyquinoxalin-2-yl)aminocarbonyl]-4-(3-trifluorotolyl)piperazine (Compound 116)

Ethyl N-(6-chloro-3-methoxyquinoxalin-2-yl)carbamate and 1-(3-trifluorotolyl)piperazine were reacted by the same way with the example 106 to obtain the titled compound (yield, 81%). ¹H NMR (300 MHz, CDCl₃): δ 3.37-3.38 (m, 4H), 3.77-3.80 (m, 4H), 4.16 (s, 3H), 7.08-7.45 (m, 6H), 7.73-7.76 (m, 2H).

Example 117

1-[(6-Chloro-3-methoxyquinoxalin-2-yl)aminocarbonyl]-4-(2-fluorophenyl)piperazine (Compound 117)

Ethyl N-(6-chloro-3-methoxyquinoxalin-2-yl)carbamate and 1-(2-fluorophenyl)piperazine were reacted by the same way with the example 106 to obtain the titled compound (yield, 93%). ¹H NMR (300 MHz, CDCl₃): δ 3.18 (s, 4H), 3.78 (s, 4H), 4.14 (s, 3H), 6.94-7.11 (m, 4H), 7.35-7.45 (m, 2H), 7.74-7.77 (m, 2H).

Example 118

1-[(6-Chloro-3-methoxyquinoxalin-2-yl)aminocarbonyl]-4-(4-fluorophenyl)piperazine (Compound 118)

Ethyl N-(6-chloro-3-methoxyquinoxalin-2-yl)carbamate and 1-(4-fluorophenyl)piperazine were reacted by the same way with the example 106 to obtain the titled compound (yield, 88%). ¹H NMR (300 MHz, CDCl₃): δ 3.19-3.22 (m, 4H), 3.75-3.78 (m, 4H), 4.16 (s, 3H), 6.89-6.93 (m, 4H), 7.29-7.46 (m, 2H), 7.74-7.76 (m, 1H).

Example 119

1-[(6-Chloro-3-methoxyquinoxalin-2-yl)aminocarbonyl]-4-(2-chlorophenyl)piperazine (Compound 119)

Ethyl N-(6-chloro-3-methoxyquinoxalin-2-yl)carbamate and 1-(2-chlorophenyl)piperazine were reacted by the same way with the example 106 to obtain the titled compound (yield, 91%). ¹H NMR (300 MHz, CDCl₃): δ 3.15 (s, 4H), 3.79 (s, 4H), 4.15 (s, 3H), 6.99-7.06 (m, 2H), 7.23-7.45 (m, 4H), 7.74-7.79 (m, 2H).

Example 120

1-[(6-Chloro-3-methoxyquinoxalin-2-yl)aminocarbonyl]-4-(3-chlorophenyl)piperazine (Compound 120)

Ethyl N-(6-chloro-3-methoxyquinoxalin-2-yl)carbamate and 1-(3-chlorophenyl)piperazine were reacted by the same way with the example 106 to obtain the titled compound (yield, 86%). ¹H NMR (300 MHz, CDCl₃): δ 3.30 (s, 4H), 3.76 (s, 4H), 4.15 (s, 3H), 6.79-6.90 (m, 3H), 7.15-7.45 (m, 3H), 7.62-7.75 (m, 2H).

Example 121

1-[(6-Chloro-3-methoxyquinoxalin-2-yl)aminocarbonyl]-4-(4-chlorophenyl)piperazine (Compound 121)

Ethyl N-(6-chloro-3-methoxyquinoxalin-2-yl)carbamate and 1-(4-chlorophenyl)piperazine were reacted by the same way with the example 106 to obtain the titled compound (yield, 94%). ¹H NMR (300 MHz, CDCl₃): δ 3.25 (s, 4H), 3.76 (s, 4H), 4.15 (s, 3H), 6.86 (d, J=9.0 Hz, 2H), 7.22-7.45 (m, 4H), 7.72-7.75 (m, 2H).

Example 122

1-[(6-Chloro-3-methoxyquinoxalin-2-yl)aminocarbonyl]-4-(2-cyanophenyl)piperazine (Compound 122)

Ethyl N-(6-chloro-3-methoxyquinoxalin-2-yl)carbamate and 1-(2-cyanophenyl)piperazine were reacted by the same way with the example 106 to obtain the titled compound (yield, 89%). ¹H NMR (300 MHz, CDCl₃): δ 3.30 (s, 4H), 3.84 (s, 4H), 4.14 (s, 3H), 7.02-7.10 (m, 2H), 7.35-7.89 (m, 6H).

Example 123

1-[(6-Chloro-3-methoxyquinoxalin-2-yl)aminocarbonyl]-4-(4-acetylphenyl)piperazine (Compound 123)

Ethyl N-(6-chloro-3-methoxyquinoxalin-2-yl)carbamate and 1-(4-acetylphenyl)piperazine were reacted by the same way with the example 106 to obtain the titled compound (yield, 81%). ¹H NMR (300 MHz, CDCl₃): δ 2.54 (s, 3H), 3.50 (s, 4H), 3.79 (s, 4H), 4.15 (s, 3H), 6.89 (d, J=9.0 Hz, 2H), 7.31-7.50 (m, 2H), 7.65-7.75 (m, 2H), 7.90 (d, J=8.7 Hz, 2H).

Example 124

1-[(6-Chloro-3-methoxyquinoxalin-2-yl)aminocarbonyl]-4-(4-nitrophenyl)piperazine (Compound 124)

Ethyl N-(6-chloro-3-methoxyquinoxalin-2-yl)carbamate and 1-(4-nitrophenyl)piperazine were reacted by the same way with the example 106 to obtain the titled compound (yield, 96%). ¹H NMR (300 MHz, DMSO-d₆): δ 3.57-3.65 (m, 8H), 4.17 (s, 3H), 7.05 (d, J=9.5 Hz, 2H), 7.55 (dd, J=8.9 and 2.2 Hz, 1H), 7.74-7.79 (m, 2H), 8.08 (d, J=9.4 Hz, 2H), 9.40 (s, 1H).

Example 125

1-[(6-Chloro-3-methoxyquinoxalin-2-yl)aminocarbonyl]-4-(2-pyridyl)piperazine (Compound 125)

Ethyl N-(6-chloro-3-methoxyquinoxalin-2-yl)carbamate and 1-(2-pyridyl)piperazine were reacted by the same way with the example 106 to obtain the titled compound (yield, 87%). ¹H NMR (300 MHz, CDCl₃): δ 3.73 (m, 8H), 4.15 (s, 3H), 6.68 (d, J=8.4 Hz, 2H), 7.11-7.76 (m, 5H), 8.21 (dd, J=3.6 and 0.6 Hz, 1H).

Example 126

1-[(6-Chloro-3-methoxyquinoxalin-2-yl)aminocarbonyl]-4-(2-pyrimidyl)piperazine (Compound 126)

Ethyl N-(6-chloro-3-methoxyquinoxalin-2-yl)carbamate and 1-(2-pyrimidyl)piperazine were reacted by the same way with the example 106 to obtain the titled compound (yield, 90%). ¹H NMR (300 MHz, CDCl₃): δ 3.69-3.73 (m, 4H), 3.98 (s, 4H), 4.16 (s, 3H), 6.54-6.55 (m, 1H), 7.28-7.49 (m, 1H), 7.63-7.75 (m, 2H), 8.33 (d, J=4.8 Hz, 2H).

Example 127

1-[(3-Methoxy-6-methylquinoxalin-2-yl)aminocarbonyl]-4-phenylpiperazine (Compound 127)

a) 2-(2,4-Dimethoxybenzylamino)-3-methoxy-6-methylquinoxaline

To 2-chloro-3-methoxy-6-methylquinoxaline (3.05 g, 14.6 mmol) dissolved in dimethylsulfoxide (40 ml), 2,4-dimethoxybenzylamine (9.77 g, 58.4 mmol) was added at room temperature. The mixture was stirred at 60° C. for 45 hours and then water was added thereto. The product was extracted with ethyl acetate and the organic layer was washed with water and dried over $MgSO_4$. After concentration under the reduced pressure, the crude product was purified by $SiO_2$ column chromatography. Extraction of the residue with a n-hexane:ethyl acetate (13:1) mixture and concentration gave 4.48 g of the titled compound (yield, 90%).

b) 2-Amino-3-methoxy-6-methylquinoxaline

To 2-(2,4-dimethoxybenzylamino)-3-methoxy-6-methylquinoxaline (4.48 g, 13.2 mmol), 30 ml of 50% trifluoroacetic acid in dichloromethane was added at room temperature. The resulting mixture was stirred at room temperature for 18 hours and concentrated under the reduced pressure to remove the solvent. The residue was neutralized with saturated sodium bicarbonate solution and then NaCl solution was added thereto. The product was extracted with dichloromethane and the organic layer was dried over $MgSO_4$. After concentration under the reduced pressure, the crude product was purified by $SiO_2$ column chromatography. Extraction of the residue with a n-hexane:ethyl acetate (3:1) mixture and concentration gave 2.01 g of the titled compound (yield, 81%).

c) Ethyl N-(3-methoxy-6-methylquinoxalin-2-yl)carbamate

2-Amino-3-methoxy-6-methylquinoxaline (1.15 g, 6.08 mmol) and ethyl chloroformate (1.32 g, 12.2 mmol) were dissolved in dichloromethane (30 ml) at room temperature and thereto pyridine (0.96 g, 12.2 mmol) was added. The resulting mixture was stirred at room temperature for 24 hours and concentrated under the reduced pressure to remove the solvent, and purified by $SiO_2$ column chromatography. Extraction of the residue with a n-hexane:ethyl acetate (3:1) mixture and concentration gave 1.59 g of the titled compound (yield, 100%).

d) 1-[(3-Methoxy-6-methylquinoxalin-2-yl)aminocarbonyl]-4-phenylpiperazine

Ethyl N-(3-methoxy-6-methylquinoxalin-2-yl)carbamate (30 mg, 0.11 mmol) and 1-phenylpiperazine (24 mg, 0.15 mmol) were dissolved in tetrahydrofuran (2 ml) at room temperature and thereto DBU (23 mg, 0.15 mmol) was added. The resulting mixture was stirred at 70° C. for 7 hours and concentrated under the reduced pressure to remove the solvent, and purified by $SiO_2$ column chromatography. Extraction of the residue with a n-hexane:ethyl acetate (2:1) mixture and concentration gave 34 mg of the titled compound (yield, 90%). $^1$H NMR (300 MHz, $CDCl_3$): δ 2.43 (s, 3H), 3.22-3.29 (m, 4H), 3.73-3.87 (m, 4H), 4.13 (s, 3H), 6.87-7.74 (m, 9H).

Example 128

1-[(3-Methoxy-6-methylquinoxalin-2-yl)aminocarbonyl]-4-(2-methoxyphenyl)piperazine (Compound 128)

Ethyl N-(3-methoxy-6-methylquinoxalin-2-yl)carbamate and 1-(2-methoxyphenyl)piperazine were reacted by the same way with the example 127 to obtain the titled compound (yield, 90%). $^1$H NMR (300 MHz, $CDCl_3$): δ 2.49 (s, 3H), 3.09-3.18 (m, 4H), 3.77-3.82 (m, 4H), 3.88 (s, 3H), 4.13 (s, 3H), 6.87-7.80 (m, 8H).

Example 129

1-[(3-Methoxy-6-methylquinoxalin-2-yl)aminocarbonyl]-4-(3-methoxyphenyl)piperazine (Compound 129)

Ethyl N-(3-methoxy-6-methylquinoxalin-2-yl)carbamate and 1-(3-methoxyphenyl)piperazine were reacted by the same way with the example 127 to obtain the titled compound (yield, 89%). $^1$H NMR (300 MHz, $CDCl_3$): δ 2.49 (s, 3H), 3.19-3.32 (m, 4H), 3.61-3.90 (m, 4H), 3.79 (s, 3H), 4.17 (s, 3H), 6.44-6.58 (m, 4H), 7.00-7.65 (m, 3H), 7.72 (d, J=8.2 Hz, 1H).

Example 130

1-[(3-Methoxy-6-methylquinoxalin-2-yl)aminocarbonyl]-4-(4-methoxyphenyl)piperazine (Compound 130)

Ethyl N-(3-methoxy-6-methylquinoxalin-2-yl)carbamate and 1-(4-methoxyphenyl)piperazine were reacted by the same way with the example 127 to obtain the titled compound (yield, 96%). $^1$H NMR (200 MHz, $CDCl_3$): δ 2.50 (s, 3H), 3.15-3.17 (m, 4H), 3.68-3.78 (m, 4H), 3.78 (s, 3H), 4.14 (s, 3H), 6.84-7.75 (m, 8H).

Example 131

1-[(3-Methoxy-6-methylquinoxalin-2-yl)aminocarbonyl]-4-(3,5-dimethoxyphenyl)piperazine (Compound 131)

Ethyl N-(3-methoxy-6-methylquinoxalin-2-yl)carbamate and 1-(3,5-dimethoxyphenyl)piperazine were reacted by the same way with the example 127 to obtain the titled compound (yield, 88%). MS (ESI) m/z 438 (M+1).

Example 132

1-[(3-Methoxy-6-methylquinoxalin-2-yl)aminocarbonyl]-4-(3,4,5-trimethoxyphenyl)piperazine (Compound 132)

Ethyl N-(3-methoxy-6-methylquinoxalin-2-yl)carbamate and 1-(3,4,5-trimethoxyphenyl)piperazine were reacted by the same way with the example 127 to obtain the titled compound (yield, 91%). $^1$H NMR (300 MHz, $CDCl_3$): δ 2.49 (s, 3H), 3.16-3.23 (m, 4H), 3.71-3.95 (m, 4H), 3.80 (s, 3H), 3.86 (s, 6H), 4.13 (s, 3H), 6.19 (s, 2H), 7.08-7.62 (m, 3H), 7.72 (d, J=8.6 Hz, 1H).

Example 133

1-[(3-Methoxy-6-methylquinoxalin-2-yl)aminocarbonyl]-4-(2-methylphenyl)piperazine (Compound 133)

Ethyl N-(3-methoxy-6-methylquinoxalin-2-yl)carbamate and 1-(2-methylphenyl)piperazine were reacted by the same way with the example 127 to obtain the titled compound (yield, 84%). $^1$H NMR (300 MHz, CDCl$_3$): δ 2.35 (s, 3H), 2.50 (s, 3H), 2.89-3.09 (m, 4H), 3.68-3.88 (m, 4H), 4.14 (s, 3H), 6.99-7.78 (m, 7H), 7.76 (d, J=8.0 Hz, 1H).

Example 134

1-[(3-Methoxy-6-methylquinoxalin-2-yl)aminocarbonyl]-4-(3-methylphenyl)piperazine (Compound 134)

Ethyl N-(3-methoxy-6-methylquinoxalin-2-yl)carbamate and 1-(3-methylphenyl)piperazine were reacted by the same way with the example 127 to obtain the titled compound (yield, 91%). $^1$H NMR (300 MHz, CDCl$_3$): δ 2.33 (s, 3H), 2.46 (s, 3H), 3.21-3.28 (m, 4H), 3.72-3.86 (m, 4H), 4.13 (s, 3H), 6.74-6.78 (m, 4H), 7.00-8.01 (m, 4H).

Example 135

1-[(3-Methoxy-6-methylquinoxalin-2-yl)aminocarbonyl]-4-(2,6-dimethylphenyl)piperazine (Compound 135)

Ethyl N-(3-methoxy-6-methylquinoxalin-2-yl)carbamate and 1-(2,6-dimethylphenyl)piperazine were reacted by the same way with the example 127 to obtain the titled compound (yield, 83%). $^1$H NMR (300 MHz, CDCl$_3$): δ 2.33-2.50 (m, 9H), 3.14-2.20 (m, 4H), 3.70-3.75 (m, 4H), 4.14 (s, 3H), 7.00 (s, 3H), 7.09-7.78 (m, 3H).

Example 136

1-[(3-Methoxy-6-methylquinoxalin-2-yl)aminocarbonyl]-4-(3,5-dimethylphenyl)piperazine (Compound 136)

Ethyl N-(3-methoxy-6-methylquinoxalin-2-yl)carbamate and 1-(3,5-dimethylphenyl)piperazine were reacted by the same way with the example 127 to obtain the titled compound (yield, 95%). $^1$H NMR (300 MHz, CDCl$_3$): δ 2.29 (s, 6H), 2.50 (s, 3H), 3.18-3.29 (m, 4H), 3.73-3.80 (m, 4H), 4.12 (s, 3H), 6.58 (s, 3H), 7.31 (d, J=8.4 Hz, 1H), 7.43 (s, 1H), 7.55 (s, 1H), 7.72 (d, J=8.4 Hz, 1H).

Example 137

1-[(3-Methoxy-6-methylquinoxalin-2-yl)aminocarbonyl]-4-(3-trifluorotolyl)piperazine (Compound 137)

Ethyl N-(3-methoxy-6-methylquinoxalin-2-yl)carbamate and 1-(3-trifluorotolyl)piperazine were reacted by the same way with the example 127 to obtain the titled compound (yield, 87%). $^1$H NMR (300 MHz, CDCl$_3$): δ 2.49 (s, 3H), 3.27-3.35 (m, 4H), 3.69-3.89 (m, 4H), 4.13 (s, 3H), 7.07-7.60 (m, 7H) 7.71 (d, J=8.2 Hz, 1H).

Example 138

1-[(3-Methoxy-6-methylquinoxalin-2-yl)aminocarbonyl]-4-(2-fluorophenyl)piperazine (Compound 138)

Ethyl N-(3-methoxy-6-methylquinoxalin-2-yl)carbamate and 1-(2-fluorophenyl)piperazine were reacted by the same way with the example 127 to obtain the titled compound (yield, 98%). $^1$H NMR (300 MHz, CDCl$_3$): δ 2.49 (s, 3H), 3.11-3.18 (m, 4H), 3.77-3.86 (m, 4H), 4.12 (s, 3H), 6.95-7.61 (m, 7H), 7.73 (d, J=8.6 Hz, 1H).

Example 139

1-[(3-Methoxy-6-methylquinoxalin-2-yl)aminocarbonyl]-4-(4-fluorophenyl)piperazine (Compound 139)

Ethyl N-(3-methoxy-6-methylquinoxalin-2-yl)carbamate and 1-(4-fluorophenyl)piperazine were reacted by the same way with the example 127 to obtain the titled compound (yield, 90%). $^1$H NMR (300 MHz, CDCl$_3$): δ 2.47 (s, 3H), 3.07-3.17 (m, 4H), 3.77-3.87 (m, 4H), 4.13 (s, 3H), 6.87-8.01 (m, 8H).

Example 140

1-[(3-Methoxy-6-methylquinoxalin-2-yl)aminocarbonyl]-4-(2-chlorophenyl)piperazine (Compound 140)

Ethyl N-(3-methoxy-6-methylquinoxalin-2-yl)carbamate and 1-(2-chlorophenyl)piperazine were reacted by the same way with the example 127 to obtain the titled compound (yield, 85%). $^1$H NMR (300 MHz, CDCl$_3$): δ 2.49 (s, 3H), 3.08-3.17 (m, 4H), 3.73-3.86 (m, 4H), 4.13 (s, 3H), 7.00-7.65 (m, 7H), 7.74 (d, J=8.0 Hz, 1H).

Example 141

1-[(3-Methoxy-6-methylquinoxalin-2-yl)aminocarbonyl]-4-(3-chlorophenyl)piperazine (Compound 141)

Ethyl N-(3-methoxy-6-methylquinoxalin-2-yl)carbamate and 1-(3-chlorophenyl)piperazine were reacted by the same way with the example 127 to obtain the titled compound (yield, 87%). $^1$H NMR (300 MHz, CDCl$_3$): δ 2.46 (s, 3H), 3.19-3.33 (m. 4H), 3.72-3.77 (m, 4H), 4.13 (s, 3H), 6.79-7.66 (m, 7H), 7.71 (d, J=8.6 Hz, 1H).

Example 142

1-[(3-Methoxy-6-methylquinoxalin-2-yl)aminocarbonyl]-4-(4-chlorophenyl)piperazine (Compound 142)

Ethyl N-(3-methoxy-6-methylquinoxalin-2-yl)carbamate and 1-(4-chlorophenyl)piperazine were reacted by the same way with the example 127 to obtain the titled compound (yield, 91%). $^1$H NMR (300 MHz, CDCl$_3$): δ 2.50 (s, 3H), 3.18-3.28 (m, 4H), 3.73-3.78 (m, 4H), 4.14 (s, 3H), 6.86 (dd, J=12.2 Hz, 2H), 7.00-7.60 (m, 5H), 7.71 (d, J=8.2 Hz, 1H).

Example 143

1-[(3-Methoxy-6-methylquinoxalin-2-yl)aminocarbonyl]-4-(2-cyanophenyl)piperazine (Compound 143)

Ethyl N-(3-methoxy-6-methylquinoxalin-2-yl)carbamate and 1-(2-cyanophenyl)piperazine were reacted by the same way with the example 127 to obtain the titled compound (yield, 93%). $^1$H NMR (300 MHz, CDCl$_3$): δ 2.47 (s, 3H), 3.20-3.28 (m, 4H), 3.76-3.96 (m, 4H), 4.14 (s, 3H), 7.02-7.13 (m, 3H), 7.28 (s, 1H), 7.49-7.63 (m, 4H).

Example 144

1-[(3-Methoxy-6-methylquinoxalin-2-yl)aminocarbonyl]-4-(4-acetylphenyl)piperazine (Compound 144)

Ethyl N-(3-methoxy-6-methylquinoxalin-2-yl)carbamate and 1-(4-acetylphenyl)piperazine were reacted by the same way with the example 127 to obtain the titled compound (yield, 97%). $^1$H NMR (300 MHz, CDCl$_3$): δ 2.17 (s, 3H), 2.54 (s, 3H), 3.39-3.58 (m, 4H), 3.71-3.90 (m, 4H), 4.14 (s, 3H), 6.89 (d, J=6.4 Hz, 2H), 7.21-7.54 (m, 4H), 7.90 (d, J=6.4 Hz, 2H).

Example 145

1-[(3-Methoxy-6-methylquinoxalin-2-yl)aminocarbonyl]-4-(4-nitrophenyl)piperazine (Compound 145)

Ethyl N-(3-methoxy-6-methylquinoxalin-2-yl)carbamate and 1-(4-nitrophenyl)piperazine were reacted by the same way with the example 127 to obtain the titled compound (yield, 89%). $^1$H NMR (300 MHz, CDCl$_3$): δ 2.45 (s, 3H), 3.45-3.60 (m, 4H), 3.76-3.88 (m, 4H), 4.09 (s, 3H), 6.85 (d, J=6.2 Hz, 2H), 7.03-7.68 (m, 4H), 8.16 (d, J=6.0 Hz, 2H).

Example 146

1-[(3-Methoxy-6-methylquinoxalin-2-yl)aminocarbonyl]-4-(2-pyridyl)piperazine (Compound 146)

Ethyl N-(3-methoxy-6-methylquinoxalin-2-yl)carbamate and 1-(2-pyridyl)piperazine were reacted by the same way with the example 127 to obtain the titled compound (yield, 88%). $^1$H NMR (300 MHz, CDCl$_3$): δ 2.49 (s, 3H), 3.61-3.71 (m, 8H), 4.12 (s, 3H), 6.66 (d, J=8 Hz, 2H), 7.07-7.74 (m, 5H), 8.20 (dd, J=5.4, 1.8 Hz, 1H).

Example 147

1-[(3-Methoxy-6-methylquinoxalin-2-yl)aminocarbonyl]-4-(2-pyrimidyl)piperazine (Compound 147)

Ethyl N-(3-methoxy-6-methylquinoxalin-2-yl)carbamate and 1-(2-pyrimidyl)piperazine were reacted by the same way with the example 127 to obtain the titled compound (yield, 79%). $^1$H NMR (300 MHz, CDCl$_3$): δ 2.45 (s, 3H), 3.60-3.80 (m, 4H), 3.80-4.05 (m, 4H), 4.13 (s, 3H), 6.52 (t, J=4.5 Hz, 1H), 7.00-7.69 (m, 4H), 8.32 (d, J=4.5 Hz, 2H).

Example 148

1-[(3,6-Dimethoxyquinoxalin-2-yl)aminocarbonyl]-4-phenylpiperazine (Compound 148)

a) 3,6-Dimethoxy-2-(2,4-dimethoxybenzylamino)quinoxaline

To 2-chloro-3,6-dimethoxyquinoxaline (3.87 g, 17.2 mmol) dissolved in dimethyl-sulfoxide (70 ml), 2,4-dimethoxybenzylamine (6.07 g, 36.3 mmol) was added at room temperature. The mixture was stirred at 60° C. for 118 hours and then water was added thereto. The product was extracted with ethyl acetate and the organic layer was washed with water and dried over MgSO$_4$. After concentration under the reduced pressure, the crude product was purified by SiO$_2$ column chromatography. Extraction of the residue with a n-hexane:ethyl acetate (6:1) mixture and concentration gave 4.69 g of the titled compound (yield, 77%).

b) 2-Amino-3,6-dimethoxyquinoxaline

To 3,6-dimethoxy-2-(2,4-dimethoxybenzylamino)quinoxaline (4.45 g, 12.8 mmol), 70 ml of 50% trifluoroacetic acid in dichloromethane was added at room temperature. The resulting mixture was stirred at room temperature for 18 hours and concentrated under the reduced pressure to remove the solvent. The residue was neutralized with saturated sodium bicarbonate solution and then NaCl solution was added thereto. The product was extracted with dichloromethane and the organic layer was dried over MgSO$_4$. After concentration under the reduced pressure, the crude product was purified by SiO$_2$ column chromatography. Extraction of the residue with a n-hexane:ethyl acetate mixture and concentration gave 2.50 g of the titled compound (yield, 95%).

c) Ethyl N-(3,6-dimethoxyquinoxalin-2-yl)carbamate

3-Amino-2,6-dimethoxyquinoxaline (616 mg, 3.00 mmol) and ethyl chloroformate (391 mg, 3.60 mmol) were dissolved in dichloromethane (50 ml) at room temperature and thereto pyridine (285 mg, 3.60 mmol) was added. The resulting mixture was stirred at room temperature for 10 hours and concentrated under the reduced pressure to remove the solvent, and purified by SiO$_2$ column chromatography. Extraction of the residue with a n-hexane:ethyl acetate (3:1) mixture and concentration gave 782 mg of the titled compound (yield, 94%).

d) 1-[(3,6-Dimethoxyquinoxalin-2-yl)aminocarbonyl]-4-phenylpiperazine

Ethyl N-(3,6-dimethoxyquinoxalin-2-yl)carbamate (28 mg, 0.10 mmol) and 1-phenylpiperazine (24 mg, 0.15 mmol) were dissolved in tetrahydrofuran (2 ml) at room temperature and thereto DBU (23 mg, 0.15 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (2:1) mixture and concentration gave 36 mg of the titled compound (yield, 91%). $^1$H NMR (300 MHz, CDCl$_3$): δ 3.27 (s, 4H), 3.76 (s, 4H), 3.89 (s, 3H), 4.12 (s, 3H), 6.87-6.96 (m, 3H), 7.13 (s, 2H), 7.29-7.31 (m, 2H), 7.72-7.75 (s, 1H).

Example 149

1-[(3,6-Dimethoxyquinoxalin-2-yl)aminocarbonyl]-4-(2-methoxyphenyl)piperazine (Compound 149)

Ethyl N-(3,6-dimethoxyquinoxalin-2-yl)carbamate and 1-(2-methoxyphenyl)piperazine were reacted by the same way with the example 148 to obtain the titled compound (yield, 84%). $^1$H NMR (300 MHz, CDCl$_3$): δ 3.13-3.16 (m, 4H), 3.66-3.78 (m, 4H), 3.88 (s, 3H), 3.90 (s, 3H), 4.12 (s, 3H), 6.87-7.14 (m, 7H), 7.76 (d, J=5.1 Hz, 1H).

Example 150

1-[(3,6-Dimethoxyquinoxalin-2-yl)aminocarbonyl]-4-(3-methoxyphenyl)piperazine (Compound 150)

Ethyl N-(3,6-dimethoxyquinoxalin-2-yl)carbamate and 1-(3-methoxyphenyl)piperazine were reacted by the same way with the example 148 to obtain the titled compound (yield, 90%). $^1$H NMR (300 MHz, CDCl$_3$): δ 3.27 (s, 4H), 3.75 (s, 4H), 3.79 (s, 3H), 3.89 (s, 3H), 4.12 (s, 3H), 6.44-6.57 (m, 3H), 7.14-7.22 (m, 4H), 7.72-7.75 (m, 1H).

Example 151

1-[(3,6-Dimethoxyquinoxalin-2-yl)aminocarbonyl]-4-(4-methoxyphenyl)piperazine (Compound 151)

Ethyl N-(3,6-dimethoxyquinoxalin-2-yl)carbamate and 1-(4-methoxyphenyl)piperazine were reacted by the same way with the example 148 to obtain the titled compound (yield, 87%). $^1$H NMR (300 MHz, CDCl$_3$): δ 3.12-3.15 (m, 4H), 3.74-3.76 (m, 7H), 3.89 (s, 3H), 4.11 (s, 3H), 6.83-6.93 (m, 4H), 7.12-7.13 (m, 2H), 7.33 (s, 1H), 7.72-7.75 (m, 1H).

Example 152

1-[(3,6-Dimethoxyquinoxalin-2-yl)aminocarbonyl]-4-(3,5-dimethoxyphenyl)piperazine (Compound 152)

Ethyl N-(3,6-dimethoxyquinoxalin-2-yl)carbamate and 1-(3,5-dimethoxyphenyl piperazine were reacted by the same way with the example 148 to obtain the titled compound (yield, 86%). MS (ESI) m/z 454 (M+1).

Example 153

1-[(3,6-Dimethoxyquinoxalin-2-yl)aminocarbonyl]-4-(3,4,5-trimethoxyphenyl)piperazine (Compound 153)

Ethyl N-(3,6-dimethoxyquinoxalin-2-yl)carbamate and 1-(3,4,5-trimethoxyphenyl)piperazine were reacted by the same way with the example 148 to obtain the titled compound (yield, 92%).

Example 154

1-[(3,6-Dimethoxyquinoxalin-2-yl)aminocarbonyl]-4-(2-methylphenyl)piperazine (Compound 154)

Ethyl N-(3,6-dimethoxyquinoxalin-2-yl)carbamate and 1-(2-methylphenyl)piperazine were reacted by the same way with the example 148 to obtain the titled compound (yield, 93%). $^1$H NMR (300 MHz, CDCl$_3$): δ 2.35 (s, 3H), 2.99-3.02 (m, 4H), 3.73-3.76 (m, 4H), 3.91 (s, 3H), 4.15 (s, 3H), 7.00-7.22 (m, 7H), 7.76-7.79 (m, 1H).

Example 155

1-[(3,6-Dimethoxyquinoxalin-2-yl)aminocarbonyl]-4-(3-methylphenyl)piperazine (Compound 155)

Ethyl N-(3,6-dimethoxyquinoxalin-2-yl)carbamate and 1-(3-methylphenyl)piperazine were reacted by the same way with the example 148 to obtain the titled compound (yield, 86%). $^1$H NMR (300 MHz, CDCl$_3$): δ 2.33 (s, 3H), 3.26-3.29 (m, 4H), 3.73-3.77 (m, 4H), 3.90 (s, 3H), 4.13 (s, 3H), 6.73-6.77 (m, 3H), 7.13-7.22 (m, 4H), 7.74 (d, J=9.8 Hz, 1H).

Example 156

1-[(3,6-Dimethoxyquinoxalin-2-yl)aminocarbonyl]-4-(2,6-dimethylphenyl)piperazine (Compound 156)

Ethyl N-(3,6-dimethoxyquinoxalin-2-yl)carbamate and 1-(2,6-dimethylphenyl)piperazine were reacted by the same way with the example 148 to obtain the titled compound (yield, 91%). $^1$H NMR (300 MHz, CDCl$_3$): δ 2.36 (s, 6H), 3.17-3.21 (m, 4H), 3.68-3.71 (m, 4H), 3.91 (s, 3H), 4.14 (s, 3H), 6.95-7.03 (m, 3H), 7.14-7.21 (m, 3H), 7.77-7.80 (m, 1H).

Example 157

1-[(3,6-Dimethoxyquinoxalin-2-yl)aminocarbonyl]-4-(3,5-dimethylphenyl)piperazine (Compound 157)

Ethyl N-(3,6-dimethoxyquinoxalin-2-yl)carbamate and 1-(3,5-dimethylphenyl)piperazine were reacted by the same way with the example 148 to obtain the titled compound (yield, 90%). $^1$H NMR (300 MHz, CDCl$_3$): δ 2.29 (s, 6H), 3.26 (s, 4H), 3.75 (s, 4H), 3.90 (s, 3H), 4.14 (s, 3H), 6.59 (s, 3H), 6.99-7.20 (m, 3H), 7.73-7.75 (m, 1H).

Example 158

1-[(3,6-Dimethoxyquinoxalin-2-yl)aminocarbonyl]-4-(3-trifluorotolyl)piperazine (Compound 158)

Ethyl N-(3,6-dimethoxyquinoxalin-2-yl)carbamate and 1-(3-trifluorotolyl)piperazine were reacted by the same way with the example 148 to obtain the titled compound (yield, 83%). $^1$H NMR (300 MHz, CDCl$_3$): δ 3.28-3.34 (m, 4H), 3.75-3.78 (m, 4H), 3.90 (s, 3H), 4.13 (s, 3H), 7.06-7.14 (m, 5H), 7.28-7.40 (m, 2H), 7.73 (d, J=9.9 Hz, 1H).

Example 159

1-[(3,6-Dimethoxyquinoxalin-2-yl)aminocarbonyl]-4-(2-fluorophenyl)piperazine (Compound 159)

Ethyl N-(3,6-dimethoxyquinoxalin-2-yl)carbamate and 1-(2-fluorophenyl)piperazine were reacted by the same way with the example 148 to obtain the titled compound (yield, 95%). $^1$H NMR (300 MHz, CDCl$_3$): δ 3.18 (s, 4H), 3.66 (s, 4H), 3.78 (s, 3H), 4.15 (s, 3H), 6.94-7.27 (m, 7H), 7.73-7.87 (m, 1H).

Example 160

1-[(3,6-Dimethoxyquinoxalin-2-yl)aminocarbonyl]-4-(4-fluorophenyl)piperazine (Compound 160)

Ethyl N-(3,6-dimethoxyquinoxalin-2-yl)carbamate and 1-(4-fluorophenyl)piperazine were reacted by the same way with the example 148 to obtain the titled compound (yield, 92%). $^1$H NMR (300 MHz, CDCl$_3$): δ 3.17 (s, 4H), 3.75 (s, 4H), 3.89 (s, 3H), 4.12 (s, 3H), 6.86-7.01 (m, 4H), 7.13 (s, 2H), 7.32 (s, 1H), 7.72-7.74 (m, 1H).

Example 161

1-[(3,6-Dimethoxyquinoxalin-2-yl)aminocarbonyl]-4-(2-chlorophenyl)piperazine (Compound 161)

Ethyl N-(3,6-dimethoxyquinoxalin-2-yl)carbamate and 1-(2-chlorophenyl)piperazine were reacted by the same way with the example 148 to obtain the titled compound (yield, 89%). $^1$H NMR (300 MHz, CDCl$_3$): δ 3.13 (s, 4H), 3.78 (s, 4H), 3.90 (s, 3H), 4.12 (s, 3H), 6.98-7.37 (m, 7H), 7.76 (d, J=9.9 Hz, 1H).

Example 162

1-[(3,6-Dimethoxyquinoxalin-2-yl)aminocarbonyl]-4-(3-chlorophenyl)piperazine (Compound 162)

Ethyl N-(3,6-dimethoxyquinoxalin-2-yl)carbamate and 1-(3-chlorophenyl)piperazine were reacted by the same way with the example 148 to obtain the titled compound (yield, 85%). $^1$H NMR (300 MHz, CDCl$_3$): δ 2.29 (s, 4H), 3.74 (s, 4H), 3.90 (s, 3H), 4.13 (s, 4H), 6.78-6.89 (m, 3H), 7.15-7.27 (m, 4H), 7.73 (d, J=9.7 Hz, 1H).

Example 163

1-[(3,6-Dimethoxyquinoxalin-2-yl)aminocarbonyl]-4-(4-chlorophenyl)piperazine (Compound 163)

Ethyl N-(3,6-dimethoxyquinoxalin-2-yl)carbamate and 1-(4-chlorophenyl)piperazine were reacted by the same way with the example 148 to obtain the titled compound (yield, 93%). $^1$H NMR (300 MHz, CDCl$_3$): δ 3.23 (s, 4H), 3.75 (s, 4H), 3.90 (s, 3H), 4.13 (s, 3H), 6.85 (d, J=9.0 Hz, 2H), 7.14 (s, 2H), 7.20-7.25 (m, 3H), 7.71-7.74 (m, 1H).

Example 164

1-[(3,6-Dimethoxyquinoxalin-2-yl)aminocarbonyl]-4-(2-cyanophenyl)piperazine (Compound 164)

Ethyl N-(3,6-dimethoxyquinoxalin-2-yl)carbamate and 1-(2-cyanophenyl)piperazine were reacted by the same way with the example 148 to obtain the titled compound (yield, 97%). $^1$H NMR (300 MHz, CDCl$_3$): δ 2.46 (s, 3H), 3.28 (s, 4H), 3.86 (s, 3H), 4.08-4.19 (m, 4H), 7.01-7.08 (m, 3H), 7.17-7.37 (m, 1H), 7.49-7.61 (m, 4H)

Example 165

1-[(3,6-Dimethoxyquinoxalin-2-yl)aminocarbonyl]-4-(4-acetylphenyl)piperazine (Compound 165)

Ethyl N-(3,6-dimethoxyquinoxalin-2-yl)carbamate and 1-(4-acetylphenyl)piperazine were reacted by the same way with the example 148 to obtain the titled compound (yield, 93%). $^1$H NMR (300 MHz, CDCl$_3$): δ 2.53 (s, 3H), 3.48 (s, 4H), 3.77 (s, 4H), 3.90 (s, 3H), 4.13 (s, 3H), 6.86 (d, J=8.7 Hz, 2H), 7.14-7.28 (m, 3H), 7.72 (d, J=8.4 Hz, 1H), 7.89 (d, J=9.0 Hz, 2H).

Example 166

1-[(3,6-Dimethoxyquinoxalin-2-yl)aminocarbonyl]-4-(4-nitrophenyl)piperazine (Compound 166)

Ethyl N-(3,6-dimethoxyquinoxalin-2-yl)carbamate and 1-(4-nitrophenyl)piperazine were reacted by the same way with the example 148 to obtain the titled compound (yield, 94%). $^1$H NMR (300 MHz, CDCl$_3$): δ 3.57-3.65 (m, 8H), 3.90 (s, 3H), 4.01 (s, 3H), 7.06 (d, J=9.4 Hz, 2H), 7.18-7.22 (m, 2H), 7.69 (d, J=8.6 Hz, 2H), 8.09 (d, J=9.4 Hz, 2H), 9.20 (s, 1H).

Example 167

1-[(3,6-Dimethoxyquinoxalin-2-yl)aminocarbonyl]-4-(2-pyridyl)piperazine (Compound 167)

Ethyl N-(3,6-dimethoxyquinoxalin-2-yl)carbamate and 1-(2-pyridyl)piperazine were reacted by the same way with the example 148 to obtain the titled compound (yield, 94%). $^1$H NMR (300 MHz, CDCl$_3$): δ 3.73 (m, 8H), 3.91 (s, 3H), 4.15 (s, 3H), 6.66-6.70 (m, 2H), 7.13-7.20 (m, 3H), 7.50-7.56 (m, 1H), 7.66 (d, J=9.0 Hz, 1H), 8.21 (dd, J=5.1 and 1.5 Hz, 1H).

Example 168

1-[(3,6-Dimethoxyquinoxalin-2-yl)aminocarbonyl]-4-(2-pyrimidyl)piperazine (Compound 168)

Ethyl N-(3,6-dimethoxyquinoxalin-2-yl)carbamate and 1-(2-pyrimidyl)piperazine were reacted by the same way with the example 148 to obtain the titled compound (yield, 86%). $^1$H NMR (300 MHz, CDCl$_3$): δ 3.67-3.70 (m, 4H), 3.90 (s, 3H), 3.95-3.97 (m, 4H), 4.13 (s, 3H), 6.53 (t, J=4.8 Hz, 1H), 7.11-7.23 (m, 4H), 7.30 (d, J=9.3 Hz, 1H), 8.33 (d, J=4.8 Hz, 2H).

Example 169

1-[(6,7-Difluoro-2-methoxyquinoxalin-3-yl)aminocarbonyl]-4-(3-methoxyphenyl)piperazine (Compound 169)

1. a) 2-Amino-6,7-difluoro-3-methoxyquinoxaline

To 2-amino-3-chloro-6,7-di fluoroquinoxaline (610 mg, 2.83 mmol) dissolved in tetrahydrofuran (40 ml), 25 wt % sodium methoxide (6.12 g, 28.3 mmol) in methanol was added at room temperature and stirred further at room temperature for 1.5 hour. The resulting mixture was concentrated under the reduced pressure to remove the solvent. The product was extracted with ethyl acetate and the organic layer was washed with water and dried over MgSO$_4$. After concentration under the reduced pressure, the crude product was purified by SiO$_2$ column chromatography. Extraction of the residue with a n-hexane:ethyl acetate (2:1) mixture and concentration gave 570 mg of the titled compound (yield, 95%).

b) Ethyl N-(6,7-difluoro-2-methoxyquinoxalin-3-yl)carbamate

2-Amino-6,7-di fluoro-3-methoxyquinoxaline (550 mg, 2.60 mmol) and ethyl chloroformate (564 mg, 5.20 mmol) were dissolved in dichloromethane (50 ml) at room temperature and thereto pyridine (411 mg, 5.20 mmol) was added. The mixture was stirred at room temperature for 13 hours and concentrated under the reduced pressure to remove the solvent, and purified by SiO$_2$ column chromatography. Extraction of the residue with a n-hexane:ethyl acetate (3:1) mixture and concentration gave 440 mg of the titled compound (yield, 60%).

c) 1-[(6,7-Difluoro-2-methoxyquinoxalin-3-yl)aminocarbonyl]-4-(3-methoxyphenyl)piperazine Ethyl N-(6,7-di fluoro-2-methoxyquinoxalin-3-yl)carbamate (25 mg, 0.088 mmol) and 1-(3-methoxy phenyl)piperazine (35 mg, 0.18 mmol) were dissolved in tetrahydrofuran (2 ml) at room temperature and thereto DBU (28 mg, 0.18 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (1:1) mixture and concentration gave 29 mg of the titled compound (yield, 76%). $^1$H NMR (300 MHz, CDCl$_3$) δ 3.28-3.30 (m, 4H), 3.76-3.77 (m, 4H), 3.81 (s, 3H), 4.12 (s, 3H), 6.48-6.49 (m, 2H), 6.56-6.58 (m, 1H), 7.20-7.23 (m, 1H), 7.29-7.30 (m, 1H), 7.50-7.53 (m, 1H), 7.60-7.62 (m, 1H).

Example 170

1-[(6,7-Difluoro-2-methoxyquinoxalin-3-yl)aminocarbonyl]-4-(3,5-dimethoxyphenyl)piperazine (Compound 170)

Ethyl N-(6,7-di fluoro-2-methoxyquinoxalin-3-yl)carbamate and 1-(3,5-di methoxyphenyl)piperazine were reacted by the same way with the example 169 to obtain the titled compound (yield, 70%). MS (ESI) m/z 460 ([M+H]$^+$).

Example 171

1-[(6,7-Difluoro-2-methoxyquinoxalin-3-yl)aminocarbonyl]-4-(3-methylphenyl)piperazine (Compound 171)

Ethyl N-(6,7-di fluoro-2-methoxyquinoxalin-3-yl)carbamate and 1-(3-methyl phenyl)piperazine were reacted by the same way with the example 169 to obtain the titled compound (yield, 66%). $^1$H NMR (300 MHz, CDCl$_3$) δ 2.34 (s, 3H), 3.27-3.29 (m, 4H), 3.75-3.77 (m, 4H), 4.15 (s, 3H), 6.75-6.78 (m, 4H), 7.18-7.21 (m, 1H), 7.49-7.53 (m, 1H), 7.58-7.62 (m, 1H).

Example 172

1-[(6,7-Difluoro-2-methoxyquinoxalin-3-yl)aminocarbonyl]-4-(3,5-dimethylphenyl)piperazine (Compound 172)

Ethyl N-(6,7-di fluoro-2-methoxyquinoxalin-3-yl)carbamate and 1-(3,5-dimethyl phenyl)piperazine were reacted by the same way with the example 169 to obtain the titled compound (yield, 70%). $^1$H NMR (300 MHz, CDCl$_3$) δ 2.30 (s, 6H), 3.26-3.28 (m, 4H), 3.74-3.76 (m, 4H), 4.15 (s, 3H), 6.59 (s, 3H), 7.29 (s, 1H), 7.49-7.53 (m, 1H), 7.52-7.62 (m, 1H).

Example 173

1-[(6,7-Difluoro-2-methoxyquinoxalin-3-yl)aminocarbonyl]-4-(3-trifluorotolyl)piperazine (Compound 173)

Ethyl N-(6,7-di fluoro-2-methoxyquinoxalin-3-yl)carbamate and 1-(3-trifluorotolyl)piperazine were reacted by the same way with the example 169 to obtain the titled compound (yield, 59%). $^1$H NMR (300 MHz, CDCl$_3$) δ 3.33-3.35 (m, 4H), 3.70-3.80 (m, 4H), 4.15 (s, 3H), 7.09-7.11 (m, 1H), 7.14-7.16 (m, 2H), 7.26 (s, 1H), 7.38-7.41 (m, 1H), 7.49-7.53 (m, 1H), 7.54 (br s, 1H).

Example 174

1-[(6,7-Difluoro-2-methoxyquinoxalin-3-yl)aminocarbonyl]-4-(3-chlorophenyl)piperazine (Compound 174)

Ethyl N-(6,7-di fluoro-2-methoxyquinoxalin-3-yl)carbamate and 1-(3-chlorophenyl)piperazine were reacted by the same way with the example 169 to obtain the titled compound (yield, 67%). $^1$H NMR (300 MHz, CDCl$_3$) δ 3.30 (m, 4H), 3.76 (m, 4H), 4.15 (s, 3H), 6.80-6.82 (m, 1H), 6.87-6.91 (m, 2H), 7.19-7.22 (m, 1H), 7.29 (br s, 1H), 7.49-7.51 (m, 1H), 7.60 (br s, 1H).

Example 175

1-[(6,7-Difluoro-2-methoxyquinoxalin-3-yl)aminocarbonyl]-4-(3-bromophenyl)piperazine (Compound 175)

Ethyl N-(6,7-di fluoro-2-methoxyquinoxalin-3-yl)carbamate and 1-(3-bromo phenyl)piperazine were reacted by the same way with the example 169 to obtain the titled compound (yield, 58%). $^1$H NMR (300 MHz, CDCl$_3$) δ 3.30 (m, 4H), 3.76 (m, 4H), 4.15 (s, 3H), 6.85-6.87 (m, 1H), 7.02-7.03 (m, 2H), 7.06-7.07 (m, 1H), 7.13-7.16 (m, 1H), 7.30 (br s, 1H), 7.51-7.53 (m, 1H), 7.60 (br s, 1H).

Example 176

1-[(6,7-Dichloro-2-methoxyquinoxalin-3-yl)aminocarbonyl]-4-(3-methoxyphenyl)piperazine (Compound 176)

1. a) 2-Amino-6,7-dichloro-3-methoxyquinoxaline

To 2-amino-3,6,7-tri chloroquinoxaline (1.54 g, 6.20 mmol) dissolved in tetrahydrofuran (40 ml), 25 wt % sodium methoxide (2.01 g, 9.30 mmol) in methanol was added at room temperature and stirred further at room temperature for 1 hour. The resulting mixture was concentrated under the reduced pressure to remove the solvent. The product was extracted with ethyl acetate and the organic layer was washed with water and dried over MgSO$_4$. After concentration under the reduced pressure, the crude product was purified by SiO$_2$ column chromatography. Extraction of the residue with a n-hexane:ethyl acetate (2:1) mixture and concentration gave 1.21 g of the titled compound (yield, 80%).

b) Ethyl N-(6,7-dichloro-2-methoxyquinoxalin-3-yl)carbamate

2-Amino-6,7-dichloro-3-methoxyquinoxaline (1.16 g, 4.75 mmol) and ethyl chloroformate (1.03 g, 9.50 mmol) were dissolved in dichloromethane (50 ml) at room temperature and thereto pyridine (751 mg, 9.50 mmol) was added. The mixture was stirred at room temperature for 24 hours and concentrated under the reduced pressure to remove the solvent, and purified by SiO$_2$ column chromatography. Extraction of the residue with a n-hexane:ethyl acetate (2:1) mixture and concentration gave 1.29 g of the titled compound (yield, 86%).

c) 1-[(6,7-Dichloro-2-methoxyquinoxalin-3-yl)aminocarbonyl]-4-(3-methoxyphenyl)piperazine Ethyl N-(6,7-dichloro-2-methoxyquinoxalin-3-yl)carbamate (28 mg, 0.089 mmol) and 1-(3-methoxy phenyl)piperazine (35 mg, 0.18 mmol) were dissolved in tetrahydrofuran (2 ml) at room temperature and thereto DBU (27 mg, 0.18 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (1:1) mixture and concentration gave 27 mg of the titled compound (yield, 66%). $^1$H NMR (300 MHz, CDCl$_3$) δ 3.28-3.30 (m, 4H), 3.74-3.76 (m, 4H), 3.81 (s, 3H), 4.19 (s, 3H), 6.47-6.49 (m, 3H), 6.53-6.57 (m, 1H), 7.30 (br s, 1H), 7.85 (s, 1H), 7.92 (s, 1H).

Example 177

1-[(6,7-Dichloro-2-methoxyquinoxalin-3-yl)aminocarbonyl]-4-(3,5-dimethoxyphenyl)piperazine (Compound 177)

Ethyl N-(6,7-dichloro-2-methoxyquinoxalin-3-yl)carbamate and 1-(3,5-di methoxyphenyl)piperazine were reacted by the same way with the example 176 to obtain the titled compound (yield, 68%). $^1$H NMR (300 MHz, CDCl$_3$) δ 3.28-3.30 (m, 4H), 3.74-3.78 (m, 4H), 3.79 (s, 6H), 4.15 (s, 3H), 6.07 (s, 1H), 6.11 (s, 2H), 7.33 (br s, 1H), 7.85 (s, 1H), 7.92 (s, 1H).

Example 178

1-[(6,7-Dichloro-2-methoxyquinoxalin-3-yl)aminocarbonyl]-4-(3-methylphenyl)piperazine (Compound 178)

Ethyl N-(6,7-dichloro-2-methoxyquinoxalin-3-yl)carbamate and 1-(3-methyl phenyl)piperazine were reacted by the same way with the example 176 to obtain the titled compound (yield, 71%). $^1$H NMR (300 MHz, CDCl$_3$) δ 2.34 (s, 3H), 3.18-3.21 (m, 4H), 3.75-3.79 (m, 4H), 4.14 (s, 3H), 6.75-6.78 (m, 4H), 7.32 (br s, 1H), 7.85 (s, 1H), 7.92 (s, 1H).

Example 179

1-[(6,7-Dichloro-2-methoxyquinoxalin-3-yl)aminocarbonyl]-4-(3,5-dimethylphenyl)piperazine (Compound 179)

Ethyl N-(6,7-dichloro-2-methoxyquinoxalin-3-yl)carbamate and 1-(3,5-dimethyl phenyl)piperazine were reacted by the same way with the example 176 to obtain the titled compound (yield, 55%). $^1$H NMR (300 MHz, CDCl$_3$) δ 2.30 (s, 6H), 3.16-3.21 (m, 4H), 3.75-3.79 (m, 4H), 4.15 (s, 3H), 6.52-6.59 (m, 3H), 7.31 (br s, 1H), 7.85 (s, 1H), 7.92 (s, 1H).

Example 180

1-[(6,7-Dichloro-2-methoxyquinoxalin-3-yl)aminocarbonyl]-4-(3-trifluorotolyl)piperazine (Compound 180)

Ethyl N-(6,7-dichloro-2-methoxyquinoxalin-3-yl)carbamate and 1-(3-trifluorotolyl)piperazine were reacted by the same way with the example 176 to obtain the titled compound (yield, 61%). $^1$H NMR (300 MHz, CDCl$_3$) δ 3.32-3.35 (m, 4H), 3.77 (m, 4H), 4.16 (s, 3H), 7.05-7.16 (m, 3H), 7.30 (br s, 1H), 7.33-7.39 (m, 1H), 7.86 (s, 1H), 7.91 (s, 1H).

Example 181

1-[(6,7-Dichloro-2-methoxyquinoxalin-3-yl)aminocarbonyl]-4-(3-chlorophenyl)piperazine (Compound 181)

Ethyl N-(6,7-dichloro-2-methoxyquinoxalin-3-yl)carbamate and 1-(3-chlorophenyl)piperazine were reacted by the same way with the example 176 to obtain the titled compound (yield, 61%). $^1$H NMR (300 MHz, CDCl$_3$) δ 3.31-3.30 (m, 4H), 3.75-3.76 (m, 4H), 4.15 (s, 3H), 6.80-6.82 (m, 1H), 6.90-6.91 (m, 2H), 7.18-7.23 (m, 1H), 7.32 (br s, 1H), 7.85 (s, 1H), 7.91 (s, 1H).

Example 182

1-[(6,7-Dichloro-2-methoxyquinoxalin-3-yl)aminocarbonyl]-4-(3-bromophenyl)piperazine (Compound 182)

Ethyl N-(6,7-dichloro-2-methoxyquinoxalin-3-yl)carbamate and 1-(3-bromo phenyl)piperazine were reacted by the same way with the example 176 to obtain the titled compound (yield, 72%). $^1$H NMR (300 MHz, CDCl$_3$) δ 3.29-3.31 (m, 4H), 3.74-3.76 (m, 4H), 4.16 (s, 3H), 6.85-6.87 (m, 1H), 7.02-7.04 (m, 1H), 7.06-7.07 (m, 1H), 7.13-7.15 (m, 1H), 7.32 (br s, 1H), 7.86 (br s, 1H), 7.86 (br s, 1H), 7.91 (br s, 1H).

Example 183

1-[(2-Methoxy-6,7-dimethylquinoxalin-3-yl)aminocarbonyl]-4-(3-methoxyphenyl)piperazine (Compound 183)

1. a) 2-Amino-3-methoxy-6,7-dimethylquinoxaline

To 2-amino-3-chloro-6,7-dimethyl quinoxaline (2.59 g, 12.5 mmol) dissolved in tetrahydrofuran (40 ml), 25 wt % sodium methoxide (4.05 g, 18.7 mmol) in methanol was added at room temperature and stirred further at room temperature for 1 hour. The resulting mixture was concentrated under the reduced pressure to remove the solvent. The product was extracted with ethyl acetate and the organic layer was washed with water and dried over MgSO$_4$. After concentration under the reduced pressure, the crude product was purified by SiO$_2$ column chromatography. Extraction of the residue with a n-hexane:ethyl acetate (2:1) mixture and concentration gave 2.38 g of the titled compound (yield, 94%).

b) Ethyl N-(2-methoxy-6,7-dimethylquinoxalin-3-yl)carbamate

2-Amino-3-methoxy-6,7-dimethylquinoxaline (2.34 g, 11.5 mmol) and ethyl chloroformate (2.50 g, 23.0 mmol) were dissolved in dichloromethane (50 ml) at room temperature and thereto pyridine (1.82 g, 23.0 mmol) was added. The mixture was stirred at room temperature for 12 hours and concentrated under the reduced pressure to remove the solvent, and purified by SiO$_2$ column chromatography. Extraction of the residue with a n-hexane:ethyl acetate (3:1) mixture and concentration gave 2.65 g of the titled compound (yield, 84%).

c) 1-[(2-Methoxy-6,7-dimethylquinoxalin-3-yl)aminocarbonyl]-4-(3-methoxyphenyl)piperazine Ethyl N-(2-methoxy-6,7-dimethylquinoxalin-3-yl)carbamate (35 mg, 0.13 mmol) and 1-(3-methoxy phenyl)piperazine (50 mg, 0.26 mmol) were dissolved in tetrahydrofuran (2 ml) at room temperature and thereto DBU (40 mg, 0.26 mmol) was added. The resulting mixture was stirred at 70° C. for 7 hours and concentrated under the reduced pressure to remove the solvent, and purified by SiO$_2$ column chromatography. Extraction of the residue with a n-hexane:ethyl acetate (2:1) mixture and concentration gave 37 mg of the titled compound (yield, 68%). $^1$H NMR (300 MHz, CDCl$_3$) δ 2.33 (s, 3H), 2.39 (s, 3H), 3.22-3.30 (m, 4H), 3.75 (m, 4H), 3.80 (s, 3H), 4.13 (s, 3H), 6.46-6.49 (m, 2H), 6.55-6.58 (m, 1H), 7.20-7.23 (m, 1H), 7.52 (s, 1H), 7.60 (s, 1H).

Example 184

1-[(2-Methoxy-6,7-dimethylquinoxalin-3-yl)aminocarbonyl]-4-(3,5-dimethoxyphenyl)piperazine (Compound 184)

Ethyl N-(2-methoxy-6,7-dimethylquinoxalin-3-yl)carbamate and 1-(3,5-di methoxyphenyl)piperazine were reacted by the same way with the example 183 to obtain the titled compound (yield, 75%). $^1$H NMR (300 MHz, CDCl$_3$) δ 2.33 (s, 3H), 2.39 (s, 3H), 3.21-3.29 (m, 4H), 3.75 (m, 4H), 3.79 (s, 3H), 4.11-4.13 (m, 3H), 6.06 (s, 1H), 6.12 (s, 2H), 7.52 (s, 1H), 7.59 (s, 1H).

Example 185

1-[(2-Methoxy-6,7-dimethylquinoxalin-3-yl)aminocarbonyl]-4-(3-methylphenyl)piperazine (Compound 185)

Ethyl N-(2-methoxy-6,7-dimethylquinoxalin-3-yl)carbamate and 1-(3-methylphenyl)piperazine were reacted by the same way with the example 183 to obtain the titled compound (yield, 49%). $^1$H NMR (300 MHz, CDCl$_3$) δ 2.33 (s, 6H), 2.40 (s, 3H), 3.21-3.31 (m, 4H), 3.74-4.11 (m, 3H), 4.13 (s, 4H), 6.71-6.78 (m, 3H), 7.16-7.20 (m, 1H), 7.36 (br s, 1H), 7.52 (s, 1H), 7.60 (s, 1H).

Example 186

1-[(2-Methoxy-6,7-dimethylquinoxalin-3-yl)aminocarbonyl]-4-(3,5-dimethylphenyl)piperazine (Compound 186)

Ethyl N-(2-methoxy-6,7-dimethylquinoxalin-3-yl)carbamate and 1-(3,5-dimethylphenyl)piperazine were reacted by the same way with the example 183 to obtain the titled compound (yield, 58%). $^1$H NMR (300 MHz, CDCl$_3$) δ 2.29-2.40 (m, 12H), 3.20-3.29 (m, 4H), 3.80-3.83 (m, 3H), 4.10 (s, 4H), 5.12 (br s, 1H), 6.59 (s, 3H), 7.36-7.60 (m, 2H).

Example 187

1-[(2-Methoxy-6,7-dimethylquinoxalin-3-yl)aminocarbonyl]-4-(3-trifluorotolyl)piperazine (Compound 187)

Ethyl N-(2-methoxy-6,7-dimethylquinoxalin-3-yl)carbamate and 1-(3-trifluorotolyl)piperazine were reacted by the same way with the example 183 to obtain the titled compound (yield, 63%). $^1$H NMR (300 MHz, CDCl$_3$) δ 2.33-2.40 (m, 6H), 3.27-3.38 (m, 4H), 3.78-3.79 (m, 3H), 4.13 (s, 4H), 7.08-7.14 (m, 2H), 7.36-7.40 (m, 2H), 7.53 (s, 1H), 7.59 (s, 1H).

Example 188

1-[(2-Methoxy-6,7-dimethylquinoxalin-3-yl)aminocarbonyl]-4-(3-chlorophenyl)piperazine (Compound 188)

Ethyl N-(2-methoxy-6,7-dimethylquinoxalin-3-yl)carbamate and 1-(3-chlorophenyl)piperazine were reacted by the same way with the example 183 to obtain the titled compound (yield, 71%). $^1$H NMR (300 MHz, CDCl$_3$) δ 2.33 (s, 3H), 2.40 (s, 3H), 3.23-3.30 (m, 4H), 3.74-3.77 (m, 3H), 4.13 (s, 4H), 6.80-6.91 (m, 3H), 7.15-7.20 (m, 1H), 7.36 (br s, 1H), 7.53 (s, 1H), 7.59 (s, 1H).

Example 189

1-[(2-Methoxy-6,7-dimethylquinoxalin-3-yl)aminocarbonyl]-4-(3-bromophenyl)piperazine (Compound 189)

Ethyl N-(2-methoxy-6,7-dimethylquinoxalin-3-yl)carbamate and 1-(3-bromo phenyl)piperazine were reacted by the same way with the example 183 to obtain the titled compound (yield, 69%). $^1$H NMR (300 MHz, CDCl$_3$) δ 2.33 (s, 3H), 2.40 (s, 3H), 3.22-3.31 (m, 4H), 3.73-3.76 (m, 3H), 4.13 (s, 4H), 6.85 (m, 1H), 7.00-7.20 (m, 3H), 7.40 (br s, 1H), 7.53 (s, 1H), 7.59 (s, 1H).

Example 190

1-[(2,6,7-Trimethoxyquinoxalin-3-yl)aminocarbonyl]-4-(3-methoxyphenyl)piperazine (Compound 190)

1. a) 2-Amino-3,6,7-trimethoxyquinoxaline

To 2-amino-3-chloro-6,7-dimethoxyquinoxaline (3.27 g, 13.6 mmol) dissolved in tetrahydrofuran (40 ml), 25 wt % sodium methoxide (4.41 g, 20.4 mmol) in methanol was added at room temperature and stirred further at room temperature for 2 hour. The resulting mixture was concentrated under the reduced pressure to remove the solvent. The product was extracted with dichloromethane and the organic layer was washed with water and dried over $MgSO_4$. After concentration under the reduced pressure, the crude product was purified by $SiO_2$ column chromatography. Extraction of the residue with a n-hexane:ethyl acetate (2:1) mixture and concentration gave 2.73 g of the titled compound (yield, 85%).

b) Ethyl N-(2,6,7-trimethoxyquinoxalin-3-yl)carbamate

2-Amino-3,6,7-trimethoxyquinoxaline (2.60 g, 11.0 mmol) and ethyl chloroformate (2.40 g, 22.1 mmol) were dissolved in dichloromethane (50 ml) at room temperature and thereto pyridine (1.75 g, 22.1 mmol) was added. The mixture was stirred at room temperature for 22 hours and concentrated under the reduced pressure to remove the solvent, and purified by $SiO_2$ column chromatography. Extraction of the residue with a n-hexane:ethyl acetate (2:1) mixture and concentration gave 3.04 g of the titled compound (yield, 90%).

c) 1-[(2,6,7-Trimethoxyquinoxalin-3-yl)aminocarbonyl]-4-(3-methoxyphenyl)piperazine Ethyl N-(2,6,7-trimethoxyquinoxalin-3-yl)carbamate (28 mg, 0.091 mmol) and 1-(3-methoxy phenyl)piperazine (27 mg, 0.18 mmol) were dissolved in tetrahydrofuran (2 ml) at room temperature and thereto DBU (27 mg, 0.18 mmol) was added. The resulting mixture was stirred at 70° C. for 7 hours and concentrated under the reduced pressure to remove the solvent, and purified by $SiO_2$ column chromatography. Extraction of the residue with a n-hexane:ethyl acetate (1:2) mixture and concentration gave 26 mg of the titled compound (yield, 64%). $^1$H NMR (300 MHz, $CDCl_3$) δ 3.27-3.29 (m, 4H), 3.78-3.81 (m, 7H), 3.94 (s, 3H), 3.97-3.98 (m, 1H), 4.00 (s, 3H), 4.15 (s, 3H), 6.47-6.49 (m, 2H), 6.56-6.58 (m, 1H), 7.11 (s, 1H), 7.14-7.27 (m, 3H).

Example 191

1-[(2,6,7-Trimethoxyquinoxalin-3-yl)aminocarbonyl]-4-(3,5-dimethoxyphenyl)piperazine (Compound 191)

Ethyl N-(2,6,7-trimethoxyquinoxalin-3-yl)carbamate and 1-(3,5-dimethoxyphenyl)piperazine were reacted by the same way with the example 190 to obtain the titled compound (yield, 68%). $^1$H NMR (300 MHz, $CDCl_3$) δ 3.28-3.29 (m, 4H), 3.75-3.79 (m, 4H), 3.97 (s, 3H), 4.00 (s, 3H), 4.13 (s, 3H), 6.07-6.11 (m, 3H), 7.14 (s, 1H), 7.27-7.28 (m, 2H).

Example 192

1-[(2,6,7-Trimethoxyquinoxalin-3-yl)aminocarbonyl]-4-(3-methylphenyl)piperazine (Compound 192)

Ethyl N-(2,6,7-trimethoxyquinoxalin-3-yl)carbamate and 1-(3-methylphenyl)piperazine were reacted by the same way with the example 190 to obtain the titled compound (yield, 56%). $^1$H NMR (300 MHz, $CDCl_3$) δ 2.34 (s, 3H), 3.25-3.30 (m, 4H), 3.76-3.80 (m, 4H), 3.98 (s, 3H), 4.02 (s, 3H), 4.16 (s, 3H), 6.74-6.78 (m, 3H), 7.14-7.26 (m, 4H).

Example 193

1-[(2,6,7-Trimethoxyquinoxalin-3-yl)aminocarbonyl]-4-(3,5-dimethylphenyl)piperazine (Compound 193)

Ethyl N-(2,6,7-trimethoxyquinoxalin-3-yl)carbamate and 1-(3,5-dimethylphenyl)piperazine were reacted by the same way with the example 190 to obtain the titled compound (yield, 56%). $^1$H NMR (300 MHz, $CDCl_3$) δ 2.28 (s, 3H), 2.30 (s, 3H), 3.26 (m, 4H), 3.77 (m, 4H), 3.97 (s, 3H), 4.00 (s, 3H), 4.13 (s, 3H), 6.59 (s, 3H), 7.14 (s, 1H), 7.27 (s, 1H).

Example 194

1-[(2,6,7-Trimethoxyquinoxalin-3-yl)aminocarbonyl]-4-(3-trifluorotolyl)piperazine (Compound 194)

Ethyl N-(2,6,7-trimethoxyquinoxalin-3-yl)carbamate and 1-(3-trifluorotolyl)piperazine were reacted by the same way with the example 190 to obtain the titled compound (yield, 67%) $^1$H NMR (300 MHz, $CDCl_3$) δ 3.34 (m, 4H), 3.81 (m, 4H), 3.97 (s, 3H), 4.00 (s, 3H), 4.13 (s, 3H), 7.09-7.11 (m, 2H), 7.14 (s, 3H), 7.25 (m, 1H), 7.38-7.41 (m, 1H).

Example 195

1-[(2,6,7-Trimethoxyquinoxalin-3-yl)aminocarbonyl]-4-(3-chlorophenyl)piperazine (Compound 195)

Ethyl N-(2,6,7-trimethoxyquinoxalin-3-yl)carbamate and 1-(3-chlorophenyl)piperazine were reacted by the same way with the example 190 to obtain the titled compound (yield, 74%). $^1$H NMR (300 MHz, $CDCl_3$) δ 3.29-3.31 (m, 4H), 3.79 (m, 4H), 3.97 (s, 3H), 4.00 (s, 3H), 4.12 (s, 3H), 6.82 (m, 1H), 6.86-6.88 (m, 1H), 6.89-6.91 (m, 1H), 7.14 (s, 1H), 7.19-7.22 (m, 3H).

Example 196

1-[(2,6,7-Trimethoxyquinoxalin-3-yl)aminocarbonyl]-4-(3-bromophenyl)piperazine (Compound 196)

Ethyl N-(2,6,7-trimethoxyquinoxalin-3-yl)carbamate and 1-(3-bromophenyl)piperazine were reacted by the same way with the example 190 to obtain the titled compound (yield, 63%). $^1$H NMR (300 MHz, $CDCl_3$) δ 3.28-3.30 (m, 4H), 3.78 (m, 4H), 3.97 (s, 3H), 3.99 (s, 3H), 4.13 (s, 3H), 6.86 (m, 1H), 7.01 (s, 1H), 7.06-7.07 (m, 1H), 7.13-7.16 (m, 2H), 7.22-7.28 (m, 2H).

The structures of compound 1 to 196 are presented in the following Table 1a-1f.

TABLE 1a

| Compounds | $R^1$ | $R^2$ | $R^3$ | $R^4$ | $R^5$ | $R^6$ | X | Y |
|---|---|---|---|---|---|---|---|---|
| 1 | F | H | Me | H | H | H | C—H | C—H |
| 2 | F | H | Me | H | H | H | C—OMe | C—H |

TABLE 1a-continued

Structure (1):

$R^1, R^2$ substituted quinoxaline connected via NH-C(=O)- to piperazine, connected to pyridine/pyrimidine ring with $R^4, R^5, R^6$, X, Y positions; $OR^3$ on quinoxaline.

| Compounds | R¹ | R² | R³ | R⁴ | R⁵ | R⁶ | X | Y |
|---|---|---|---|---|---|---|---|---|
| 3 | F | H | Me | OMe | H | H | C—H | C—H |
| 4 | F | H | Me | H | OMe | H | C—H | C—H |
| 5 | F | H | Me | OMe | H | OMe | C—H | C—H |
| 6 | F | H | Me | OMe | OMe | OMe | C—H | C—H |
| 7 | F | H | Me | H | H | H | C—Me | C—H |
| 8 | F | H | Me | Me | H | H | C—H | C—H |
| 9 | F | H | Me | H | H | H | C—Me | C—Me |
| 10 | F | H | Me | Me | H | Me | C—H | C—H |
| 11 | F | H | Me | CF₃ | H | H | C—H | C—H |
| 12 | F | H | Me | H | H | H | C—F | C—H |
| 13 | F | H | Me | H | F | H | C—H | C—H |
| 14 | F | H | Me | H | H | H | C—Cl | C—H |
| 15 | F | H | Me | Cl | H | H | C—H | C—H |
| 16 | F | H | Me | H | Cl | H | C—H | C—H |
| 17 | F | H | Me | H | H | H | C—CN | C—H |
| 18 | F | H | Me | H | Ac | H | C—H | C—H |
| 19 | F | H | Me | H | NO₂ | H | C—H | C—H |
| 20 | F | H | Me | H | H | H | N | C—H |
| 21 | F | H | Me | H | H | H | N | N |
| 22 | Cl | H | Me | H | H | H | C—H | C—H |
| 23 | Cl | H | Me | H | H | H | C—OMe | C—H |
| 24 | Cl | H | Me | OMe | H | H | C—H | C—H |
| 25 | Cl | H | Me | H | OMe | H | C—H | C—H |
| 26 | Cl | H | Me | OMe | H | OMe | C—H | C—H |
| 27 | Cl | H | Me | OMe | OMe | OMe | C—H | C—H |
| 28 | Cl | H | Me | H | H | H | C—Me | C—H |
| 29 | Cl | H | Me | Me | H | H | C—H | C—H |
| 30 | Cl | H | Me | H | H | H | C—Me | C—Me |

TABLE 1b

| | R¹ | R² | R³ | R⁴ | R⁵ | R⁶ | X | Y |
|---|---|---|---|---|---|---|---|---|
| 31 | Cl | H | Me | Me | H | Me | C—H | C—H |
| 32 | Cl | H | Me | CF₃ | H | H | C—H | C—H |
| 33 | Cl | H | Me | H | H | H | C—F | C—H |
| 34 | Cl | H | Me | H | F | H | C—H | C—H |
| 35 | Cl | H | Me | H | H | H | C—Cl | C—H |
| 36 | Cl | H | Me | Cl | H | H | C—H | C—H |
| 37 | Cl | H | Me | H | Cl | H | C—H | C—H |
| 38 | Cl | H | Me | H | H | H | C—CN | C—H |
| 39 | Cl | H | Me | H | Ac | H | C—H | C—H |
| 40 | Cl | H | Me | H | NO₂ | H | C—H | C—H |
| 41 | Cl | H | Me | H | H | H | N | C—H |
| 42 | Cl | H | Me | H | H | H | N | N |
| 43 | Me | H | Me | H | H | H | C—H | C—H |
| 44 | Me | H | Me | H | H | H | C—OMe | C—H |
| 45 | Me | H | Me | OMe | H | H | C—H | C—H |
| 46 | Me | H | Me | H | OMe | H | C—H | C—H |
| 47 | Me | H | Me | OMe | H | OMe | C—H | C—H |
| 48 | Me | H | Me | OMe | OMe | OMe | C—H | C—H |
| 49 | Me | H | Me | H | H | H | C—Me | C—H |
| 50 | Me | H | Me | Me | H | H | C—H | C—H |
| 51 | Me | H | Me | H | H | H | C—Me | C—Me |
| 52 | Me | H | Me | Me | H | Me | C—H | C—H |
| 53 | Me | H | Me | CF₃ | H | H | C—H | C—H |
| 54 | Me | H | Me | H | H | H | C—F | C—H |
| 55 | Me | H | Me | H | F | H | C—H | C—H |
| 56 | Me | H | Me | H | H | H | C—Cl | C—H |
| 57 | Me | H | Me | Cl | H | H | C—H | C—H |
| 58 | Me | H | Me | H | Cl | H | C—H | C—H |
| 59 | Me | H | Me | H | H | H | C—CN | C—H |
| 60 | Me | H | Me | H | Ac | H | C—H | C—H |
| 61 | Me | H | Me | H | NO₂ | H | C—H | C—H |
| 62 | Me | H | Me | H | H | H | N | C—H |
| 63 | Me | H | Me | H | H | H | N | N |
| 64 | MeO | H | Me | H | H | H | C—H | C—H |

TABLE 1b-continued

| | R¹ | R² | R³ | R⁴ | R⁵ | R⁶ | X | Y |
|---|---|---|---|---|---|---|---|---|
| 65 | MeO | H | Me | H | H | H | C—OMe | C—H |
| 66 | MeO | H | Me | OMe | H | H | C—H | C—H |
| 67 | MeO | H | Me | H | OMe | H | C—H | C—H |
| 68 | MeO | H | Me | OMe | H | OMe | C—H | C—H |
| 69 | MeO | H | Me | OMe | OMe | OMe | C—H | C—H |

TABLE 1c

| | R¹ | R² | R³ | R⁴ | R⁵ | R⁶ | X | Y |
|---|---|---|---|---|---|---|---|---|
| 70 | MeO | H | Me | H | H | H | C—Me | C—H |
| 71 | MeO | H | Me | Me | H | H | C—H | C—H |
| 72 | MeO | H | Me | H | H | H | C—Me | C—Me |
| 73 | MeO | H | Me | Me | H | Me | C—H | C—H |
| 74 | MeO | H | Me | CF₃ | H | H | C—H | C—H |
| 75 | MeO | H | Me | H | H | H | C—F | C—H |
| 76 | MeO | H | Me | H | F | H | C—H | C—H |
| 77 | MeO | H | Me | H | H | H | C—Cl | C—H |
| 78 | MeO | H | Me | Cl | H | H | C—H | C—H |
| 79 | MeO | H | Me | H | Cl | H | C—H | C—H |
| 80 | MeO | H | Me | H | H | H | C—CN | C—H |
| 81 | MeO | H | Me | H | Ac | H | C—H | C—H |
| 82 | MeO | H | Me | H | NO₂ | H | C—H | C—H |
| 83 | MeO | H | Me | H | H | H | N | C—H |
| 84 | MeO | H | Me | H | H | H | N | N |
| 85 | H | F | Me | H | H | H | C—H | C—H |
| 86 | H | F | Me | H | H | H | C—OMe | C—H |
| 87 | H | F | Me | OMe | H | H | C—H | C—H |
| 88 | H | F | Me | H | OMe | H | C—H | C—H |
| 89 | H | F | Me | OMe | H | OMe | C—H | C—H |
| 90 | H | F | Me | OMe | OMe | OMe | C—H | C—H |
| 91 | H | F | Me | H | H | H | C—Me | C—H |
| 92 | H | F | Me | Me | H | H | C—H | C—H |
| 93 | H | F | Me | H | H | H | C—Me | C—Me |
| 94 | H | F | Me | Me | H | Me | C—H | C—H |
| 95 | H | F | Me | CF₃ | H | H | C—H | C—H |
| 96 | H | F | Me | H | H | H | C—F | C—H |
| 97 | H | F | Me | H | F | H | C—H | C—H |
| 98 | H | F | Me | H | H | H | C—Cl | C—H |
| 99 | H | F | Me | Cl | H | H | C—H | C—H |
| 100 | H | F | Me | H | Cl | H | C—H | C—H |
| 101 | H | F | Me | H | H | H | C—CN | C—H |
| 102 | H | F | Me | H | Ac | H | C—H | C—H |
| 103 | H | F | Me | H | NO₂ | H | C—H | C—H |
| 104 | H | F | Me | H | H | H | N | C—H |
| 105 | H | F | Me | H | H | H | N | N |
| 106 | H | Cl | Me | H | H | H | C—H | C—H |
| 107 | H | Cl | Me | H | H | H | C—OMe | C—H |
| 108 | H | Cl | Me | OMe | H | H | C—H | C—H |
| 109 | H | Cl | Me | H | OMe | H | C—H | C—H |
| 110 | H | Cl | Me | OMe | H | OMe | C—H | C—H |

TABLE 1d

| | R¹ | R² | R³ | R⁴ | R⁵ | R⁶ | X | Y |
|---|---|---|---|---|---|---|---|---|
| 111 | H | Cl | Me | OMe | OMe | OMe | C—H | C—H |
| 112 | H | Cl | Me | H | H | H | C—Me | C—H |
| 113 | H | Cl | Me | Me | H | H | C—H | C—H |
| 114 | H | Cl | Me | H | H | H | C—Me | C—Me |
| 115 | H | Cl | Me | Me | H | Me | C—H | C—H |
| 116 | H | Cl | Me | CF₃ | H | H | C—H | C—H |
| 117 | H | Cl | Me | H | H | H | C—F | C—H |
| 118 | H | Cl | Me | H | F | H | C—H | C—H |
| 119 | H | Cl | Me | H | H | H | C—Cl | C—H |
| 120 | H | Cl | Me | Cl | H | H | C—H | C—H |
| 121 | H | Cl | Me | H | Cl | H | C—H | C—H |
| 122 | H | Cl | Me | H | H | H | C—CN | C—H |
| 123 | H | Cl | Me | H | Ac | H | C—H | C—H |
| 124 | H | Cl | Me | H | NO₂ | H | C—H | C—H |
| 125 | H | Cl | Me | H | H | H | N | C—H |
| 126 | H | Cl | Me | H | H | H | N | N |
| 127 | H | Me | Me | H | H | H | C—H | C—H |
| 128 | H | Me | Me | H | H | H | C—OMe | C—H |
| 129 | H | Me | Me | OMe | H | H | C—H | C—H |
| 130 | H | Me | Me | H | OMe | H | C—H | C—H |
| 131 | H | Me | Me | OMe | H | OMe | C—H | C—H |
| 132 | H | Me | Me | OMe | OMe | OMe | C—H | C—H |
| 133 | H | Me | Me | H | H | H | C—Me | C—H |

TABLE 1d-continued

| | | | | | | | | |
|---|---|---|---|---|---|---|---|---|
| 134 | H | Me | Me | Me | H | H | C—H | C—H |
| 135 | H | Me | Me | H | H | H | C—Me | C—Me |
| 136 | H | Me | Me | Me | H | Me | C—H | C—H |
| 137 | H | Me | Me | CF$_3$ | H | H | C—H | C—H |
| 138 | H | Me | Me | H | H | H | C—F | C—H |
| 139 | H | Me | Me | H | F | H | C—H | C—H |
| 140 | H | Me | Me | H | H | H | C—Cl | C—H |
| 141 | H | Me | Me | Cl | H | H | C—H | C—H |
| 142 | H | Me | Me | H | Cl | H | C—H | C—H |
| 143 | H | Me | Me | H | H | H | C—CN | C—H |
| 144 | H | Me | Me | H | Ac | H | C—H | C—H |
| 145 | H | Me | Me | H | NO$_2$ | H | C—H | C—H |
| 146 | H | Me | Me | H | H | H | N | C—H |
| 147 | H | Me | Me | H | H | H | N | N |
| 148 | H | MeO | Me | H | H | H | C—H | C—H |
| 149 | H | MeO | Me | H | H | H | C—OMe | C—H |

TABLE 1e

| | | | | | | | | |
|---|---|---|---|---|---|---|---|---|
| 150 | H | MeO | Me | OMe | H | H | C—H | C—H |
| 151 | H | MeO | Me | H | OMe | H | C—H | C—H |
| 152 | H | MeO | Me | OMe | H | OMe | C—H | C—H |
| 153 | H | MeO | Me | OMe | OMe | OMe | C—H | C—H |
| 154 | H | MeO | Me | H | H | H | C—Me | C—H |
| 155 | H | MeO | Me | Me | H | H | C—H | C—H |
| 156 | H | MeO | Me | H | H | H | C—Me | C—Me |
| 157 | H | MeO | Me | Me | H | Me | C—H | C—H |
| 158 | H | MeO | Me | CF$_3$ | H | H | C—H | C—H |
| 159 | H | MeO | Me | H | H | H | C—F | C—H |
| 160 | H | MeO | Me | H | F | H | C—H | C—H |
| 161 | H | MeO | Me | H | H | H | C—Cl | C—H |
| 162 | H | MeO | Me | Cl | H | H | C—H | C—H |
| 163 | H | MeO | Me | H | Cl | H | C—H | C—H |
| 164 | H | MeO | Me | H | H | H | C—CN | C—H |
| 165 | H | MeO | Me | H | Ac | H | C—H | C—H |
| 166 | H | MeO | Me | H | NO$_2$ | H | C—H | C—H |
| 167 | H | MeO | Me | H | H | H | N | C—H |
| 168 | H | MeO | Me | H | H | H | N | N |
| 169 | F | F | Me | OMe | H | H | C—H | C—H |
| 170 | F | F | Me | OMe | H | OMe | C—H | C—H |
| 171 | F | F | Me | Me | H | H | C—H | C—H |
| 172 | F | F | Me | Me | H | Me | C—H | C—H |
| 173 | F | F | Me | CF$_3$ | H | H | C—H | C—H |
| 174 | F | F | Me | Cl | H | H | C—H | C—H |
| 175 | F | F | Me | Br | H | H | C—H | C—H |
| 176 | Cl | Cl | Me | OMe | H | H | C—H | C—H |
| 177 | Cl | Cl | Me | OMe | H | OMe | C—H | C—H |
| 178 | Cl | Cl | Me | Me | H | H | C—H | C—H |
| 179 | Cl | Cl | Me | Me | H | Me | C—H | C—H |
| 180 | Cl | Cl | Me | CF$_3$ | H | H | C—H | C—H |
| 181 | Cl | Cl | Me | Cl | H | H | C—H | C—H |
| 182 | Cl | Cl | Me | Br | H | H | C—H | C—H |
| 183 | Me | Me | Me | OMe | H | H | C—H | C—H |
| 184 | Me | Me | Me | OMe | H | OMe | C—H | C—H |
| 185 | Me | Me | Me | Me | H | H | C—H | C—H |
| 186 | Me | Me | Me | Me | H | Me | C—H | C—H |
| 187 | Me | Me | Me | CF$_3$ | H | H | C—H | C—H |
| 188 | Me | Me | Me | Cl | H | H | C—H | C—H |

TABLE 1f

| | | | | | | | | |
|---|---|---|---|---|---|---|---|---|
| 189 | Me | Me | Me | Br | H | H | C—H | C—H |
| 190 | MeO | MeO | Me | OMe | H | H | C—H | C—H |
| 191 | MeO | MeO | Me | OMe | H | OMe | C—H | C—H |
| 192 | MeO | MeO | Me | Me | H | H | C—H | C—H |
| 193 | MeO | MeO | Me | Me | H | Me | C—H | C—H |
| 194 | MeO | MeO | Me | CF$_3$ | H | H | C—H | C—H |
| 195 | MeO | MeO | Me | Cl | H | H | C—H | C—H |
| 196 | MeO | MeO | Me | Br | H | H | C—H | C—H |

Pharmaceutical Preparation

The followings illustrate representative pharmaceutical dosage forms containing the compound of formula (1), or a pharmaceutically acceptable salt thereof (hereafter compound X) for therapeutic or prophylactic use in humans. The formulations may be obtained by conventional procedures well known in the pharmaceutical art and are not limited to the representative pharmaceutical dosage forms.

1) Tablet (Direct Pressure)

5.0 mg of sieved compound X was mixed with 14.1 mg of lactose, 0.8 mg of Crosspovidone USNF and 0.1 mg of magnesium stearate and the mixture was compressed into tablets.

2) Tablet (Hydroassembly)

5.0 mg of sieved compound X was mixed with 16.0 mg of lactose and 4.0 mg of starch and 0.3 mg of polysorbate 80 dissolved in pure water was added thereto. After making particle with the mixture, the particle was dried, sieved and mixed with 2.7 mg of colloidal silicon dioxide and 2.0 mg of magnesium stearate. The particle was compressed into tablets.

3) Powder and Capsule 5.0 mg of sieved compound X was mixed with 14.8 mg of lactose, 10.0 mg of polvinylpolypyrrolidone and 0.2 mg of magnesium stearate and the mixture was filled into No. 5 gelatin capsule using suitable equipment.

4) Injection 100 mg of compound X, 180 mg of mannitol and 26 mg of Na$_2$HPO$_4$.12H$_2$O were dissolved in 2974 ml of distilled water.

Biological Tests

1. Growth of Cancer Cell Lines

Cancer cells used in this study to determine the effect of quinazoline compounds were obtained from the following sources: Human OVCAR-3 (ovary), MCF-7 (breast, hormone-dependent), MDA-MB-231 (breast), PC3 (prostate), HepG2 (liver), A549 (lung), Caki-1 (kidney), HT-29 (colon), HCT116 (colon) and PANC-1 (pancreas) from the American Type Culture Collection (ATCC) (Manassas, Va.); MKN-45 (stomach) from DSMZ (Germany); UMRC2 (kidney) from the U.S. National Cancer Institute (Bethesda, Md.); Huvec (human umbilical vein endothelial cells), HEK293 (human embryonic kidney) and SK-OV-3 (ovary) from Korean Cell Line Bank (Seoul, Korea). OVCAR-3, MCF-7, PC3, HepG2, A549, HT-29 and MKN-45 were grown in RPMI1640 medium (Invitrogen, Carlsbad, Calif.) supplemented with 10% fetal bovine serum ('FBS'), 1 mM sodium pyruvate, 10 mM HEPES and 100 U/ml penicillin and 100 mg/ml streptomycin ('P/S'). MDA-MB-231, HCT116, UMRC2, Caki-1, PANC-1 and HEK293 cells were maintained in Dulbecco's modified Eagle's medium ('DMEM', Invitrogen) supplemented with 10% FBS, P/S, 10 mM HEPES and 2 mM L-glutamine. HUVEC was maintained in M199 supplemented with basic fibroblast growth factor ('bFGF') 3 mg/ml, Heparn 100 mg/ml and FBS 20%. All cells were incubated at 37° C. under humidified 5% CO$_2$.

2. Cell Growth Inhibition Assay

The growth inhibition of the substituted quinoxalin-piperazine compounds against a variety of human tumor cells was evaluated. The relative importance of particular substituent groups on the compounds was also studied. The substituted piperazine derivative compounds, prepared as described above, were tested, along with DMSO as a control.

The growth inhibition assay of various compounds against human tumor cell lines was performed using the Sulforhodamine B ('SRB') method (Skehan et al., *J. National Cancer Institute*, 1990, 82, 1107-1112). Briefly, exponentially growing tumor cells were seeded into a 96-well plate at a density of 2~3×10³ cells/well and treated with quinazoline compounds the next day. Triplicate wells were used for each treatment. The cells were incubated with the various compounds for 96 hours at 37° C. in a humidified 5% $CO_2$ atmosphere. After 96-hour incubation, cells were fixed with 10% trichloroacetic acid ('TCA'), incubated for 1 hour at 4° C., and washed 3 times with tap water. Subsequently cells were stained with 0.4% sulforhodamine B in 1% acetic acid for 30 minutes, washed 4 times with 1% acetic acid, and air-dried again. After 5 minutes agitation in 10 mM Tris solution, the absorbance of each well was measured at 530 nm using Benchmark Plus Microplate reader (Bio-Rad Laboratories, Hercules, Calif.).

To translate the $OD_{530}$ values into the number of live cells in each well, the $OD_{530}$ values were compared to those on standard $OD_{530}$—versus—cell number curves generated for each cell line. The percent survival was calculated using the formula:

% Survival=live cell number[test]/live cell number [control]×100

The $IC_{50}$ values were calculated by non-linear regression analysis.

Using QSAR and combinatorial chemistry techniques, a large number of compounds, including the compounds shown in Table 1a-1f above, were synthesized. The synthesized compounds were screened against at least three cell lines, PANC-1, MDA-MB-231 and UMRC2, at approximately 1 μM concentration. Compounds showing activity in at least one of these cell lines were selected for further screening. From these compounds, fifty compounds were selected for further evaluation as broad spectrum anti-proliferative agents as shown in the following Table 2a-2b.

TABLE 2a

Inhibition of cell growth ($IC_{50}$, μM) by quinoxaline-piperazine compounds against human cancer cell lines

| No. of compound | MDA-MB-231 | UMRC2 | PANC-1 | MKN45 | HepG2 | HT29 | HCT116 | PC-3 | OVCAR3 | MCF7 | Caki-1 | A549 | Hek293 | Huvec | SK-OV-3 |
|---|---|---|---|---|---|---|---|---|---|---|---|---|---|---|---|
| 2 | 0.064 | 0.10 | 0.35 | 0.093 | 0.12 | 0.15 | 0.16 | 0.22 | 0.076 | 0.19 | 0.11 | 0.20 | | | |
| 3 | 0.063 | 0.050 | 0.062 | 0.050 | 0.12 | 0.090 | 0.064 | 0.070 | 0.036 | 0.070 | 0.047 | 0.15 | | | |
| 5 | 0.012 | 0.013 | 0.021 | 0.020 | 0.019 | 0.021 | 0.019 | 0.021 | 0.012 | 0.025 | 0.011 | 0.021 | | | |
| 8 | 0.036 | 0.032 | 0.039 | 0.023 | 0.080 | 0.050 | 0.043 | 0.060 | 0.024 | 0.034 | 0.024 | 0.081 | | | |
| 10 | 0.023 | 0.022 | 0.024 | 0.027 | 0.021 | 0.031 | 0.025 | 0.022 | 0.025 | 0.031 | 0.019 | 0.023 | 0.25 | 0.05 | 0.1 |
| 11 | 0.25 | 0.39 | 1.06 | | | | | | | | | | | | |
| 15 | 0.040 | 0.077 | 0.28 | 0.076 | 0.077 | 0.11 | 0.097 | 0.13 | 0.055 | 0.13 | 0.064 | 0.10 | | | |
| 24 | 0.41 | 0.68 | 1.66 | | | | | | | | | | | | |
| 26 | 0.050 | 0.065 | 0.098 | 0.064 | 0.063 | 0.079 | 0.068 | 0.076 | 0.042 | 0.076 | 0.053 | 0.073 | | | |
| 29 | 0.16 | 0.30 | 0.95 | | | | | | | | | | | | |
| 31 | 0.037 | 0.060 | 0.24 | 0.069 | 0.068 | 0.11 | 0.076 | 0.079 | 0.056 | 0.081 | 0.056 | 0.076 | 0.25 | 0.1 | 0.1 |
| 32 | 1.0 | 1.0 | >1.0 | | | | | | | | | | | | |
| 36 | 0.17 | 0.31 | 0.93 | | | | | | | | | | | | |
| 45 | 0.27 | 0.45 | 1.31 | | | 0.05 | | | | | | 0.25 | 0.5 | 0.5 | 1.0 |
| 47 | 0.032 | 0.039 | 0.070 | 0.040 | 0.045 | 0.048 | 0.047 | 0.063 | 0.023 | 0.063 | 0.029 | 0.055 | | | |
| 50 | 0.22 | 0.40 | 1.04 | | | | | | | | | | | | |
| 52 | 0.050 | 0.050 | 0.28 | 0.080 | 0.081 | 0.14 | 0.10 | 0.11 | 0.065 | 0.12 | 0.071 | 0.097 | 0.1 | 0.1 | 0.25 |
| 53 | >1.0 | >1.0 | >1.0 | | | | | | | | | | | | |
| 57 | 0.14 | 0.24 | 0.64 | | | | | | | | | | | | |
| 66 | >1.0 | >1.0 | >1.0 | | | | | | | | | | | | |
| 71 | 0.40 | 0.63 | 1.43 | | | | | | | | | | | | |
| 73 | 0.057 | 0.10 | 0.33 | 0.081 | 0.081 | 0.12 | 0.11 | 0.14 | 0.059 | 0.097 | 0.066 | 0.11 | 0.1 | 0.1 | 0.1 |
| 78 | >1.0 | >1.0 | >1.0 | | | | | | | | | | | | |
| 87 | >1.0 | >1.0 | >1.0 | | | | | | | | | | | | |
| 92 | 0.21 | 0.37 | 0.95 | | | | | | | | | | | | |

TABLE 2b

| | | | | | | | | | | | | | | | |
|---|---|---|---|---|---|---|---|---|---|---|---|---|---|---|---|
| 94 | 0.41 | 0.32 | 0.56 | 0.25 | 0.48 | 0.89 | 0.40 | 0.70 | 0.29 | 0.36 | 0.33 | 0.42 | 0.57 | 0.16 | 0.50 |
| 95 | >1.0 | >1.0 | >1.0 | | | | | | | | | | | | |
| 108 | >1.0 | >1.0 | >1.0 | | | | | | | | | | | | |
| 110 | 0.18 | 0.21 | 0.28 | 0.20 | 0.21 | 0.25 | 0.23 | 0.27 | 0.13 | 0.21 | 0.18 | 0.24 | | | |
| 113 | 0.30 | 0.40 | 0.61 | | | | | | | | | | | | |
| 115 | 0.13 | 0.11 | 0.17 | 0.43 | 0.41 | 0.46 | 0.45 | 0.62 | 0.31 | 0.45 | 0.31 | 0.59 | 0.50 | 0.52 | 0.50 |
| 116 | >1.0 | >1.0 | >1.0 | | | | | | | | | | | | |
| 120 | 0.17 | 0.17 | 0.24 | | | | | 0.48 | | 0.36 | 0.60 | 0.40 | 0.75 | | |
| 129 | >1.0 | >1.0 | >1.0 | | | | | | | | | | | | |
| 131 | 0.16 | 0.23 | 0.36 | 0.22 | 0.23 | 0.34 | 0.25 | 0.35 | 0.14 | 0.24 | 0.19 | 0.24 | | | |
| 134 | 0.26 | 0.26 | N/A | | | | | | | | | | | | |
| 136 | 0.045 | 0.057 | 0.28 | 0.18 | 0.19 | 0.24 | 0.20 | 0.25 | 0.14 | 0.21 | 0.13 | 0.21 | 0.24 | 0.15 | 0.10 |
| 141 | 0.25 | 0.25 | N/A | | | | | | | | | | | | |
| 150 | 1.0 | >1.0 | >1.0 | | | | | | | | | | | | |
| 155 | 0.23 | 0.39 | 0.96 | | | | | | | | | | | | |
| 157 | 0.41 | 0.27 | 0.47 | 0.27 | 0.56 | 0.78 | 0.38 | 0.58 | 0.29 | 0.21 | 0.30 | 2.50 | 0.53 | 0.15 | 0.50 |
| 158 | >1.0 | >1.0 | >1.0 | | | | | | | | | | | | |
| 162 | 0.23 | 0.29 | 0.46 | | | | | | | | | | | | |
| 167 | >1.0 | >1.0 | >1.0 | | | | | | | | | | | | |
| 172 | 0.70 | 0.56 | 1.00 | | | | | | | | | | | | |

TABLE 2b-continued

| | | | |
|---|---|---|---|
| 177 | 1.45 | 0.58 | 1.16 |
| 191 | 0.69 | 0.49 | 0.90 |
| 193 | 0.65 | 0.47 | 0.69 |
| 194 | 0.75 | 0.79 | 1.40 |
| 196 | 0.72 | 0.65 | 1.05 |

INDUSTRIAL APPLICABILITY

The novel compounds of the present invention may provided novel quinoxaline-piperazine derivatives or pharmaceutically acceptable salts thereof which have the strong antiproliferative effect and are useful for treating hyperproliferative disorders, including cancers, by administering quinoxaline-piperazine compounds.

The invention claimed is:

1. A compound of the formula (1), or pharmaceutically acceptable salts thereof,

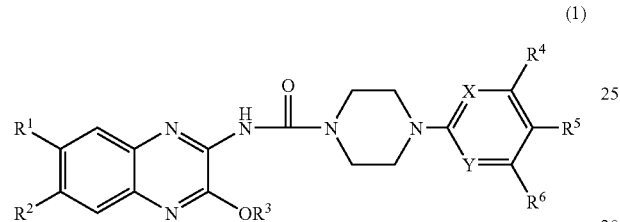

(1)

wherein
X is C—$R^7$;
Y is C—H;
for the combination of variables $R^1$ and $R^2$:
  $R^1$ is hydrogen, $C_1$-$C_3$ alkoxy, $C_1$-$C_3$ alkyl or halogen and $R^2$ is F; or
  $R^1$ is F and $R^2$ is hydrogen, $C_1$-$C_3$ alkoxy, $C_1$-$C_3$ alkyl or halogen;
$R^3$ is $C_1$-$C_3$ alkyl;
$R^4$ is hydrogen, $C_1$-$C_3$ alkoxy, $C_1$-$C_3$ alkyl, or halogen;
$R^5$ is H;
$R^6$ is H, $C_1$-$C_3$ alkoxy, or $C_1$-$C_3$ alkyl; and
$R^7$ is H or $C_1$-$C_3$ alkoxy.

2. The compound of claim 1, wherein:
for the combination of variables $R^1$ and $R^2$:
  $R^1$ is F and $R^2$ is hydrogen or $CH_3$;
$R^3$ is $CH_3$;
$R^4$ is H, $OCH_3$, $CH_3$, or Cl;
$R^5$ is H;
$R^6$ is H, $OCH_3$, or $CH_3$; and
$R^7$ is H or $OCH_3$.

3. The compound of claim 2, wherein
$R^1$ is F,
$R^2$ is H;
$R^3$ is $CH_3$;
$R^4$ is $OCH_3$ or $CH_3$;
$R^5$ is H;
$R^6$ is H, $OCH_3$, or $CH_3$; and
X is C—H.

4. The compound of claim 3, wherein
$R^1$ is F,
$R^2$ is H;
$R^3$ is $CH_3$;
$R^4$ is $OCH_3$ or $CH_3$;
$R^5$ is H;
$R^6$ is $OCH_3$, or $CH_3$; and
X is C—H.

5. The compound of claim 4, wherein
$R^1$ is F,
$R^2$ is H;
$R^3$ is $CH_3$;
$R^4$ and $R^6$ are both $OCH_3$ or $CH_3$;
$R^5$ is H; and
X is C—H.

6. The compound of claim 1, wherein:
for the combination of variables $R^1$ and $R^2$:
  $R^1$ is hydrogen, $OCH_3$, Cl or F and $R^2$ is F; or
  $R^1$ is F and $R^2$ is hydrogen, $OCH_3$, Cl or F;
$R^3$ is $CH_3$;
$R^4$ is H, $OCH_3$, $CH_3$, or Cl;
$R^5$ is H;
$R^6$ is H, $OCH_3$, or $CH_3$; and
$R^7$ is H or $OCH_3$.

7. A pharmaceutical composition which comprises a compound of the formula (1) as claimed in claim 1, or pharmaceutically-acceptable salts thereof, in association with a pharmaceutically-acceptable diluent or carrier.

8. The compound of claim 1, wherein the compound is

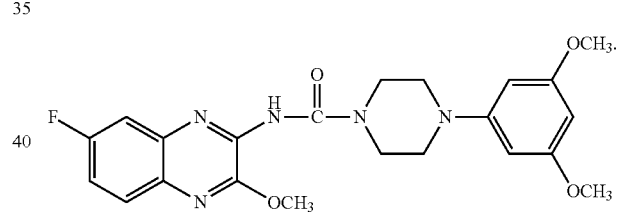

9. A pharmaceutical composition which comprises a compound of the formula (1) as claimed in claim 8, or pharmaceutically-acceptable salts thereof, in association with a pharmaceutically-acceptable diluent or carrier.

10. The compound of claim 1, wherein the compound is selected from the group consisting of

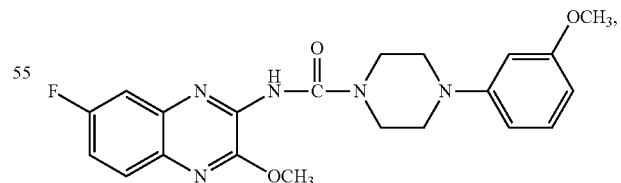

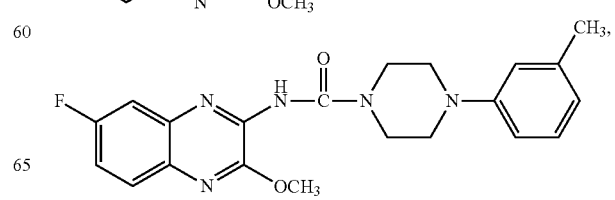

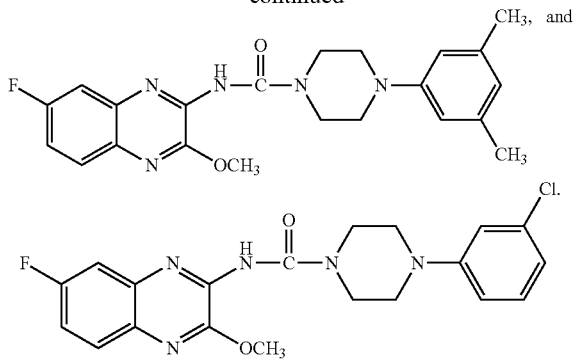

11. A pharmaceutical composition which comprises a compound of the formula (1) as claimed in claim 10, or pharmaceutically-acceptable salts thereof, in association with a pharmaceutically-acceptable diluent or carrier.

12. A process for the preparation of a compound of claim 1, comprising
reacting a compound of formula (6) with 1.0-5.0 equivalents of 2,4-dimethoxybenzylamine in dimethylsulfoxide to give a compound of formula (7);
reacting the compound of formula (7) with trifluoroacetic acid (TFA) in dichloromethane to give a compound of formula (2);
reacting the compound of formula (2) with 1.0-1.5 equivalents of L-C(=O)-L' in an organic solvent in the presence of a base at room temperature to 100° C. to obtain a compound of formula (3); and
reacting the compound of formula (3) with 1.0-1.5 equivalents of a compound of formula (4) in an organic solvent in the presence of a base at 50° C. to 100° C., to give the compound of formula (1);

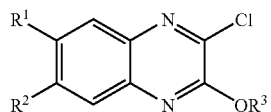

wherein L and L' are independently imidazole, Cl, ethoxy, phenoxy or 4-nitrophenoxy.

* * * * *